(12) United States Patent
McBrady et al.

(10) Patent No.: US 12,209,941 B2
(45) Date of Patent: *Jan. 28, 2025

(54) FLUID COMPOSITION SENSOR DEVICE AND METHOD OF USING THE SAME

(71) Applicant: Honeywell International Inc., Charlotte, NC (US)

(72) Inventors: Adam Dewey McBrady, Dallas, TX (US); Stephan Michael Bork, Murphy, TX (US)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,297

(22) Filed: Oct. 10, 2023

(65) Prior Publication Data

US 2024/0044767 A1 Feb. 8, 2024

Related U.S. Application Data

(63) Continuation of application No. 17/080,344, filed on Oct. 26, 2020, now Pat. No. 11,835,432.

(51) Int. Cl.
*G01N 15/08* (2006.01)
*G01N 15/0227* (2024.01)
(Continued)

(52) U.S. Cl.
CPC ..... *G01N 15/0606* (2013.01); *G01N 15/0227* (2013.01); *G01N 15/0618* (2013.01);
(Continued)

(58) Field of Classification Search
CPC ........... G01N 15/0227; G01N 15/0272; G01N 15/0606; G01N 15/0618; G01N 15/0625;
(Continued)

(56) References Cited

U.S. PATENT DOCUMENTS 4,021,117 A  5/1977  Gohde et al.
4,232,967 A  11/1980  Grachev et al.
(Continued)

FOREIGN PATENT DOCUMENTS

AU  2018101327 A4  10/2018
CA  2326811 A1  5/2002
(Continued)

OTHER PUBLICATIONS

Notice of Allowance received for U.S. Appl. No. 16/748,543, mailed on Oct. 1, 2021, 2 pages.
(Continued)

*Primary Examiner* — Paul M. West
(74) *Attorney, Agent, or Firm* — Alston & Bird LLP

(57) ABSTRACT

Various embodiments described herein relate to apparatuses and methods for detecting fluid particles and their characteristics. In various embodiments, a device for detecting fluid particles and their characteristics may comprise a fluid composition sensor configured to receive a volume of fluid. The fluid composition sensor has a collection media housing configured to receive a portion of a collection media, a pump for moving a volume of fluid over the collection media housing, an imaging device configured to capture an image of particles on the collection media, and a particle matter mass concentration calculation circuitry configured to calculate a total particle matter mass. The particle matter mass concentration calculation circuitry is connected with the imaging device and the pump. The particle matter mass concentration calculation circuitry is configured to adjust the volume of fluid over the collection media housing.

17 Claims, 23 Drawing Sheets

(51) Int. Cl.
*G01N 15/06* (2006.01)
*G01N 15/14* (2024.01)
*G01N 15/1433* (2024.01)
*G01N 33/00* (2006.01)

(52) U.S. Cl.
CPC ....... *G01N 15/0625* (2013.01); *G01N 15/082* (2013.01); *G01N 15/1433* (2024.01); *G01N 33/0004* (2013.01); *G01N 2015/1402* (2013.01)

(58) Field of Classification Search
CPC .............. G01N 15/082; G01N 15/1433; G01N 2015/1402; G01N 33/0004
See application file for complete search history.

(56) References Cited

U.S. PATENT DOCUMENTS

| | | |
|---|---|---|
| 4,839,529 A | 6/1989 | Fruengel |
| 5,001,463 A | 3/1991 | Hamburger |
| 5,040,424 A | 8/1991 | Marple et al. |
| 5,257,087 A | 10/1993 | Furuya |
| 5,404,217 A | 4/1995 | Janik et al. |
| 5,426,501 A | 6/1995 | Hokanson et al. |
| 5,440,145 A | 8/1995 | Cole |
| 5,646,597 A | 7/1997 | Hamburger et al. |
| 5,790,246 A | 8/1998 | Kuhnell et al. |
| 5,870,189 A | 2/1999 | Uesugi et al. |
| 5,870,190 A | 2/1999 | Unger |
| 5,932,795 A | 8/1999 | Koutrakis et al. |
| 6,049,381 A | 4/2000 | Reintjes et al. |
| 6,101,886 A | 8/2000 | Brenizer et al. |
| 6,115,119 A | 9/2000 | Sieracki et al. |
| 6,435,043 B1 | 8/2002 | Ferguson et al. |
| 6,463,814 B1 | 10/2002 | Letarte et al. |
| 6,562,583 B1 | 5/2003 | Herbig et al. |
| 6,629,449 B1 | 10/2003 | Kline-Schoder et al. |
| 6,729,196 B2 | 5/2004 | Moler et al. |
| 6,887,710 B2 | 5/2005 | Call et al. |
| 6,909,269 B2 | 6/2005 | Nagai et al. |
| 7,518,710 B2 | 4/2009 | Gao et al. |
| 7,633,606 B2 | 12/2009 | Northrup et al. |
| 7,762,677 B2 | 7/2010 | Lundgren |
| 7,799,567 B1 | 9/2010 | Call |
| 7,895,000 B2 | 2/2011 | Chandler et al. |
| 8,219,249 B2 | 7/2012 | Harrod et al. |
| 8,506,686 B2 | 8/2013 | Langle et al. |
| 8,866,063 B2 | 10/2014 | Ozcan et al. |
| 9,007,433 B2 | 4/2015 | Ozcan et al. |
| 9,057,702 B2 | 6/2015 | Ozcan et al. |
| 9,057,708 B2 | 6/2015 | Kurosawa et al. |
| 9,170,599 B2 | 10/2015 | Ozcan et al. |
| 9,202,835 B2 | 12/2015 | Ozcan |
| 9,254,500 B2 | 2/2016 | Linnell et al. |
| 9,715,099 B2 | 7/2017 | Ozcan et al. |
| 9,743,909 B1 | 8/2017 | Sapozhnikov et al. |
| 9,772,281 B2 | 9/2017 | Bertaux |
| 9,933,351 B2 | 4/2018 | Kent et al. |
| 9,952,191 B2 | 4/2018 | Crisp |
| 10,066,985 B2 | 9/2018 | Stephen |
| 10,281,371 B2 | 5/2019 | Hong |
| 10,317,320 B2 | 6/2019 | David |
| 10,684,209 B1 | 6/2020 | Manautou |
| 10,718,703 B2 | 7/2020 | Pariseau et al. |
| 10,794,810 B1 | 10/2020 | Brown et al. |
| 10,816,445 B2 | 10/2020 | Kelly et al. |
| 10,876,949 B2 | 12/2020 | Brown et al. |
| 11,221,288 B2 | 1/2022 | Brown et al. |
| 11,835,432 B2 * | 12/2023 | McBrady ........... G01N 15/1433 |
| 2002/0124664 A1 | 9/2002 | Call et al. |
| 2003/0142310 A1 | 7/2003 | Bedard et al. |
| 2004/0011975 A1 | 1/2004 | Nicoli et al. |
| 2004/0237671 A1 | 12/2004 | Ryan |
| 2005/0106739 A1 | 5/2005 | Cabuz et al. |
| 2005/0214745 A1 | 9/2005 | Ryan |
| 2005/0255001 A1 | 11/2005 | Padmanabhan et al. |
| 2006/0073585 A1 | 4/2006 | Mcdevitt et al. |
| 2006/0234621 A1 | 10/2006 | Desrochers et al. |
| 2007/0035738 A1 | 2/2007 | Bordelon |
| 2007/0159627 A1 | 7/2007 | Johnson |
| 2007/0247718 A1 | 10/2007 | Yoshikawa et al. |
| 2008/0048874 A1 | 2/2008 | Northrup et al. |
| 2008/0221812 A1 | 9/2008 | Pittaro et al. |
| 2008/0233636 A1 | 9/2008 | Ryan |
| 2009/0027674 A1 | 1/2009 | Laudo |
| 2009/0063078 A1 | 3/2009 | Chandler et al. |
| 2009/0066934 A1 | 3/2009 | Gao et al. |
| 2009/0097124 A1 | 4/2009 | Lundgren |
| 2009/0128810 A1 | 5/2009 | Bates |
| 2009/0219530 A1 | 9/2009 | Mitchell et al. |
| 2010/0101301 A1 | 4/2010 | Mcbrady et al. |
| 2011/0031394 A1 | 2/2011 | Knowles et al. |
| 2011/0136165 A1 | 6/2011 | Vojnovic et al. |
| 2011/0286884 A1 | 11/2011 | Eickhoff et al. |
| 2012/0096925 A1 | 4/2012 | Hansen et al. |
| 2012/0135510 A1 | 5/2012 | Gordon et al. |
| 2012/0255375 A1 | 10/2012 | Kwok et al. |
| 2012/0312072 A1 | 12/2012 | Stringham et al. |
| 2012/0315666 A1 | 12/2012 | Fujioka et al. |
| 2013/0220034 A1 | 8/2013 | Peters et al. |
| 2013/0280752 A1 | 10/2013 | Ozcan et al. |
| 2013/0293873 A1 | 11/2013 | Bentien |
| 2014/0123730 A1 | 5/2014 | Yamasaki et al. |
| 2014/0146157 A1 | 5/2014 | Duplisea et al. |
| 2014/0234865 A1 | 8/2014 | Gabriel |
| 2014/0268105 A1 | 9/2014 | Bills et al. |
| 2015/0099272 A1 | 4/2015 | Hwang et al. |
| 2015/0143929 A1 | 5/2015 | Volckens et al. |
| 2015/0177143 A1 | 6/2015 | Fujita et al. |
| 2015/0186842 A1 | 7/2015 | Daniarov |
| 2015/0260617 A1 | 9/2015 | Ketcham et al. |
| 2015/0323941 A1 | 11/2015 | Pariseau et al. |
| 2015/0355000 A1 | 12/2015 | Bates et al. |
| 2015/0355084 A1 | 12/2015 | White |
| 2016/0223435 A1 | 8/2016 | Takenaka et al. |
| 2016/0290912 A1 | 10/2016 | Kent et al. |
| 2016/0290916 A1 | 10/2016 | Ben et al. |
| 2017/0016824 A1 | 1/2017 | Tucker et al. |
| 2017/0123114 A1 | 5/2017 | Stephen |
| 2017/0219464 A1 | 8/2017 | Houghton et al. |
| 2017/0242234 A1 | 8/2017 | Ashcroft et al. |
| 2017/0370809 A1 | 12/2017 | Miller-Lionberg et al. |
| 2018/0052425 A1 | 2/2018 | Ozcan et al. |
| 2018/0054425 A1 | 2/2018 | Abbott |
| 2018/0088020 A1 | 3/2018 | Couderc |
| 2018/0168490 A1 | 6/2018 | Jones et al. |
| 2018/0258469 A1 | 9/2018 | Johnson-Buck et al. |
| 2018/0259429 A1 | 9/2018 | Adams |
| 2018/0321126 A1 | 11/2018 | Manautou et al. |
| 2019/0095586 A1 | 3/2019 | Mcbrady et al. |
| 2019/0265153 A1 | 8/2019 | Rottenberg |
| 2019/0293539 A1 | 9/2019 | Manautou et al. |
| 2019/0294108 A1 | 9/2019 | Ozcan et al. |
| 2019/0331581 A1 | 10/2019 | Ikehata et al. |
| 2019/0336050 A1 | 11/2019 | Deck et al. |
| 2019/0346356 A1 | 11/2019 | Karnik et al. |
| 2020/0103328 A1 | 4/2020 | Ozcan et al. |
| 2020/0110018 A1 | 4/2020 | Ryadinskiy et al. |
| 2020/0240894 A1 | 7/2020 | Isaacman-Vanwertz et al. |
| 2020/0340901 A1 | 10/2020 | Ozcan et al. |
| 2020/0353166 A1 | 11/2020 | Brown et al. |
| 2021/0116339 A1 | 4/2021 | Nishikawa et al. |
| 2021/0164878 A1 | 6/2021 | Brown et al. |
| 2021/0223155 A1 | 7/2021 | Brown et al. |
| 2021/0255014 A1 | 8/2021 | Speldrich et al. |
| 2021/0255080 A1 | 8/2021 | Myers et al. |
| 2021/0255081 A1 | 8/2021 | Myers et al. |
| 2021/0278321 A1 | 9/2021 | Carlson et al. |
| 2022/0065780 A1 | 3/2022 | Myers et al. |
| 2022/0357261 A1 | 11/2022 | Brown et al. |

(56) References Cited

U.S. PATENT DOCUMENTS

FOREIGN PATENT DOCUMENTS

| | | |
|---|---|---|
| CN | 1695771 A | 11/2005 |
| CN | 103270404 A | 8/2013 |
| CN | 103418295 A | 12/2013 |
| CN | 104081200 A | 10/2014 |
| CN | 204073666 U | 1/2015 |
| CN | 105829860 A | 8/2016 |
| CN | 106323825 A | 1/2017 |
| CN | 107208478 A | 9/2017 |
| CN | 107466364 A | 12/2017 |
| CN | 109578599 A | 4/2019 |
| CN | 110402154 A | 11/2019 |
| CN | 110603069 A | 12/2019 |
| CN | 111272639 A | 6/2020 |
| CN | 114127537 A | 3/2022 |
| EP | 2239557 A1 | 10/2010 |
| EP | 2413293 A1 | 2/2012 |
| EP | 1904826 B1 | 2/2019 |
| EP | 3771898 A1 | 2/2021 |
| JP | 06-511554 A | 12/1994 |
| JP | 2003-075353 A | 3/2003 |
| JP | 2005-534946 A | 11/2005 |
| JP | 2007-101331 A | 4/2007 |
| JP | 2009-025191 A | 2/2009 |
| JP | 2010-145310 A | 7/2010 |
| JP | 2011-502256 A | 1/2011 |
| JP | 2011-139656 A | 7/2011 |
| JP | 2014-095571 A | 5/2014 |
| JP | 2019-511707 A | 4/2019 |
| WO | 2006/013573 A2 | 2/2006 |
| WO | 2012/081285 A1 | 6/2012 |
| WO | 2013/118259 A1 | 8/2013 |
| WO | 2014/156797 A1 | 10/2014 |
| WO | 2015/029673 A1 | 3/2015 |
| WO | 2015/049759 A1 | 4/2015 |
| WO | 2016/073745 A2 | 5/2016 |
| WO | 2016/147018 A1 | 9/2016 |
| WO | 2016/201113 A1 | 12/2016 |
| WO | 2017/051180 A1 | 3/2017 |
| WO | 2017/163650 A1 | 9/2017 |
| WO | 2017/196885 A1 | 11/2017 |
| WO | 2017/196995 A1 | 11/2017 |
| WO | 2018/117146 A1 | 6/2018 |
| WO | 2018/165590 A1 | 9/2018 |
| WO | 2018/176060 A1 | 9/2018 |
| WO | 2019/097523 A1 | 5/2019 |
| WO | 2019/165590 A1 | 9/2019 |
| WO | 2019/210375 A1 | 11/2019 |
| WO | 2020/072234 A1 | 4/2020 |
| WO | 2020/160158 A1 | 8/2020 |
| WO | 2021/034948 A1 | 2/2021 |

OTHER PUBLICATIONS

Notice of Allowance received for U.S. Appl. No. 16/790,923, mailed on Nov. 23, 2021, 7 pages.
Notice of Allowance received for U.S. Appl. No. 16/790,924, mailed on Mar. 2, 2022, 14 pages.
Notice of Allowance received for U.S. Appl. No. 17/028,635, mailed on Jan. 14, 2022, 8 pages.
Notice of Allowance received for U.S. Appl. No. 17/247,096, mailed on Feb. 18, 2022, 9 pages.
Office Action for China Application No. 202010341234.8 issued Jan. 4, 2023.
Office Action for CN Application No. 202010341234.8 issued Jan. 1, 2023.
Office Action for U.S. Appl. No. 16/396,524 dated Jun. 1, 2020, 13 pages.
Office Action issued in Chinese Application No. 202010767051.2 on Jan. 6, 2022, 3 pages.
Office Action issued in Chinese Application No. 202010767051.2 on Jul. 27, 2021, 13 pages.
Office Action received for European Application No. 20188262.8, mailed on Oct. 7, 2021, 6 pages.
Requirement for Restriction/Election Mailed on Apr. 7, 2023 for U.S. Appl. No. 17/247,096, 8 page(s).
Requirement for Restriction/Election Mailed on Sep. 30, 2022 for U.S. Appl. No. 17/314,420.
Sampling Cassettes & Supplies, [online], [retrieved Nov. 3, 2020] <URL:https://www.emssales.net/cassettes-supplies.html> (5 pages).
Schneider et al., Fast Particle Characterization Using Digital Holography and Neural Networks, 2016, [online article] [retrieved on Mar. 25, 2020] retrieved from the Internet URL: https://www.ncbi.nlm.nih.gov/pubmed/26835632, 7 pages.
Unpublished U.S. Appl. No. 62/837,066, filed Apr. 22, 2019, entitled "System and Method For Deep Learning-Based Color Holographic Microscopy".
Unpublished U.S. Application No. 62/838,149, filed Apr. 24, 2019, entitled "Label-Free Bio-Aerosol Sensing Using Mobile Microscopy and Deep Learning".
Wallace, J. Kent, et al., "Robust, compact implementation of an off-axis digital holographic microscope", Optics Express, Jun. 29, 2015, pp. 17367-17378. vol. 23, No. 13.
Wu et al. Label-Free Bioaerosol Sensing Using Mobile Microscopy and Deep Learning, , [article, online], 2018, [retrieved Nov. 8, 2018], URL: https://pubs.acs.org/doi/10.1021/acsphotonics.8b01109, 11 pages.
Wu et al., Label-Free Bioaerosol Sensing Using Mobile Microscopy and Deep Learning, [article, online], 2018, [retrieved Jul. 25, 2019], <URL: https://www.semanticscholar.org/paper/Label-Free-Bioaerosol-Sensing-Using-Mobile-and-Deep-Wu-Calis/fff5dc6d661ab985c3d14ec04fb84907d7750ab7>, 16 pages.
Communication about intention to grant a European patent Mailed on Mar. 7, 2024 for EP Application No. 21204589, 6 page(s).
European search report and search opinion Mailed on Mar. 11, 2024 for EP Application No. 23215872, 13 page(s).
JP Decision to Grant Mailed on Mar. 1, 2024 for JP Application No. 2022180787, 5 page(s).
JP Office Action Mailed on Feb. 26, 2024 for JP Application No. 2021137874, 12 page(s).
CN Office Action, including Search Report Mailed on Nov. 4, 2023 for CN Application No. 202110187527, 6 page(s).
English Translation of CN Office Action dated Nov. 4, 2023 for CN Application No. 202110187527, 1 page(s).
English translation of CN Search report dated Nov. 4, 2023 for CN Application No. 202110187527, 3 page(s).
Non-Final Rejection Mailed on Nov. 27, 2023 for U.S. Appl. No. 17/314,420, 9 page(s).
Notice of Allowance and Fees Due (PTOL-85) Mailed on Nov. 22, 2023 for U.S. Appl. No. 17/247,096, 10 page(s).
Notice of Allowance and Fees Due (PTOL-85) Mailed on Apr. 15, 2022 for U.S. Appl. No. 17/028,635.
Notice of Allowance and Fees Due (PTOL-85) Mailed on Apr. 15, 2022 for U.S. Appl. No. 17/028,635, 4 page(s).
Notice of Allowance and Fees Due (PTOL-85) Mailed on Apr. 19, 2023 for U.S. Appl. No. 17/805,072, 11 page(s).
Notice of Allowance and Fees Due (PTOL-85) Mailed on Apr. 20, 2022 for U.S. Appl. No. 16/790,923, 2 page(s).
Notice of Allowance and Fees Due (PTOL-85) Mailed on Apr. 6, 2022 for U.S. Appl. No. 17/247,096.
Notice of Allowance and Fees Due (PTOL-85) Mailed on Aug. 10, 2023 for U.S. Appl. No. 17/410,682, 8 page(s).
Notice of Allowance and Fees Due (PTOL-85) Mailed on Aug. 14, 2023 for U.S. Appl. No. 17/805,072, 2 page(s).
Notice of Allowance and Fees Due (PTOL-85) Mailed on Aug. 17, 2023 for U.S. Appl. No. 17/805,072, 2 page(s).
Notice of Allowance and Fees Due (PTOL-85) Mailed on Aug. 18, 2021 for U.S. Appl. No. 16/790,918.
Notice of Allowance and Fees Due (PTOL-85) Mailed on Aug. 18, 2023 for U.S. Appl. No. 17/080,344, 2 page(s).
Notice of Allowance and Fees Due (PTOL-85) Mailed on Aug. 23, 2023 for U.S. Appl. No. 17/410,682, 3 page(s).
Notice of Allowance and Fees Due (PTOL-85) Mailed on Aug. 24, 2021 for U.S. Appl. No. 16/748,543.

(56) References Cited

OTHER PUBLICATIONS

Notice of Allowance and Fees Due (PTOL-85) Mailed on Aug. 24, 2021 for U.S. Appl. No. 16/748,543, 9 page(s).
Notice of Allowance and Fees Due (PTOL-85) Mailed on Aug. 27, 2021 for U.S. Appl. No. 16/790,923, 2 page(s).
Notice of Allowance and Fees Due (PTOL-85) Mailed on Aug. 28, 2023 for U.S. Appl. No. 17/080,344, 2 page(s).
Notice of Allowance and Fees Due (PTOL-85) Mailed on Aug. 29, 2023 for U.S. Appl. No. 17/805,072, 2 page(s).
Notice of Allowance and Fees Due (PTOL-85) Mailed on Dec. 3, 2021 for U.S. Appl. No. 16/748,543, 2 page(s).
Notice of Allowance and Fees Due (PTOL-85) Mailed on Dec. 3, 2021 for U.S. Appl. No. 16/748,543.
Notice of Allowance and Fees Due (PTOL-85) Mailed on Dec. 30, 2022 for U.S. Appl. No. 17/805,072.
Notice of Allowance and Fees Due (PTOL-85) Mailed on Dec. 30, 2022 for U.S. Appl. No. 17/805,072, 14 page(s).
Notice of Allowance and Fees Due (PTOL-85) Mailed on Feb. 15, 2022 for U.S. Appl. No. 17/028,635, 2 page(s).
Notice of Allowance and Fees Due (PTOL-85) Mailed on Feb. 18, 2022 for U.S. Appl. No. 17/247,096, 9 page(s).
Notice of Allowance and Fees Due (PTOL-85) Mailed on Jan. 14, 2022 for U.S. Appl. No. 17/028,635, 8 page(s).
Notice of Allowance and Fees Due (PTOL-85) Mailed on Jan. 25, 2022 for U.S. Appl. No. 16/790,923.
Notice of Allowance and Fees Due (PTOL-85) Mailed on Jan. 25, 2022 for U.S. Appl. No. 16/790,923, 2 page(s).
Notice of Allowance and Fees Due (PTOL-85) Mailed on Jul. 10, 2023 for U.S. Appl. No. 17/080,344, 6 page(s).
Notice of Allowance and Fees Due (PTOL-85) Mailed on Jul. 13, 2023 for U.S. Appl. No. 17/805,072, 2 page(s).
Notice of Allowance and Fees Due (PTOL-85) Mailed on Jul. 24, 2023 for U.S. Appl. No. 17/080,344, 2 page(s).
Notice of Allowance and Fees Due (PTOL-85) Mailed on Jul. 28, 2023 for U.S. Appl. No. 17/805,072, 2 page(s).
Notice of Allowance and Fees Due (PTOL-85) Mailed on Jun. 2, 2020 for U.S. Appl. No. 16/530,496, 10 page(s).
Notice of Allowance and Fees Due (PTOL-85) Mailed on Jun. 10, 2022 for U.S. Appl. No. 16/790,924, 2 page(s).
Notice of Allowance and Fees Due (PTOL-85) Mailed on Jun. 11, 2021 for U.S. Appl. No. 16/790,918, 7 page(s).
Notice of Allowance and Fees Due (PTOL-85) Mailed on Jun. 11, 2021 for U.S. Appl. No. 16/790,923.
Notice of Allowance and Fees Due (PTOL-85) Mailed on Jun. 11, 2021 for U.S. Appl. No. 16/790,923, 8 page(s).
Notice of Allowance and Fees Due (PTOL-85) Mailed on Jun. 13, 2023 for U.S. Appl. No. 17/410,682, 8 page(s).
Notice of Allowance and Fees Due (PTOL-85) Mailed on Jun. 2, 2020 for U.S. Appl. No. 16/530,496.
Notice of Allowance and Fees Due (PTOL-85) Mailed on Jun. 20, 2023 for U.S. Appl. No. 17/805,072, 10 page(s).
Notice of Allowance and Fees Due (PTOL-85) Mailed on Mar. 2, 2022 for U.S. Appl. No. 16/790,924, 14 page(s).
Notice of Allowance and Fees Due (PTOL-85) Mailed on Nov. 23, 2021 for U.S. Appl. No. 16/790,923, 7 page(s).
Notice of Allowance and Fees Due (PTOL-85) Mailed on Oct. 19, 2023 for U.S. Appl. No. 17/674,325, 9 page(s).
Notice of Allowance and Fees Due (PTOL-85) Mailed on Oct. 24, 2022 for U.S. Appl. No. 17/805,072.
Notice of Allowance and Fees Due (PTOL-85) Mailed on Oct. 24, 2022 for U.S. Appl. No. 17/805,072, 16 page(s).
Notice of Allowance and Fees Due (PTOL-85) Mailed on Sep. 8, 2020 for U.S. Appl. No. 16/396,524.
Notice of Allowance and Fees Due (PTOL-85) Mailed on Sep. 8, 2020 for U.S. Appl. No. 16/396,524, 7 page(s).
Notice of Allowance for US Patent Applicatin No. U.S. Appl. No. 16/530,496 dated Jun. 2, 2020, 25 pages.
Notice of Allowance for U.S. Appl. No. 16/530,496 dated Jun. 2, 2020, 25 pages.
Notice of Allowance received for Chinese Patent Application No. 202010767051.2, mailed on Mar. 17, 2022, 6 pages (2 pages of English Translation and 4 pages of Original Document).
Notice of Allowance received for U.S. Appl. No. 16/748,543, mailed on Aug. 24, 2021, 10 pages.
CN Office Action—Decision of Rejection Mailed on Dec. 11, 2023 for CN Application No. 202010341234, 8 page(s).
English Translation of CN Office Action—Decision of Rejection dated Dec. 11, 2023 for CN Application No. 202010341234, 10 page(s).
Intention to grant Mailed on Dec. 15, 2023 for EP Application No. 21156433, 9 page(s).
Intention to grant Mailed on Feb. 20, 2024 for EP Application No. 21193185, 6 page(s).
Proceedings of the Academic Annual Meeting of the Society of Environmental Science, vol. 3, pp. 2048-2053, Jun. 30, 2012.
JP Office Action Mailed on Dec. 13, 2021 for JP Application No. 2021017841.
JP Office Action Mailed on Dec. 17, 2021 for JP Application No. 2021016701.
JP Office Action Mailed on Dec. 17, 2021 for JP Application No. 2021016701, 4 page(s).
JP Office Action Mailed on Dec. 21, 2021 for JP Application No. 2021017841, 3 page(s).
JP Office Action Mailed on Dec. 21, 2021 for JP Application No. 2021017841.
JP Office Action Mailed on Sep. 30, 2022 for JP Application No. 2021171491, 3 page(s).
JP Office Action w/English translation Mailed on May 18, 2023 for JP Application No. 2022117842, 5 page(s).
JP Search report Mailed on Dec. 13, 2021 for JP Application No. 2021016701, 12 page(s).
JP Search report Mailed on Dec. 13, 2021 for JP Application No. 2021017841, 9 page(s).
List of references cited by examiner Mailed on Apr. 27, 2021 for U.S. Appl. No. 16/748,543.
List of references cited by examiner Mailed on Aug. 24, 2021 for U.S. Appl. No. 16/748,543.
List of references cited by examiner mailed on May 10, 2022 for U.S. Appl. No. 17/247,096.
Millipore: "Millipore Particle Monitoring Guide," 69 pgs. (1998). [Retrieved from the Internet URL: <http://www.millipore.com/publications.nsf/dda0cb48c91c0fb6852567430063b5d6/b76a969e6d73cbd5852568c5006434c9/$FILEIATTKZK5J/AD030.pdf> on Sep. 2, 2002]., Jan. 1, 1998.
Non-Final Office Action issued in U.S. Appl. No. 16/790,918 on Jan. 28, 2021.
Non-Final Office Action issued in U.S. Appl. No. 16/790,923 on Feb. 2, 2021.
Non-Final Office Action Mailed on Apr. 27, 2021 for U.S. Appl. No. 16/748,543.
Non-Final Office Action Mailed on Feb. 2, 2021 for U.S. Appl. No. 16/790,923.
Non-Final Office Action Mailed on Jan. 28, 2021 for U.S. Appl. No. 16/790,918.
Non-Final Office Action Mailed on Jun. 1, 2020 for U.S. Appl. No. 16/396,524.
Non-Final Office Action Mailed on May 10, 2022 for U.S. Appl. No. 17/247,096.
Non-Final Office Action Mailed on Nov. 4, 2021 for U.S. Appl. No. 17/247,096.
Non-Final Office Action Mailed on Oct. 14, 2022 for U.S. Appl. No. 17/247,096.
Non-Final Office Action Mailed on Oct. 26, 2022 for U.S. Appl. No. 17/410,682.
Non-Final Office Action received for U.S. Appl. No. 16/790,924, mailed on Sep. 30, 2021, 18 pages.
Non-Final Office Action received for U.S. Appl. No. 17/028,635, mailed on Sep. 15, 2021, 13 pages.
Non-Final Office Action received for U.S. Appl. No. 17/247,096, mailed on Nov. 4, 2021, 14 pages.
Non-Final Rejection Mailed on Apr. 27, 2021 for U.S. Appl. No. 16/748,543, 13 page(s).

(56) References Cited

OTHER PUBLICATIONS

Non-Final Rejection Mailed on Feb. 2, 2021 for U.S. Appl. No. 16/790,923.
Non-Final Rejection Mailed on Feb. 2, 2021 for U.S. Appl. No. 16/790,923, 27 page(s).
Non-Final Rejection Mailed on Jan. 23, 2023 for U.S. Appl. No. 17/314,420.
Non-Final Rejection Mailed on Jan. 28, 2021 for U.S. Appl. No. 16/790,918, 14 page(s).
Non-Final Rejection Mailed on Jul. 17, 2023 for U.S. Appl. No. 17/247,096, 8 page(s).
Non-Final Rejection Mailed on Jun. 1, 2020 for U.S. Appl. No. 16/396,524.
Non-Final Rejection Mailed on Jun. 1, 2020 for U.S. Appl. No. 16/396,524, 11 page(s).
Non-Final Rejection Mailed on Mar. 16, 2023 for U.S. Appl. No. 17/080,344, 11 page(s).
Non-Final Rejection Mailed on May 10, 2022 for U.S. Appl. No. 17/247,096, 8 page(s).
Non-Final Rejection Mailed on Nov. 4, 2021 for U.S. Appl. No. 17/247,096, 12 page(s).
Non-Final Rejection Mailed on Oct. 14, 2022 for U.S. Appl. No. 17/247,096, 14 page(s).
Non-Final Rejection Mailed on Oct. 26, 2022 for U.S. Appl. No. 17/410,682, 7 page(s).
Non-Final Rejection Mailed on Sep. 6, 2023 for U.S. Appl. No. 17/314,420, 10 page(s).
Non-Final Rejection Mailed on Sep. 6, 2023 for U.S. Appl. No. 17/674,325, 15 page(s).
Non-Final Rejection Mailed on Sep. 15, 2021 for U.S. Appl. No. 17/028,635, 12 page(s).
Non-Final Rejection Mailed on Sep. 30, 2021 for U.S. Appl. No. 16/790,924.
Non-Final Rejection Mailed on Sep. 30, 2021 for U.S. Appl. No. 16/790,924, 17 page(s).
Notice of Allowance (PTOL-37) Mailed on Jun. 11, 2021 for U.S. Appl. No. 16/790,923.
Notice of Allowance and Fees Due (PTOL-85) Mailed on Apr. 6, 2022 for U.S. Appl. No. 17/247,096, 4 page(s).
Notice of Allowance and Fees Due (PTOL-85) Mailed on Apr. 13, 2022 for U.S. Appl. No. 16/790,923, 2 page(s).
Notice of Allowance and Fees Due (PTOL-85) Mailed on Apr. 15, 2022 for U.S. Appl. No. 16/790,924, 2 page(s).
European Search Report and Search Opinion Received for EP Application No. 21156433.1, mailed on Jul. 14, 2021, 7 pages.
European search report Mailed on Dec. 8, 2020 for EP Application No. 20188262.
European search report Mailed on Dec. 8, 2020 for EP Application No. 20188262, 2 page(s).
European search report Mailed on Dec. 8, 2020 for EP Application No. 20188262.8, 2 pages.
European search report Mailed on Jan. 12, 2023 for EP Application No. 22169769, 15 page(s).
European search report Mailed on Jan. 14, 2022 for EP Application No. 21193185, 10 page(s).
European Search Report Mailed on Jan. 14, 2022for EP Application No. 21193185.2, 10 page(s).
European search report Mailed on Jul. 14, 2021 for EP Application No. 21156433, 7 page(s).
European Search Report Mailed on Jul. 14, 2021 for EP Application No. 21156433.1, 7 page(s).
European search report Mailed on Jul. 19, 2021 for EP Application No. 21155330, 11 page(s).
European search report Mailed on Jul. 21, 2023 for EP Application No. 23160818, 11 page(s).
European search report Mailed on Jul. 26, 2021 for EP Application No. 21151236, 14 page(s).
European Search Report Mailed on Jul. 26, 2021for EP Application No. 21151236.3, 14 page(s).
European Search Report Mailed on Jul. 9, 2021 for EP Application No. 21154848.2, 14 page(s).
European Search Report Mailed on Mar. 3, 2022 for EP Application No. 21195550, 9 page(s).
European Search Report Mailed on Mar. 14, 2022for EP Application No. 21200821.
European search report Mailed on Mar. 22, 2022 for EP Application No. 21204589, 10 page(s).
European Search Report Mailed on Mar. 22, 2022for EP Application No. 21204589.2, 10 page(s).
European search report Mailed on Oct. 10, 2022 for EP Application No. 22169769, 18 page(s).
European Search Report Mailed on Oct. 18, 2022for EP Application No. 22183226.
European search report Mailed on Sep. 10, 2020 for EP Application No. 20170458, 2 page(s).
European Search Report Mailed on Sep. 10, 2020for EP Application No. 20170458.2, 8 page(s).
Examiner Interview Summary Record (PTOL-413) Mailed on Apr. 27, 2021 for U.S. Appl. No. 16/748,543.
Examiner Interview Summary Record (PTOL-413) Mailed on Apr. 27, 2021 for U.S. Appl. No. 16/748,543, 1 page(s).
Examiner Interview Summary Record (PTOL-413) Mailed on Jul. 17, 2023 for U.S. Appl. No. 17/247,096, 1 page(s).
Examiner Interview Summary Record (PTOL-413) Mailed on Jul. 24, 2023 for U.S. Appl. No. 17/314,420, 1 page(s).
Examiner Interview Summary Record (PTOL-413) Mailed on Oct. 24, 2022 for U.S. Appl. No. 17/805,072, 1 page(s).
Extended European Search Report for Patent Application No. 20170458.2 dated Sep. 10, 2020, 8 pages.
Extended European Search Report issued in European Application No. 20188262.8 on Dec. 8, 2020, 5 pages.
Extended European Search Report issued in European Application No. 21151236.3 on Jul. 26, 2021, 14 pages.
Extended European Search Report issued in European Application No. 21156433.1 on Jul. 14, 2021, 7 pages.
Extended European Search Report Mailed on Jan. 14, 2022 for EP Application No. 21193185.2, 10 pages.
Final Office Action Mailed on Mar. 3, 2023 for U.S. Appl. No. 17/247,096.
Final Rejection Mailed on Apr. 11, 2023 for U.S. Appl. No. 17/410,682, 9 page(s).
Final Rejection Mailed on Mar. 3, 2023 for U.S. Appl. No. 17/247,096, 8 page(s).
Final Rejection Mailed on May 15, 2023 for U.S. Appl. No. 17/314,420, 11 page(s).
HPM Series Particulate Matter Sensors, [article, online], 2019, [retrieved Jul. 25, 2019] <URL: https://sensing.honeywell.com/sensors/particulate-sensors/hpm-series, 11 pages.
Intention to grant Mailed on Jul. 25, 2023 for EP Application No. 21154848, 9 page(s).
Intention to grant Mailed on May 4, 2023 for EP Application No. 20188262, 17 page(s).
JP Decision to Grant Mailed on Apr. 22, 2022 for JP Application No. 2021016701.
JP Decision to Grant Mailed on Apr. 22, 2022 for JP Application No. 2021016701, 3 page(s).
JP Decision to grant Mailed on Sep. 10, 2021 for JP Application No. 2020-129927, 5 page(s).
JP Notice of Allowance Mailed on May 16, 2023 for JP Application No. 2022113697, 3 page(s).
JP Notice of Allowance, including Search Report Mailed on May 16, 2023 for JP Application No. 2022113697, 3 page(s).
JP Notice of Allowance, including Search Report Mailed on May 28, 2023 for JP Application No. 2021171491, 3 page(s).
JP Office Action Mailed on Apr. 19, 2022 for JP Application No. 2021017841, 2 page(s).
CN Office Action, including Search Report Mailed on Nov. 15, 2023 for CN Application No. 202110188303, 7 page(s).
CN Office Action, including Search Report Mailed on Nov. 20, 2023 for CN Application No. 202110080239, 5 page(s).
CN Office Action, including Search Report Mailed on Oct. 13, 2023 for CN Application No. 202110188035, 10 page(s).

(56) References Cited

OTHER PUBLICATIONS

Decision to grant a European patent Mailed on Dec. 8, 2023 for EP Application No. 21154848, 2 page(s).
English Translation of CN Office Action dated Nov. 15, 2023 for CN Application No. 202110188303, 4 page(s).
English Translation of CN Office Action dated Oct. 13, 2023 for CN Application No. 202110188035, 6 page(s).
English Translation of CN Office Action, including Search Report dated Nov. 20, 2023 for CN Application No. 202110080239, 5 page(s).
English translation of CN Search report dated Nov. 15, 2023 for CN Application No. 202110188303, 2 page(s).
English translation of CN Search report dated Oct. 13, 2023 for CN Application No. 202110188035, 3 page(s).
English translation of JP Decision to Grant dated Oct. 17, 2023 for JP Application No. 2022117842, 3 page(s).
English Translation of JP Office Action dated Sep. 20, 2023 for JP Application No. 2022180787, 3 page(s).
JP Decision to Grant Mailed on Oct. 17, 2023 for JP Application No. 2022117842, 3 page(s).
JP Office Action Mailed on Sep. 20, 2023 for JP Application No. 2022180787, 3 page(s).
Advisory Action (PTOL-303) Mailed on Jul. 24, 2023 for U.S. Appl. No. 17/314,420, 3 page(s).
Air Sampling Filter Cassette Housings, [online], [retrieved Feb. 11, 2020_ <URL: https://www.zefon.com/cassette-housings> (10 pages).
Allergenco-D & Allergenco-D Posi-Track [online], [retrieved Feb. 11, 2020_ <URL: https://www.emssales.net/media/wysiwyg/uploads/ad peer reviewed study.pdf> 9 pages.
Annex to the communication Mailed on Oct. 6, 2021 for EP Application No. 20188262, 3 page(s).
CN Notice of Allowance Mailed on Mar. 17, 2022 for CN Application No. 202010767051, 4 page(s).
CN Notification to Grant Mailed on Mar. 17, 2022 for CN Application No. 202010767051.2, 6 page(s).
CN Office Action Mailed on Jan. 4, 2023 for CN Application No. 202010341234, 8 page(s).
CN Office Action Mailed on Jan. 6, 2022 for CN Application No. 202010767051.2, 3 page(s).
CN Office Action Mailed on Jul. 7, 2023 for CN Application No. 202010341234, 6 page(s).
CN Office Action Mailed on Jul. 27, 2021 for CN Application No. 202010341234, 10 page(s).
CN Office Action, including Search Report, Mailed on Jul. 27, 2021 for CN Application No. 202010767051.2, 13 page(s).
CN Search report Mailed on Aug. 3, 2020 for CN Application No. 202010767051, 2 page(s).
CN Search report Mailed on Jul. 19, 2021 for CN Application No. 202010341234, 2 page(s).
Communication about intention to grant a European patent received for European Application No. 20170458.2, mailed on Oct. 12, 2022, 6 pages.
Communication Pursuant to Article 94(3) issued in European Application No. 20188262.8 on Oct. 7, 2021, 6 pages.
Decision to grant a European patent Mailed on Feb. 23, 2023 for EP Application No. 20170458, 2 page(s).
Decision to grant a European patent Mailed on Sep. 7, 2023 for EP Application No. 20188262, 2 page(s).
Decision to Grant issued in Japanese Application No. 2020-129927 on Sep. 10, 2021, 5 pages.
English translation for Office Action for CN Application No. 202010341234.8 issued Jan. 4, 2023.
English translation of CN Notice of Allowance dated Mar. 17, 2022 for CN Application No. 202010767051, 2 page(s).
English Translation of CN Office Action dated Jan. 4, 2023 for CN Application No. 202010341234, 10 page(s).
English Translation of CN Office Action dated Jul. 7, 2023 for CN Application No. 202010341234, 10 page(s).
English Translation of CN Office Action dated Jul. 27, 2021 for CN Application No. 202010341234, 7 page(s).
English Translation of CN Office Action dated Jul. 27, 2021 for CN Application No. 202010767051, 7 page(s).
English Translation of CN Office Action Mailed on Jan. 6, 2022 for CN Application No. 202010767051.2, 5 page(s).
English Translation of CN Office Action Mailed on Jul. 27, 2021 for CN Application No. 202010341234.
English translation of JP Decision to Grant dated Apr. 22, 2022 for JP Application No. 2021016701, 2 page(s).
English translation of JP Decision to Grant Mailed on Apr. 22, 2022 for JP Application No. 2021016701.
English Translation of JP Office Action dated Apr. 19, 2022 for JP Application No. 2021017841, 2 page(s).
English Translation of JP Office Action dated Dec. 17, 2021 for JP Application No. 2021016701, 3 page(s).
English Translation of JP Office Action dated Dec. 21, 2021 for JP Application No. 2021017841, 2 page(s).
English Translation of JP Office Action Mailed on Apr. 19, 2022 for JP Application No. 2021017841.
English translation of JP Office Action Mailed on Dec. 13, 2021 for JP Application No. 2021017841.
English Translation of JP Office Action Mailed on Dec. 21, 2021 for JP Application No. 2021017841.
English translation of JP Search report dated Dec. 13, 2021 for JP Application No. 2021016701, 14 page(s).
English translation of JP Search report dated Dec. 13, 2021 for JP Application No. 2021017841, 11 page(s).
English translation of JP Search report Mailed on Dec. 13, 2021 for JP Application No. 2021016701.
EP Office Action Mailed on Jul. 19, 2023 for EP Application No. 21151236, 8 page(s).
EP Office Action Mailed on Jul. 19, 2023 for EP Application No. 21155330, 7 page(s).
EP Office Action Mailed on Oct. 7, 2021 for EP Application No. 20188262, 6 page(s).
European search opinion Mailed on Dec. 8, 2020 for EP Application No. 20188262, 1 page(s).
European search opinion Mailed on Dec. 8, 2020 for EP Application No. 20188262.8, 1 page.
European search opinion Mailed on Sep. 10, 2020 for EP Application No. 20170458, 4 page(s).
European search report and search opinion Mailed on Jul. 9, 2021 for EP Application No. 21154848, 14 page(s).
European Search Report and Search Opinion Received for EP Application No. 20211654.7, mailed on May 3, 2021, 11 pages.
European Search Report and Search Opinion received for EP Application No. 21151236.3, mailed on Jul. 26, 2021, 14 pages.
European Search Report and Search Opinion Received for EP Application No. 21154848.2, mailed on Jul. 9, 2021, 14 pages.
European Search Report and Search Opinion Received for EP Application No. 21155330.0, mailed on Jul. 19, 2021, 11 pages.
CN Notice of Allowance Mailed on May 13, 2024 for CN Application No. 202110188035, 3 page(s).
Notice of Allowance and Fees Due (PTOL-85) Mailed on Aug. 13, 2024 for U.S. Appl. No. 17/674,325, 7 page (s).
CN Office Action, including Search Report Mailed on Jul. 20, 2024 for CN Application No. 202110080239, 6 page(s).
Decision to grant a European patent Mailed on Jul. 11, 2024 for EP Application No. 21204589, 2 page(s).
Decision to grant a European patent Mailed on Jun. 13, 2024 for EP Application No. 21193185, 2 page(s).
English Translation of CN Office Action, including Search Report dated Jul. 20, 2024 for CN Application No. 202110080239, 6 page(s).
English Translation of JP Office Action dated Jul. 11, 2024 for JP Application No. 2023130726, 2 page(s).
English Translation of JP Office Action dated Jun. 3, 2024 for JP Application No. 2021137874, 3 page(s).
JP Office Action Mailed on Jul. 11, 2024 for JP Application No. 2023130726, 2 page(s).
JP Office Action Mailed on Jun. 3, 2024 for JP Application No. 2021137874, 3 page(s).
CN Notice of Allowance Mailed on Apr. 10, 2024 for CN Application No. 202110187527, 2 page(s).

(56) References Cited

OTHER PUBLICATIONS

English translation of CN Notice of Allowance dated Apr. 10, 2024 for CN Application No. 202110187527, 3 page(s).
Non-Final Rejection Mailed on Apr. 22, 2024 for U.S. Appl. No. 17/674,325, 10 page(s).
Notice of Allowance and Fees Due (PTOL-85) Mailed on Apr. 15, 2024 for U.S. Appl. No. 18/471,167, 14 page(s).
Non-Final Rejection Mailed on Jul. 1, 2024 for U.S. Appl. No. 17/805,072, 17 page(s).
CN Office Action, including Search Report Mailed on Aug. 23, 2024 for CN Application No. 202110188303, 6 page(s).
English Translation of CN Office Action dated Aug. 23, 2024 for CN Application No. 202110188303, 4 page(s).
English translation of CN Search report dated Aug. 23, 2024 for CN Application No. 202110188303, 2 page(s).
CN Office Action Mailed on Aug. 28, 2024 for CN Application No. 202010341234, 6 page(s).
English Translation of CN Office Action dated Aug. 28, 2024 for CN Application No. 202010341234, 7 page(s).
English translation of JP Decision to Grant dated Sep. 9, 2024 for JP Application No. 2021137874, 2 page(s).
JP Decision to Grant Mailed on Sep. 9, 2024 for JP Application No. 2021137874, 3 page(s).
Non-Final Rejection Mailed on Sep. 19, 2024 for U.S. Appl. No. 18/471,167, 31 page(s).
Notice of Allowance and Fees Due (PTOL-85) Mailed on Sep. 30, 2024 for U.S. Appl. No. 18/399,419, 10 page(s).
CN Office Action Mailed on Oct. 17, 2024 for CN Application No. 202010341234, 7 page(s).
English Translation of CN Office Action dated Oct. 17, 2024 for CN Application No. 202010341234, 7 page(s).
Extended European Search Report Mailed on Oct. 18, 2024 for EP Application No. 24188454, 5 page(s).
Intention to grant Mailed on Oct. 17, 2024 for EP Application No. 22182866, 8 page(s).
European search report Mailed on Nov. 13, 2024 for EP Application No. 24174131, 10 page(s).
Non-Final Rejection Mailed on Dec. 18, 2024 for U.S. Appl. No. 17/805,072, 30 page(s).
CN Notice of Allowance Mailed on Nov. 29, 2024 for CN Application No. 202110080239, 2 page(s).
English translation of CN Notice of Allowance dated Nov. 29, 2024 for CN Application No. 202110080239, 2 page(s).

* cited by examiner

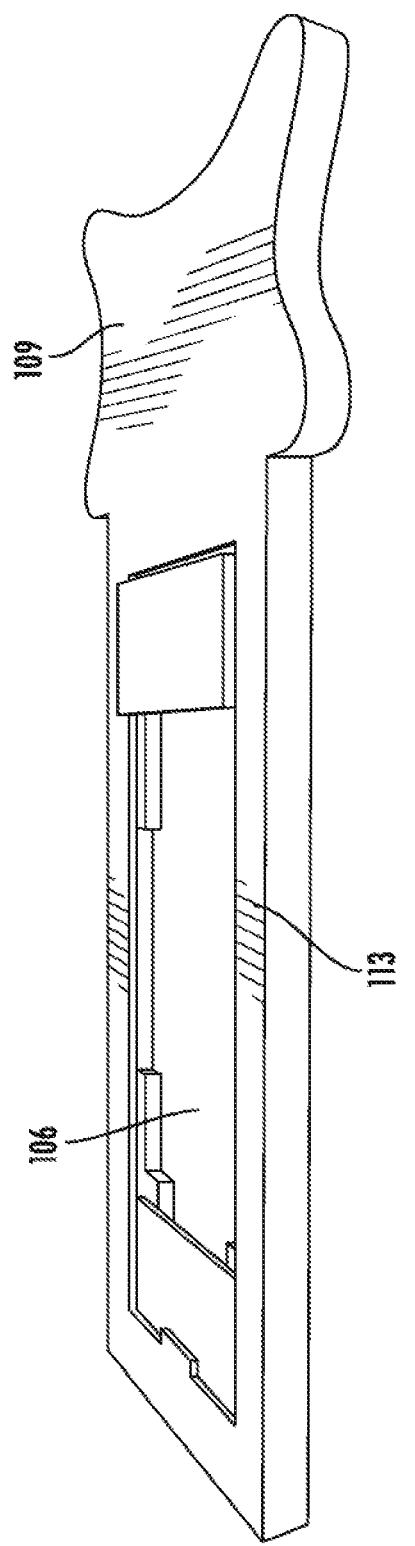

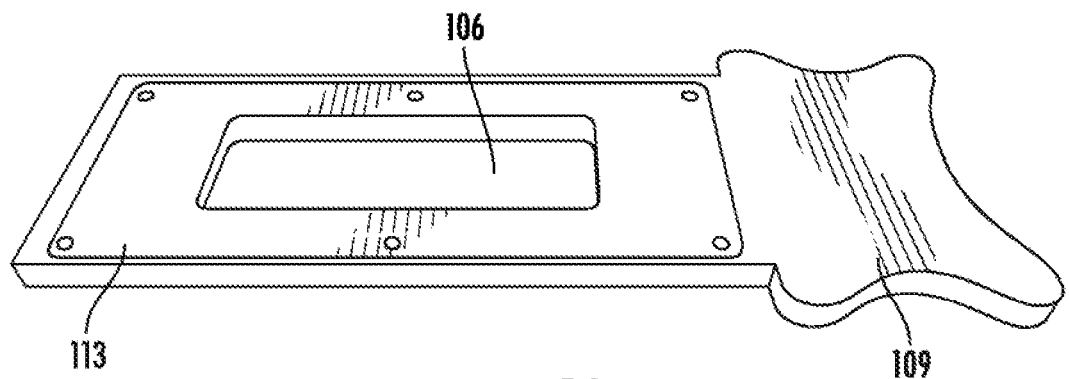
FIG. 8A
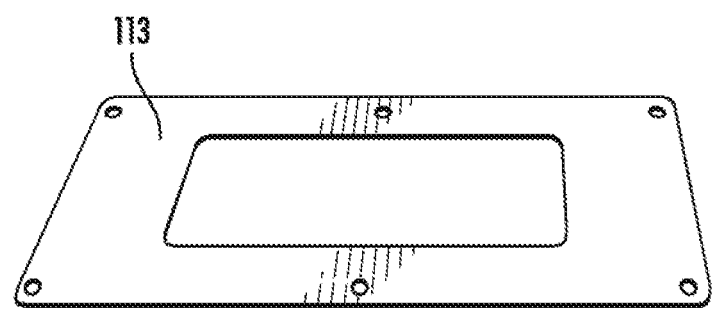
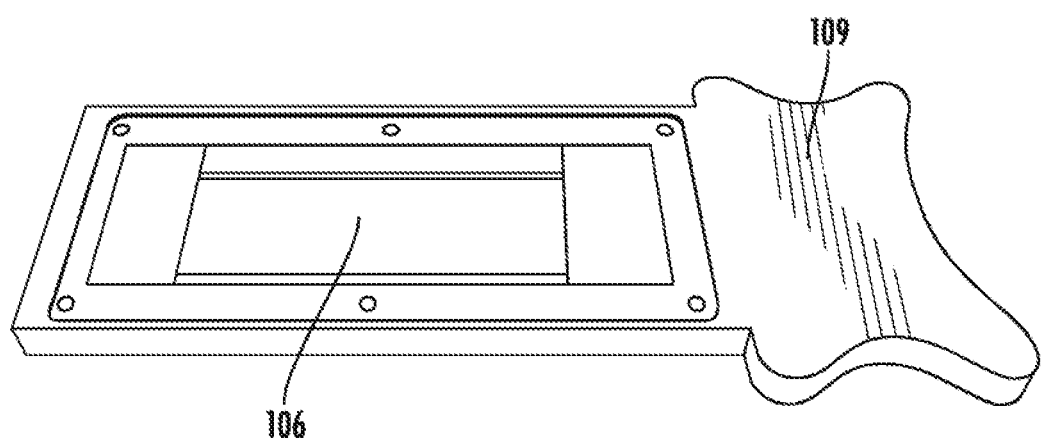
FIG. 8B

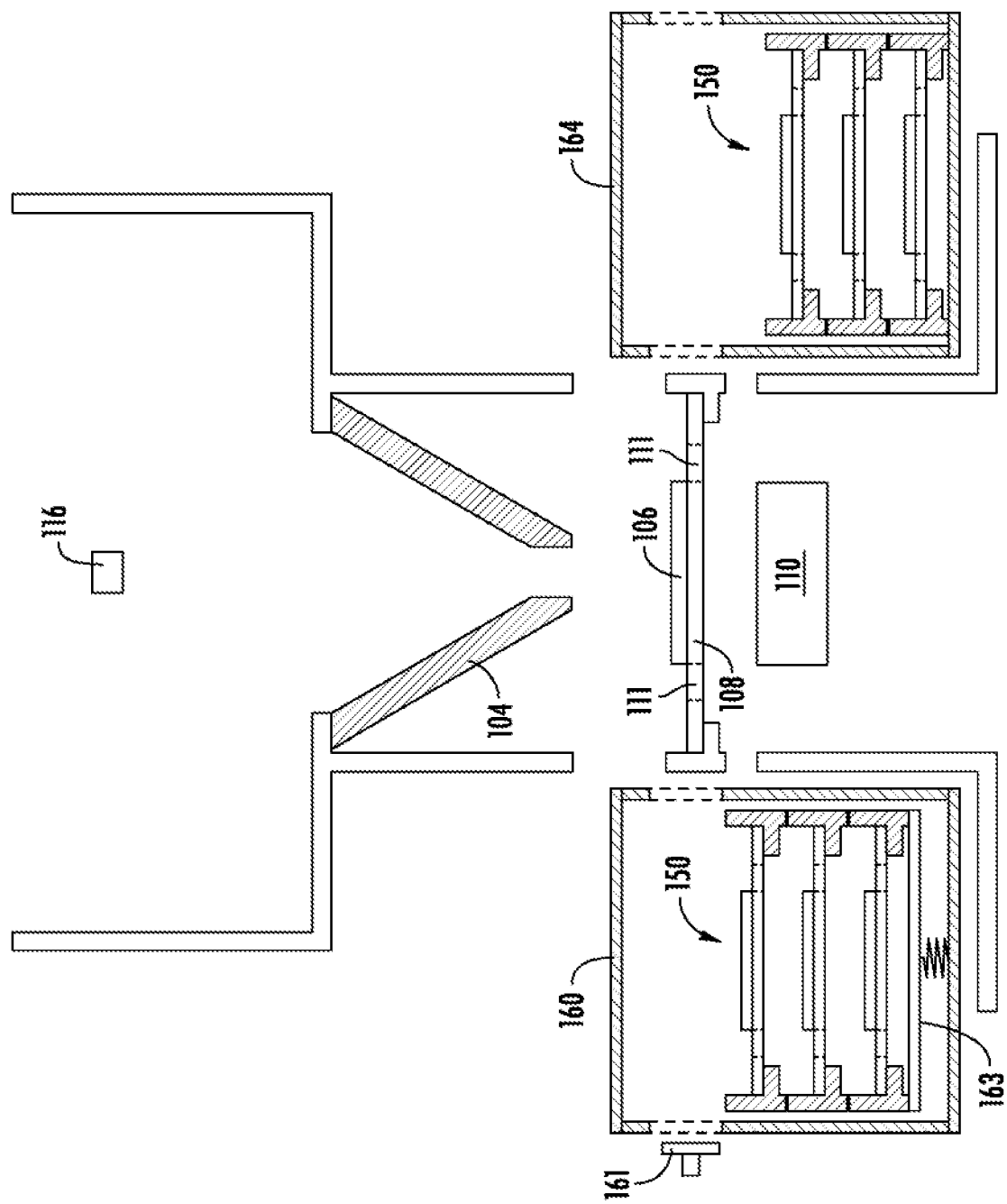

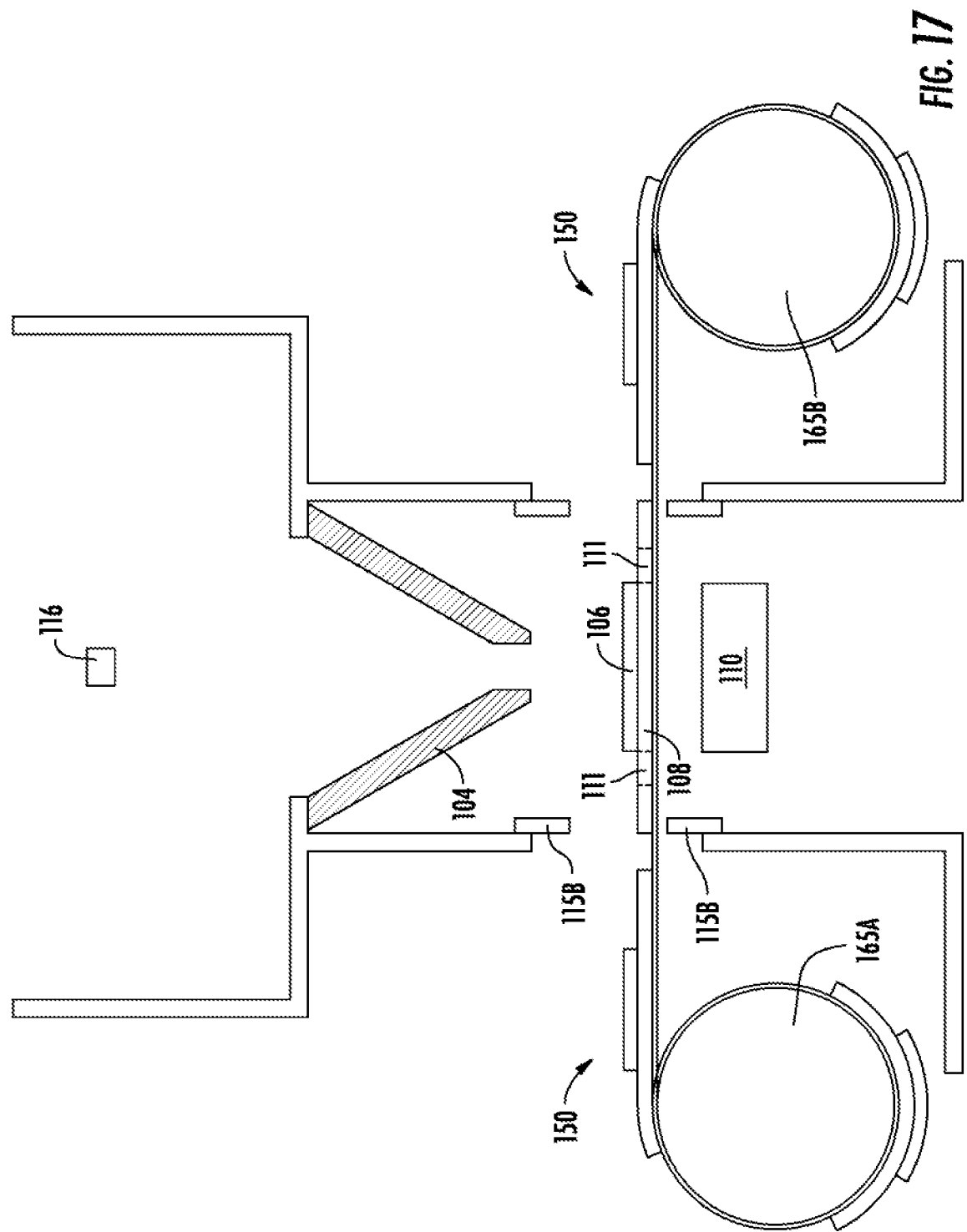

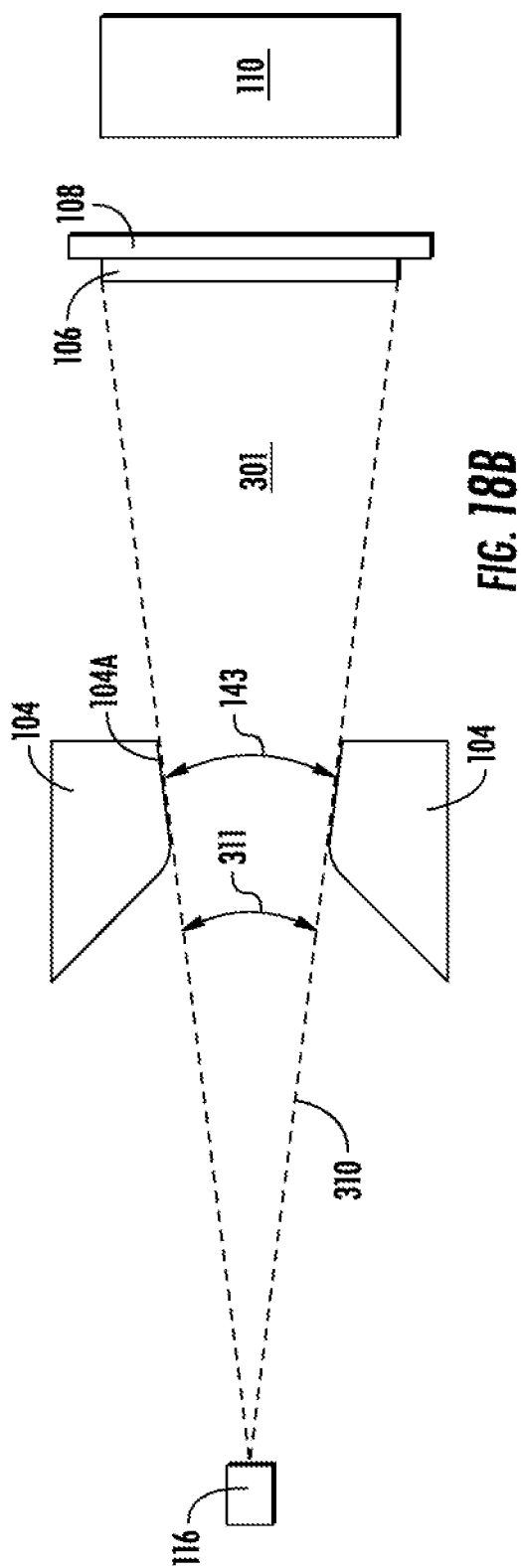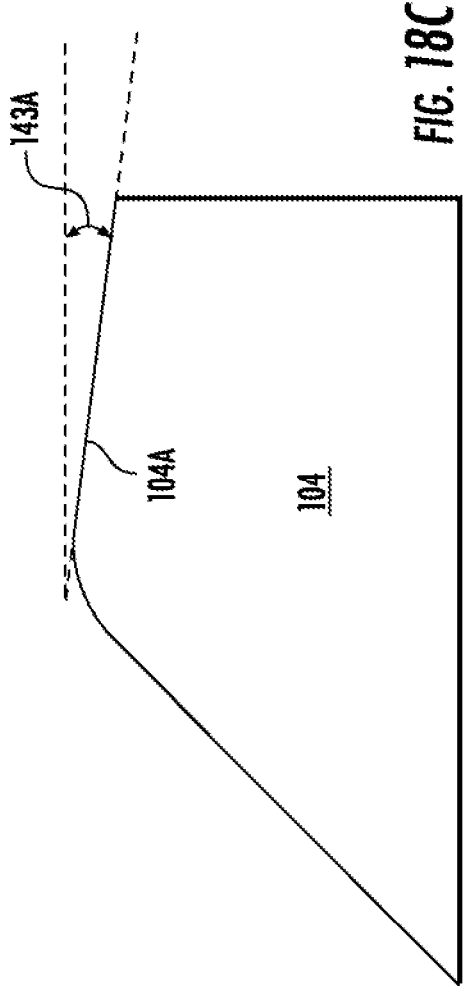

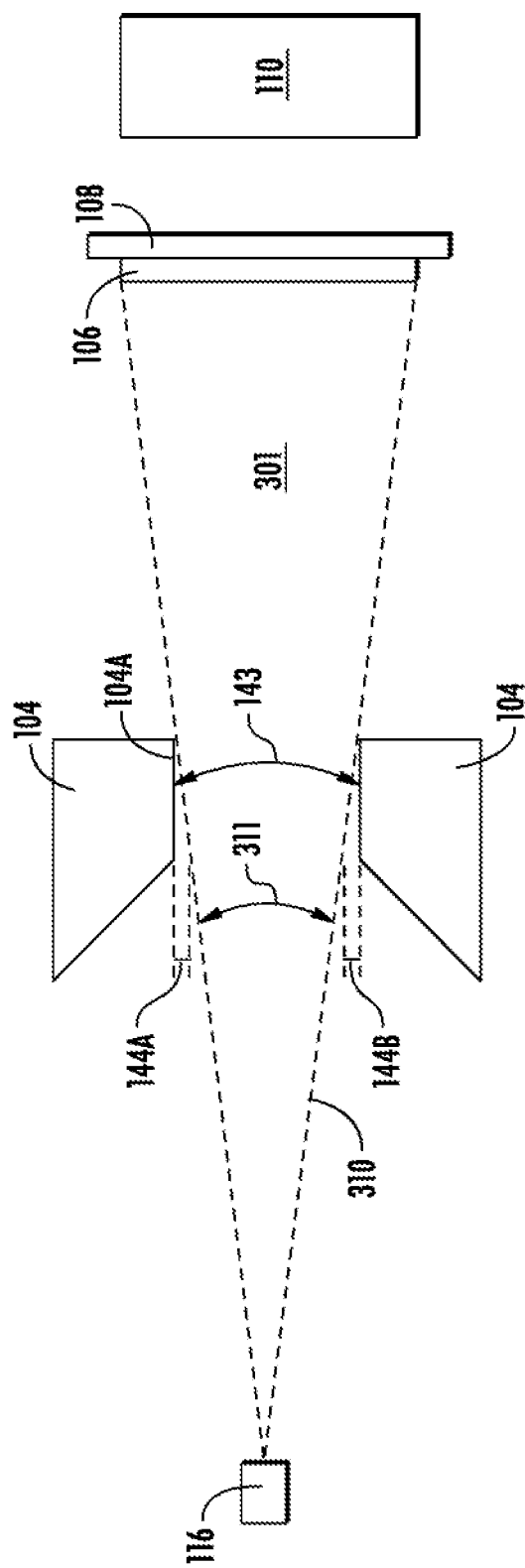

FLUID COMPOSITION SENSOR DEVICE AND METHOD OF USING THE SAME

CROSS REFERENCE TO RELATED APPLICATIONS

The present application is a continuation application of U.S. patent application Ser. No. 17/080,344, filed Oct. 26, 2020, which is hereby incorporated by reference in its entirety.

BACKGROUND

Sensors and devices may be utilized to characterize various aspects of fluids in a wide variety of applications. As just one example, sensor devices may be utilized for monitoring air conditions, such as monitoring and characterizing the particulate content of a flow of air. However, existing fluid sensor devices provide limited functionality in generating data indicative of certain characteristics of fluids, such as the unique identity and concentration of individual particles contained within a fluid flow. Fluid sensor devices can use holographic imaging methods to characterize particle identity and concentration of particulate matter that has been collected via inertial impaction. It is desirable to improve various aspects of particle sampling and analysis. In general, it can be advantageous for a fluid sampling device to utilize a sampling media that enables rapid and/or simplified sequential sampling of particles. For devices utilizing holographic imaging (such as lensless holography) for in situ particle analysis, it is desirable to avoid optical reflections and scattering in order to achieve optimal image quality.

Accordingly, a need exists for an improved fluid sensor devices capable of reducing optical interference from the inertial impactor sampling method and/or enabling multiple samples to be analyzed from one or more impactor collection media.

BRIEF SUMMARY

Various embodiments described herein relate to apparatuses and methods for collecting and characterizing particles suspended within a fluid. Various embodiments are directed to a device for detecting fluid particle characteristics comprising: A device for detecting fluid particle characteristics comprising: a housing configured to support a collection media for capturing one or more particles of a plurality of particles within a volume of fluid passing through at least a portion of the housing; a pump to move the volume of fluid through the at least a portion of the housing and across at least a portion of the collection media; an imaging device configured to capture an image of at least a portion of one or more particles captured by the collection media; and a controller comprising a particle matter mass concentration calculation circuitry configured to determine one or more particle loading conditions of at least a portion of the one or more particles captured by the collection media based at least in part on the image captured by the imaging device, wherein the controller is configured to adjust an operation of the pump based at least in part on at least one of the one or more particle loading conditions of the at least a portion of the one or more particles captured by the collection media.

In various embodiments, the controller may be configured to stop operation of the pump upon the particle matter mass concentration calculation circuitry determines that a predetermined total particle matter mass threshold is reached. In various embodiments, determining the one or more particle loading conditions may comprise determining a first particle loading condition of a first image and determine a second particle loading condition of a second image. In various embodiments, determining the one or more particle loading conditions may comprise comparing the first particle loading condition to the second particle loading condition. In certain embodiments, determining the one or more particle loading conditions may further comprise calculating a difference between the first particle loading condition and the second particle loading condition. In certain embodiments, the particle matter mass concentration calculation circuitry may be configured to stop the pump when a predetermined difference in first particle loading condition and second particle loading condition is calculated.

In various embodiments, the controller may be configured to modify operation of the pump upon the particle matter mass concentration calculation circuitry determining that a predetermined difference in first particle loading condition and second particle loading condition is calculated. In various embodiments, determining the one or more particle loading conditions may comprise identifying one or more particle clusters within the image captured by the imaging device. In various embodiments, the imaging device may be configured to capture images in set time intervals. In various embodiments, the imaging device may be configured to capture an image at a start of a fluid flow of the volume of fluid passing through the at least a portion of the housing. In certain embodiments, determining the one or more particle loading conditions may comprise determining if the start of the fluid flow of the volume of fluid causes a spike in the one or more particle loading condition.

In various embodiments, determining the one or more particle loading conditions may comprise calculating a particle matter mass of at least a portion of the one or more particles captured by the collection media based at least in part on a total intensity of light across the image thereof. In certain embodiments, the controller may be configured to stop operation of the pump upon the particle matter mass concentration calculation circuitry determines that the total intensity of light detected within the image is below a threshold. In certain embodiments, the controller may be configured to adjust the operation of the pump upon the particle matter mass concentration calculation circuitry determining that the total intensity of light detected within the image is below a threshold. In various embodiments, determining the one or more particle loading conditions may comprise determining a volume of fluid that flowed through the at least a portion of the housing over a defined time period. In certain embodiments, the volume of fluid that flowed through the housing over the defined time period may be determined based at least in part on a pump run time and a pump flow rate.

Various embodiments are directed to a method for detecting fluid particle characteristics comprising: directing a flow of the volume of fluid toward a collection media, receiving, by the collection media, one or more particles of a plurality of particles within the volume of fluid; capturing an image of the one or more particles of the plurality of particles received by the collection media; determining one or more particle loading conditions of at least a portion of the one or more particles of the plurality of particles received by the collection media based at least in part on the image thereof; and adjusting the volume of fluid flowing toward the collection media.

In various embodiments, the determining the one or more particle loading conditions may comprise determining a total particle matter mass by a particle matter mass concentration calculation circuitry of a controller configured to adjust the volume of fluid flowing toward the collection media. In various embodiments, the method may further comprise adjusting the volume of fluid flowing toward the collection media upon the particle matter mass concentration calculation circuitry upon detecting at least a threshold difference between a first particle loading condition and a second particle loading condition, wherein the first particle loading condition is determined for a first image and the second particle loading condition is determined for a second image captured after the first image. In various embodiments, the method may further comprise adjusting the volume of fluid flowing toward the collection media upon the particle matter mass concentration calculation circuitry determines that a total intensity of light detected within the image is below a threshold.

BRIEF DESCRIPTION OF THE DRAWINGS

Reference will now be made to the accompanying drawings, which are not necessarily drawn to scale, and wherein:

FIG. 6 illustrates a collection media assembly in accordance with one embodiment as described herein.

FIGS. 8A-8B illustrate various views of a collection media assembly in accordance with one embodiment as described herein.

FIG. 16 illustrates a cross-sectional view of an exemplary apparatus in accordance with one embodiment described herein.

FIG. 17 illustrates a cross-sectional view of an exemplary apparatus in accordance with one embodiment described herein.

FIGS. 18A-18D schematically illustrate exemplary apparatuses in accordance with various embodiments described herein.

DETAILED DESCRIPTION

Figure 1:
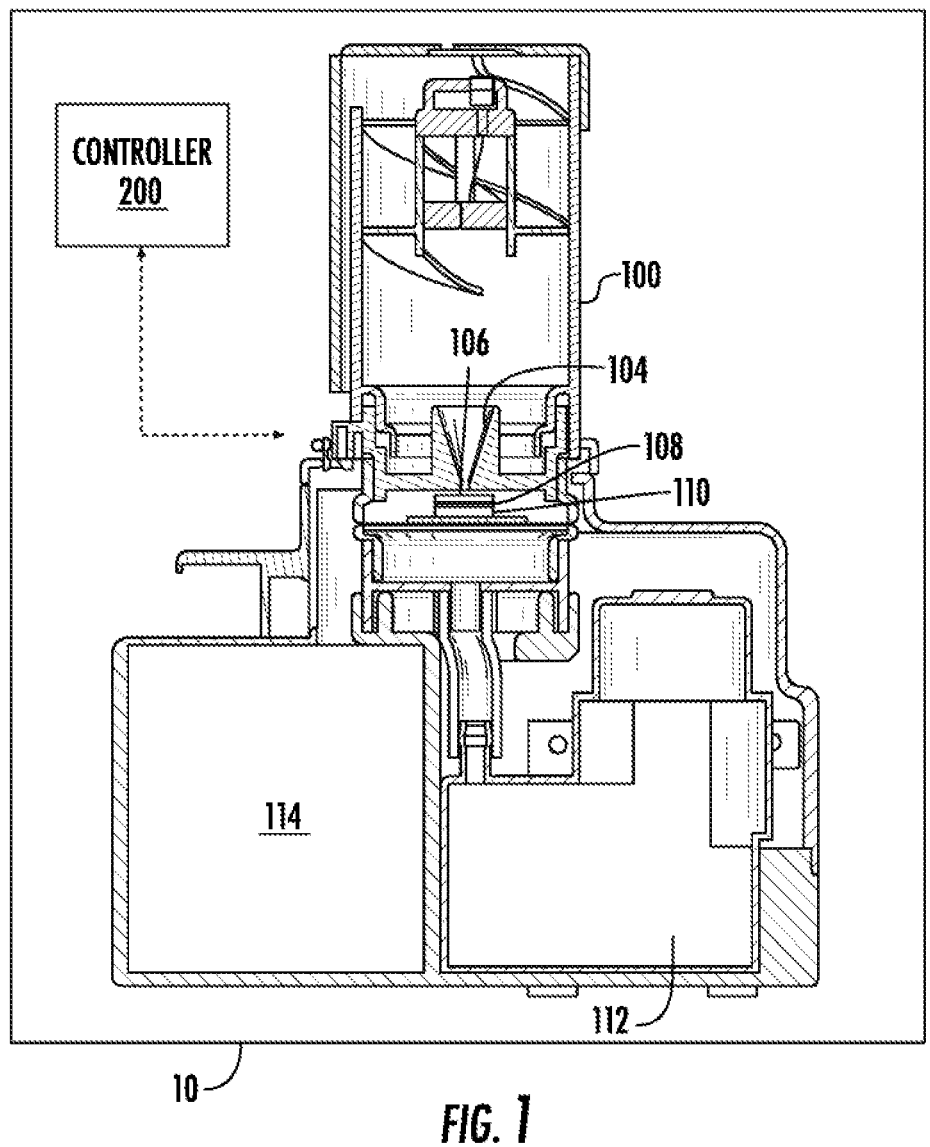
FIG. 1 schematically illustrates an exemplary fluid sensor in accordance with various embodiments.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

The words "example," or "exemplary," when used herein, are intended to mean "serving as an example, instance, or illustration." Any implementation described herein as an "example" or "exemplary embodiment" is not necessarily preferred or advantageous over other implementations. As used herein, a "fluid" may be embodied as a gas, a liquid, or a combination of a gas and a liquid in a single flow. Thus, the term "fluid" encompasses various materials subject to flow, such as, but not limited to, liquids and/or gases (e.g., air, oil, or the like). Thus, various embodiments are directed to fluid sensing systems, such as gas sensing systems (e.g., certain embodiments being specifically configured for operation with air; other embodiments being configured for operation with other gases, such as inert gases, volatile gases, and/or the like), liquid sensing systems, and/or the like.

Overview

Described herein is a device configured to characterize and monitor particulate matter within a volume of fluid. The device discussed herein may be configured to quantify and classify the particles within a volume of fluid based at least in part on the imaging of particles received by a collection media of a fluid composition sensor. Further, the device discussed herein may be configured to characterize the particle composition within the volume of fluid by directly identifying the particle size and particle type of each of the particles received by the collection media of the fluid composition sensor. By directly determining the particle size and particle type, the device as described herein may be configured to detect a change in particle composition within a volume of fluid over time and/or location.

Further, the device described herein may be configured to produce a clear optical output with respect to an image captured by an imaging device of the fluid composition sensor. The device herein may comprise an impactor nozzle configured to minimize the reflection of a portion of a light beam emitted from an illumination source. The device herein may comprise an impactor nozzle configured to minimize imaging distortion caused by a divergent light beam emitted from an illumination source being incident on a sidewall thereof and reflecting toward the imager. For example, by minimizing the scattering of the light beam caused by the impactor nozzle, such a device configuration may reduce noise that may degrade the ability of the fluid composition sensor to locate, identify, and/or analyze individual particles of the one or more particles disposed within the collection media. The device may similarly be configured so as to avoid the degradation of an ability of the fluid composition sensor to reconstruct an image of one or more of the captured particles, which may result in decreased sensor performance with respect to classifying the one or more particles using machine learning.

Further, the device herein may be configured to increase device reliability and user satisfaction associated with the device by utilizing a replaceable collection media in conjunction with a fluid composition sensor. In accordance with certain embodiments discussed herein, the collection media used to collect particles from a volume of fluid within the fluid composition sensor may be automatically replaced (within a fluid collection position) upon a determination that a predefined sample volume of fluid or sample number of particles has passed through the device. The device herein may minimize intermittent user-interaction with the collection media, thereby expediting a sample collection process, reducing the physical work required of a user, facilitating measurement automation, and minimizing device failures caused by misalignment during a user-defined reconfiguration of one or more device components.

In various embodiments, a fluid composition sensor comprising a controller (e.g., particle matter mass concentration calculation circuitry 208) configured to calculate total particle matter mass of a plurality of particles received from within a volume of fluid by a collection media and characterize the spatial arrangement of the plurality of particles so as to identify one or more particle configurations known to negatively affect sensor accuracy and/or sensor effectiveness over time (e.g., lifespan), such as, for example, particle clustering, spiking, particle touching, particles on top of each other, and/or a collection media "covered" by particles, may facilitate the prevention of sensor inaccuracies caused by overloading an exhausted and/or compromised collection media with a particle loading condition that cannot accurately be determined and/or identified by the sensor. Such an exemplary configuration substantially minimizes the amount of retesting required to obtain accurate data and prevents over-use of the fluid composition sensor by defining operational parameters configured to substantially autonomously limit the operation of the sensor upon identifying the presence of one or more of the aforementioned error-inducing particle load conditions. By dynamically monitoring the load condition of the plurality of particles received by the collection media and optimizing the operational parameters so as to selectively limit the run time of the device, the longevity of the device may be increased. Further, the device as described herein may further simplify the calculation of the requisite operational run time of the fluid composition sensor needed to a sample of particles sufficient to provide one or more statistically significant measurements.

Fluid Composition Sensor

The device 10 may comprise a fluid composition sensor 100 configured to receive a volume of fluid flowing therethrough. Specifically, the device 10 may be configured to receive a volume of a gas, such as air, flowing therethrough. In various embodiments, the fluid composition sensor 100 may be further configured to capture an image of one or more particles of a plurality of particles present within the received volume of fluid. As illustrated in FIG. 1, the fluid composition sensor 100 may comprise a housing 101, an impactor nozzle 104, a collection media 106, an at least partially transparent substrate 108, and an imaging device 110. In some embodiments, the fluid composition sensor 100 may further comprise a power supply 114 configured to power the fluid composition sensor 100 and a fan or pump 112 configured to pull the volume of fluid into and through the fluid composition sensor 100. In various embodiments, the fan or pump 112 is calibrated, such that the flow rate of fluid moving through the device is known/determined based at least in part on the operating characteristics (e.g., operating power) of the fan or pump 112. In various embodiments, the fluid composition sensor 100 may comprise a lens free microscope, such as one described in WIPO Publication Number 2018/165590, which is incorporated herein by reference in its entirety. In various embodiments, a lens-free microscope may utilize one or more techniques, such as, for example, lensless holography, to capture a particle image, as described herein, of the one or more particles of a plurality of particles received by a collection media 106. Alternatively, the fluid composition sensor 100 may comprise a lens-based imaging device or any other apparatus configured to capture an image which may be analyzed by an apparatus as described herein so as to determine a particle size or other particle characteristics of one or more particles captured by the collection media 106. In various embodiments, a lens-based imaging device may utilize one or more imaging techniques, such as, for example, optical microscopy, to capture a particle image, as described herein, of the one or more particles of a plurality of particles 120 received by a collection media 106. In various embodiments, optical microscopy may comprise light transmitted through or reflected from a collection media 106 and/or a plurality of particles 120 disposed therein through one or more lenses to magnify and capture an image of one or more of the particles of the plurality of particles 120 within the collection media 106. As described herein, the fluid composition sensor 100 may be electronically and communicatively connected to a controller 200.

Figure 2:
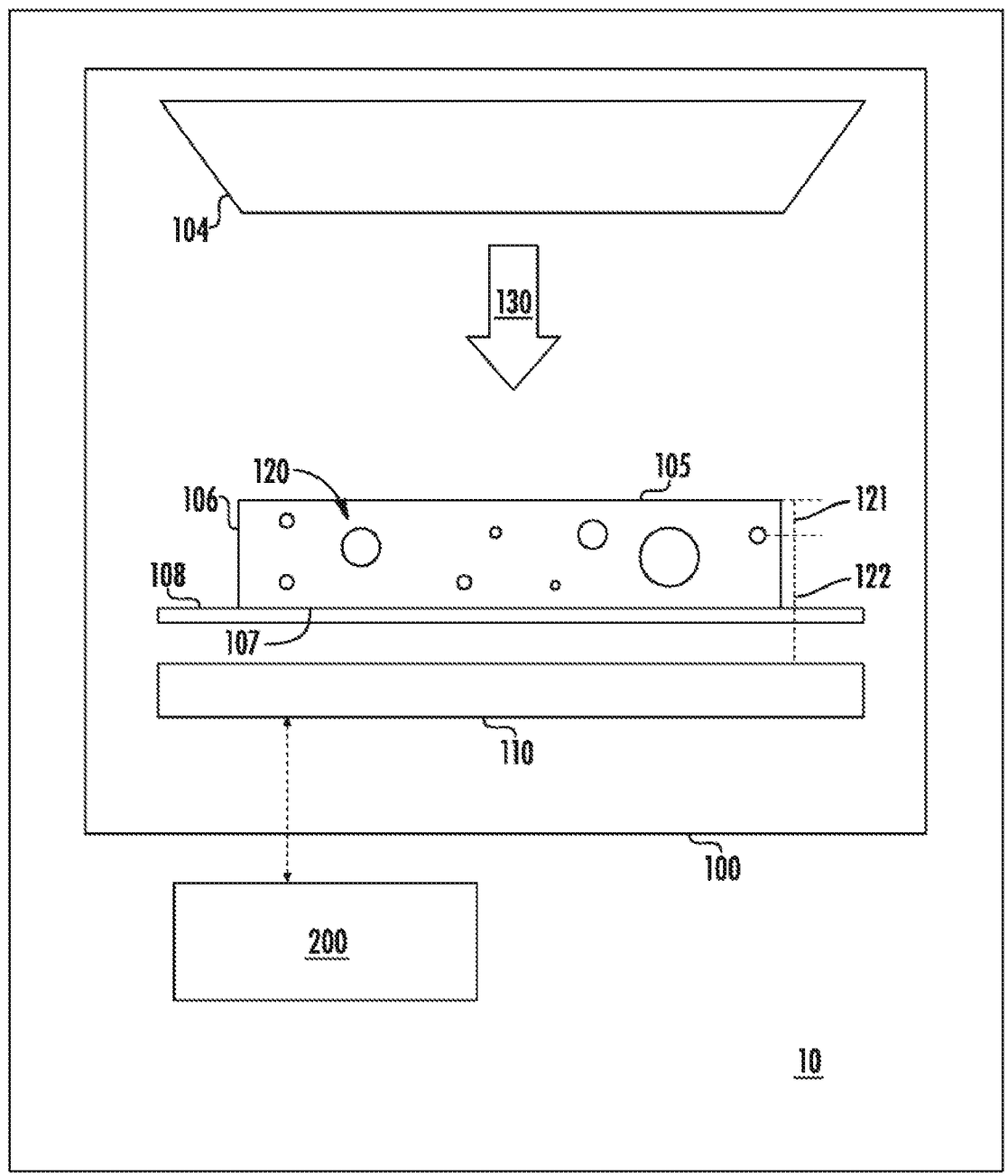
FIG. 2 illustrates a cross-sectional view of a portion of an exemplary fluid sensor as described herein.

In various embodiments, as illustrated in FIGS. 1 and 2, the impactor nozzle 104 may be configured to direct the flow of the volume of fluid received by the fluid composition sensor 100 in a flow direction 130 at least substantially perpendicular to and directed toward a receiving surface of a collection media 106. In various embodiments, the collection media 106 may be embodied as a portion of a collection media assembly. For example, the collection media assembly may be embodied as a replaceable slide (as illustrated in FIGS. 5-8B), within which a replaceable collection media 106 may be disposed. In other embodiments, the entirety of the replaceable slide may be disposable, and the collection media 106 may be permanently secured therein. However, in other embodiments, the collection media assembly may comprise a collection media tape 106 (e.g., the collection media tape may be embodied as an elongated collection media 106 that may be moved through the fluid composition sensor 100 such that a fresh (e.g., unused) portion of the collection media tape may be exposed to the fluid flowing through the impactor nozzle 104). As yet another example, the collection media 106 may be disposed on and/or as a portion of a rotatable disc, such that the collection media 106 may be rotated relative to the fluid composition sensor 100 such that a fresh (e.g., unused) portion of the collection media disc may be exposed to the fluid flowing through the impactor nozzle 104. It should be understood that the collection media 106 may be embodied in any of a variety of forms. In yet other embodiments, the collection media 106 may be permanently affixed within the composition sensor 100, such that the entire composition sensor 100 may be disposable once the collection media 106 is sufficiently filled with particles from a fluid flowing through the composition sensor 100. The collection media 106 may be configured to receive one or more particles of a plurality of particles 120 via interaction with the volume of fluid. In various embodiments, the collection media 106 may comprise a receiving surface 105, a backside 107, and a thickness defined by the distance between the receiving surface 105 and the backside 107. In various embodiments, the thickness of the collection media 106 may be at least substantially between about 10 and about 1000 microns, (e.g., 100 microns). In various embodiments, the collection media 106 may comprise a material suitable to stop one or more particles of a plurality of particles 120 traveling at a velocity into the receiving surface 105 before the particle reaches the backside 107, such that the one or more particles of the plurality of particles 120 are disposed within the collection media at a distance along the thickness of the collection media 106. For example, in various embodiments, the collection media may comprise an adhesive (i.e. sticky) material, such as a gel. In various embodiments, the fluid composition sensor 100 may comprise a transparent substrate 108 positioned at least substantially adjacent (e.g., secured directly to) the backside 107 of the collection media 106. In various embodiments, the collection media assembly may further comprise the transparent substrate 108. Further, in various embodiments, such as those in which the collection media assembly is embodied as a slide, the collection media assembly may comprise a collection media housing 113, which may define a handle 109. In various embodiments, a collection media housing 113 may be configured to receive and secure at least a portion of a collection media 106 and/or a substrate 108. In various embodiments, collection media housing 113 may be configured to be removably positioned at least partially within a fluid composition sensor 100, such the collection media 106 is disposed within a fluid flow path of a volume of fluid traveling in flow direction 130. In various embodiments, the collection media housing 113 may be configured to have at least one opening positioned adjacent at least a portion of the collection media 106 such that the one or more particles of a plurality of particles present within a volume of fluid may engage a receiving surface 105 of the collection media 106.

Figure 5:
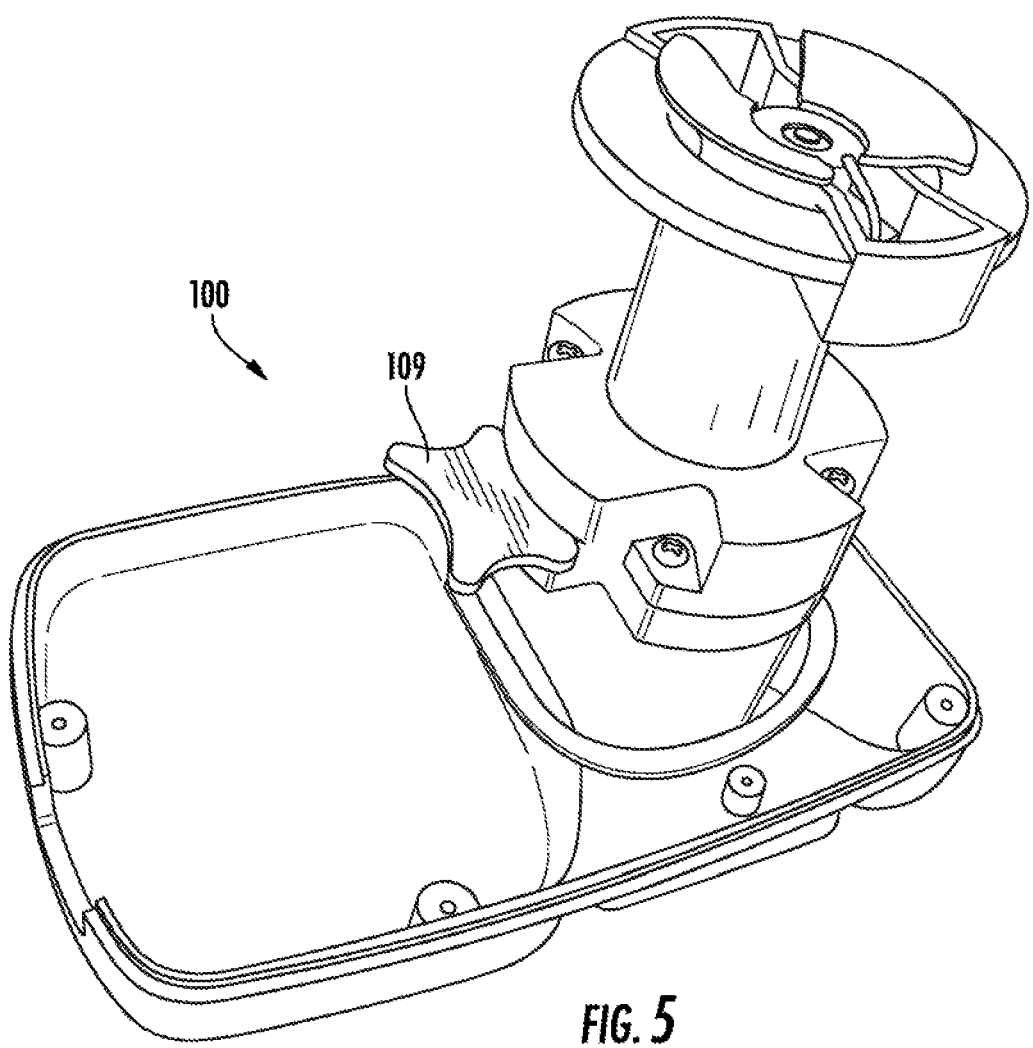
FIG. 5 illustrates an exemplary apparatus in accordance with various embodiments as described herein.

In various embodiments, the collection media housing 113 may define a handle 109. In various embodiments, as shown in FIG. 5, the handle 109 may be configured to facilitate the accessibility of the collection media 106 and/or housing 113, for example, to enable the removal and/or replacement of the collection media 106 from the fluid composition sensor 100. As noted above, the collection media 106 may be configured for use in conjunction with (or embodied as), for example, a slide, a tape, a disc, or any other appropriate mechanism configured to facilitate the transportation of the collection media 106.

In various embodiments, a device 10 may experience increased inaccuracies over time, for example, as the number of particles collected within the collection media 106 increases (and the resulting physical properties of the collection media 106 changes as a result of the increase number of particles disposed therein). Thus, one or more components of the collection media assembly as described herein may be replaceable. In various embodiments, replacing one or more components of the collection media assembly may comprise removing one or more components from the fluid composition sensor 100 and replacing the one or more components of the collection media assembly with one or more at least substantially similar components. Alternatively, it should be understood that in various embodiments, replacing one or more components of the collection media assembly may comprise cleaning, repositioning, and/or modifying the one or more components of the collection media assembly so as to decrease the number of particles present within a portion of the collection media 106 exposed to the air flow within the composition sensor 100. As a non-limiting example, in various embodiments wherein the collection media assembly may comprise an adhesive tape, at least a portion of the tape may be removed so as to expose a fresh portion of tape positioned thereunder and corresponding to the at least a portion of the tape that was removed. As a further non-limiting example, in various embodiments wherein the collection media assembly may comprise a disc, the disc may be configured to be cleaned such that the characteristics of the disc may be at least substantially similar to those of a new disc. In various embodiments, the fluid composition sensor 100 may in part or in whole be configured to be replaceable and/or disposable.

In various embodiments, the fluid composition sensor 100 may comprise an imaging device 110 configured to capture an image of the one or more particles of the plurality of particles 120 received by the collection media 106. In various embodiments, the imaging device 110 may be positioned at least substantially adjacent (e.g., in contact with or spaced a distance away from) the backside 107 of the transparent substrate 108 such that the imaging device 110 may effectively capture one or more images of the one or particles captured within the collection media 106. In various embodiments, the fluid composition sensor 100 may have a designated field of view for capturing, permanently and/or temporarily, an image of multiple particles of the plurality of particles simultaneously. The collection media 106 may reside at least partially within the field of view of the imaging device 110, such that the plurality of particles 120 captured by the collection media 106 are visible by the imaging device 110. As shown in FIG. 2, the imaging device 110 may be positioned beneath the transparent substrate 108 relative to the collection media 106. For example, the imaging device 110 may be positioned between about 100 microns and about 5 mm (e.g., 1 mm) way from the transparent substrate 108. Alternatively, the imaging device 110 may be positioned above the transparent substrate 108 relative to the collection media 106.

In various embodiments, the imaging device 110 may be configured to capture the image of one or more particles of the plurality of particles 120 received by the collection media 106 using one or more imaging techniques such as, for example, lensless holography. In various embodiments wherein the imaging device is configured to utilize lensless holography, the imaging device may computationally produce an image of the one or more particles received by the collection media 106 by digitally reconstructing one or more microscopic images of one or more particles received by the collection media 106 without using a lens. Alternatively, and/or additionally, the imaging device 110 may utilize optical microscopy to capture an image of one or more particles of the plurality of particles 120 received by the collection media 106. For example, in various embodiments, as described herein, an image captured by an exemplary imaging device may comprise a two-dimensional image (e.g., a photograph of at least a portion of the collection media) and/or a three-dimensional image (e.g., a three-dimensional digital reconstruction of at least a portion of the particles captured at the collection media). In some embodiments, the fluid composition sensor 100 may be configured to capture one or more images of a plurality of particles in the collection media 106 simultaneously. For example, the fluid composition sensor 100 may have a designated field of view for capturing, permanently and/or temporarily, an image of multiple particles of the plurality of particles simultaneously, as described herein. In various embodiments, the one or more images captured by the fluid composition sensor 100 may be transmitted at least to the controller 200. In various embodiments, the imaging device 110 may be configured to capture one or more images at a first time and a second time, wherein the first time represents the start of an analysis of the one or more particles of the plurality of particles 120 captured by the collection media 106 by the device 10 and the second time is subsequent the first time. In such a configuration, the device may be able to distinguish between particles present within the collection media 106 at the start of the particle analysis and particles that were newly received by the collection media 106 by comparing the respective particle images captured at the first and second times and identifying any particles from the second captured particle image that were not captured in the first captured particle image.

In various embodiments, the fluid composition sensor 100 may be connected to a power supply 114 configured to receive power and power the fluid composition sensor 100. As non-limiting examples, the power supply 114 may comprise one or more batteries, one or more capacitors, one or more constant power supplies (e.g., a wall-outlet), and/or the like. In some embodiments the power supply 114 may comprise an external power supply positioned outside of the fluid composition sensor 100 and configured to deliver alternating or direct current power to the fluid composition sensor 100. Further, in some embodiments, as illustrated in FIG. 1, the power supply 114 may comprise an internal power supply, for example, one or more batteries, positioned within the fluid composition sensor 100. In various embodiments, a power supply 114 may be connected to the controller 200 to enable distribution of power through the controller 200 to the fluid composition sensor 100.

FIGS. 6-8B show various exemplary embodiments of a collection media assembly as described herein. As shown in FIGS. 6-8B, the collection media assembly may comprise a collection media 106 disposed upon a replaceable slide, a collection media housing 113 configured to secure the replaceable slide—and thus the collection media 106—therein, and a handle 109. In various embodiments, the collection media 106 may be configured to be attached to a transparent substrate 108, which may further be disposed within the collection media housing 113. In various embodiments, the replaceable slide may define the transparent substrate 108. As shown in FIG. 6, the collection media housing 113 may comprise a tab proximate at least a portion of an opening configured to receive the replaceable slide via a hinged connection that enables the replaceable slide to snap into a desired position. The collection media 106 may be configured to be replaceable, as it may be removed from the collection media housing 113 via the unhinging of the replaceable slide from its secured position within the collection media housing 113 and subsequently replaced with a different collection media 106 (e.g., a fresh collection media 106). In various embodiments, the collection media housing 113 may be removed from the fluid composition sensor 100, for example, via user interaction with the handle 109.

Figure 7A:
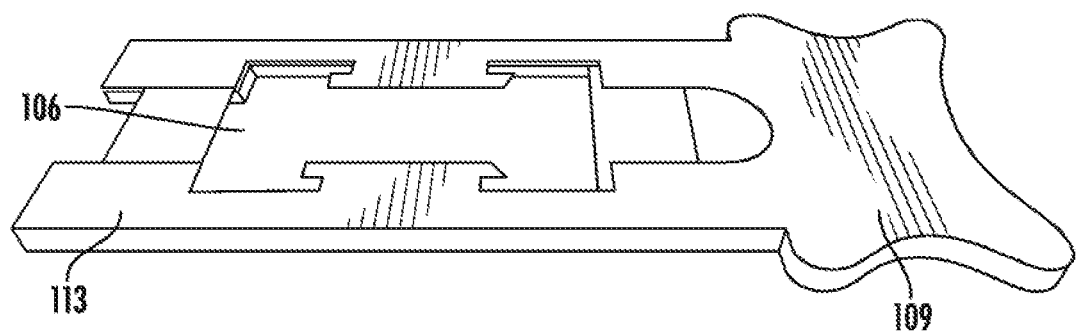
FIGS. 7A-7B illustrate various views of a collection media assembly in accordance with one embodiment as described herein.
Figure 7B:
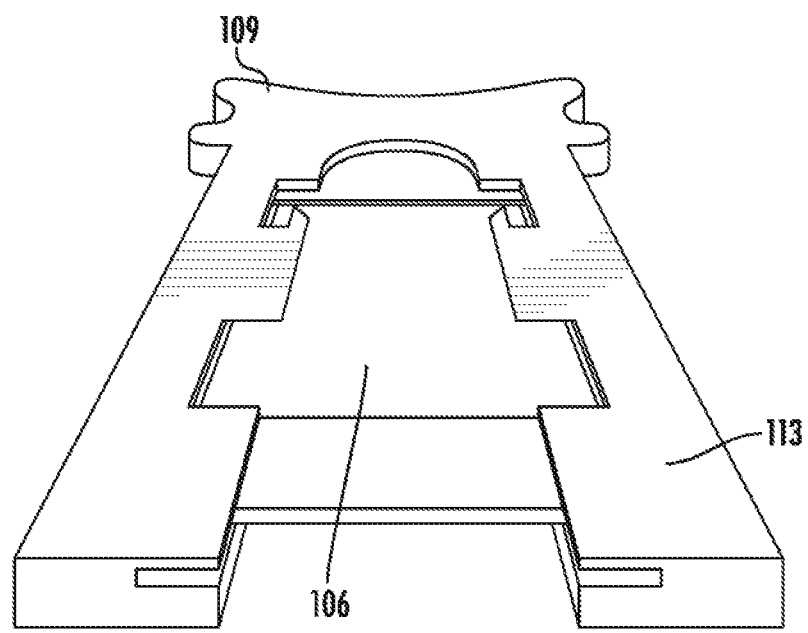

As shown in FIGS. 7A and 7B, the collection media housing 113 may comprise a slot along at least one side with dimensions corresponding to a cross-section of a replaceable slide such that the housing 113 may be configured to receive the replaceable slide with the collection media 106 disposed thereon via the slot. The collection media 106 may be configured to be replaceable, as it may be removed from the collection media housing 113 via the sliding of the replaceable slide from its secured position within the collection media housing 113 through the slot and subsequently replaced with a different collection media 106. The collection media housing 113 may be removed from the fluid composition sensor 100, for example, via user interaction with the handle 109.

As shown in FIGS. 8A and 8B, the collection media housing 113 may comprise a removeable face such that the housing 113 may be configured to receive the replaceable slide when the removable face is in a detached configuration and secure the replaceable slide into a desired position when the removable face is in an assembled configuration. The collection media 106 may be configured to be replaceable, as it may be removed from the collection media housing 113 via the detachment of the removable face of the collection media housing 113 and the recovery of the replaceable slide from its secured position within the collection media housing 113 and subsequently replaced with a different collection media 106. The collection media housing 113 may be removed from the fluid composition sensor 100, for example, via user interaction with the handle 109.

Figure 9A:
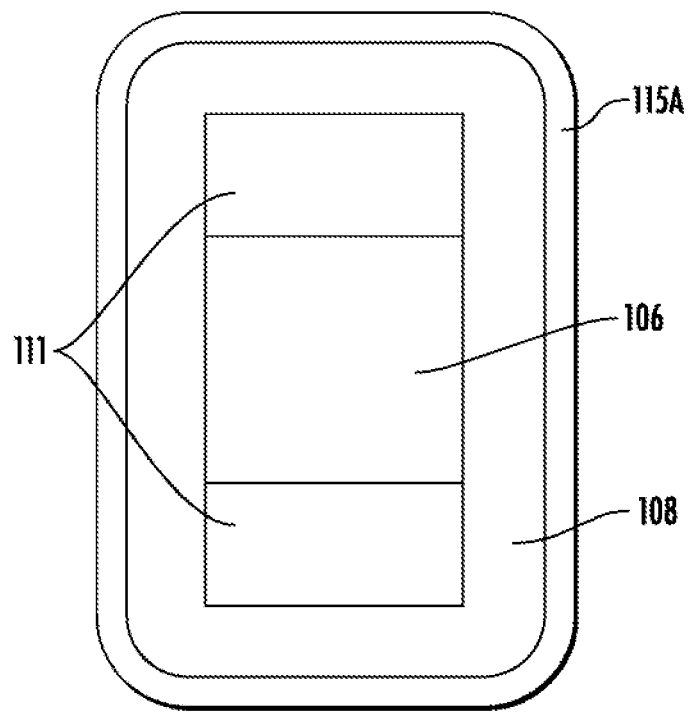
FIGS. 9A-9B illustrate various views of a collection media assembly in accordance with various embodiments described herein.
Figure 9B:
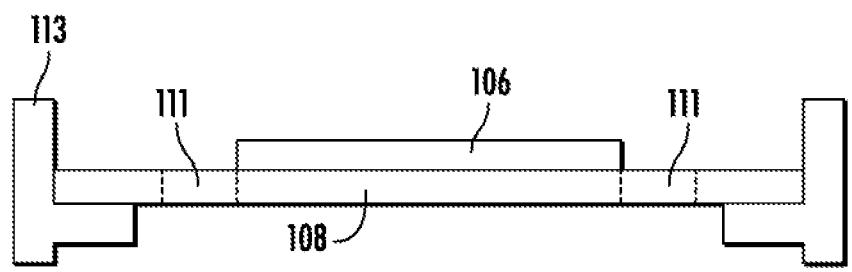

FIGS. 9A-9B illustrate various views of a collection media assembly in accordance with various embodiments as described herein. As shown in FIGS. 9A and 9B, the collection media assembly 150 may comprise at least one collection media 106 disposed upon a transparent substrate 108, at least one orifice 111 extending through the transparent substrate 108, and an air seal engagement portion 115A surrounding the collection media 106, the at least one orifice 111, and the transparent substrate 108. In various embodiments, the transparent substrate 108 may be defined by a replaceable slide, as described herein. In various embodiments, the at least one orifice 111 may be positioned at least approximately adjacent the at least one collection media 106. For example, as illustrated in FIGS. 9A-9B, the at least one orifice 111 may comprise a plurality of orifices (e.g., two orifices disposed on opposite sides of the collection medial 106) disposed about the transparent substrate 108 so as to enable a volume of fluid to flow through the transparent substrate 108. In various embodiments, the air seal engagement portion 115A may define at least a portion of a perimeter of the collection media assembly 150, such as a portion of the collection media assembly 150 that surrounds one of the at least one collection media 106 and the at least one orifice 111 corresponding thereto. In various embodiments, the air seal engagement portion 115A may be used to prevent or limit exposure of adjacent or nearby collection media sections 106 to the fluid being sampled. In certain embodiments, the air seal engagement portion 115A may be embodied as a rigid, at least substantially smooth component configured to interact with a gasket (or other flexible sealing component) of an air seal component of a device as discussed herein. As another example, the air seal engagement portion 115A may comprise one or more flexible components (e.g., a resilient gasket) configured to interact with corresponding components of an air seal component of a device so as to form an at least substantially fluid tight seal therebetween. For example, the air seal engagement portion 115A may be configured to receive and/or engage an air seal component of the fluid composition sensor such that at least substantially all of a volume of fluid flowing through the fluid composition sensor flows through the at least one orifice 111 surrounded by the at least one seal engagement portion 115A. As shown in FIG. 9A, the air seal engagement portion 115A may comprise a portion of a surface of the transparent substrate 108. In various embodiments, as described herein, the air seal engagement portion 115A may comprise a plurality of air seal engagement portions, each corresponding to a respective collection media 106 of the at least one collection media and the at least one orifice 111 corresponding thereto.

FIG. 9B illustrates a cross-sectional view of an exemplary collection media assembly in accordance an embodiment described herein. As shown, the collection media assembly 150 may comprise a collection media housing 113. In various embodiments, the collection media housing 113 may be configured to at least partially surround the transparent substrate 108 so as to embody an outer frame of the collection media assembly 106. In various embodiments, as described herein, the at least one seal engagement portion of the collection media assembly 150 may comprise a portion of the collection media housing 113. In various embodiments, the collection media housing 113 may be configured to facilitate the collective storage (e.g., stacking) and subsequent dispensing of each of a plurality of collection media assemblies 150 into an internal sensor portion of a fluid composition sensor. For example, as described herein, the collection media housing 113 of each of the plurality of collection media assemblies 150 may be configured to receive a force from one or more components of the exemplary device described herein (e.g., an actuator element) such that each collection media assembly 150 may be consecutively transmitted in series from a storage location to the internal sensor portion of the fluid composition sensor.

Figure 10:
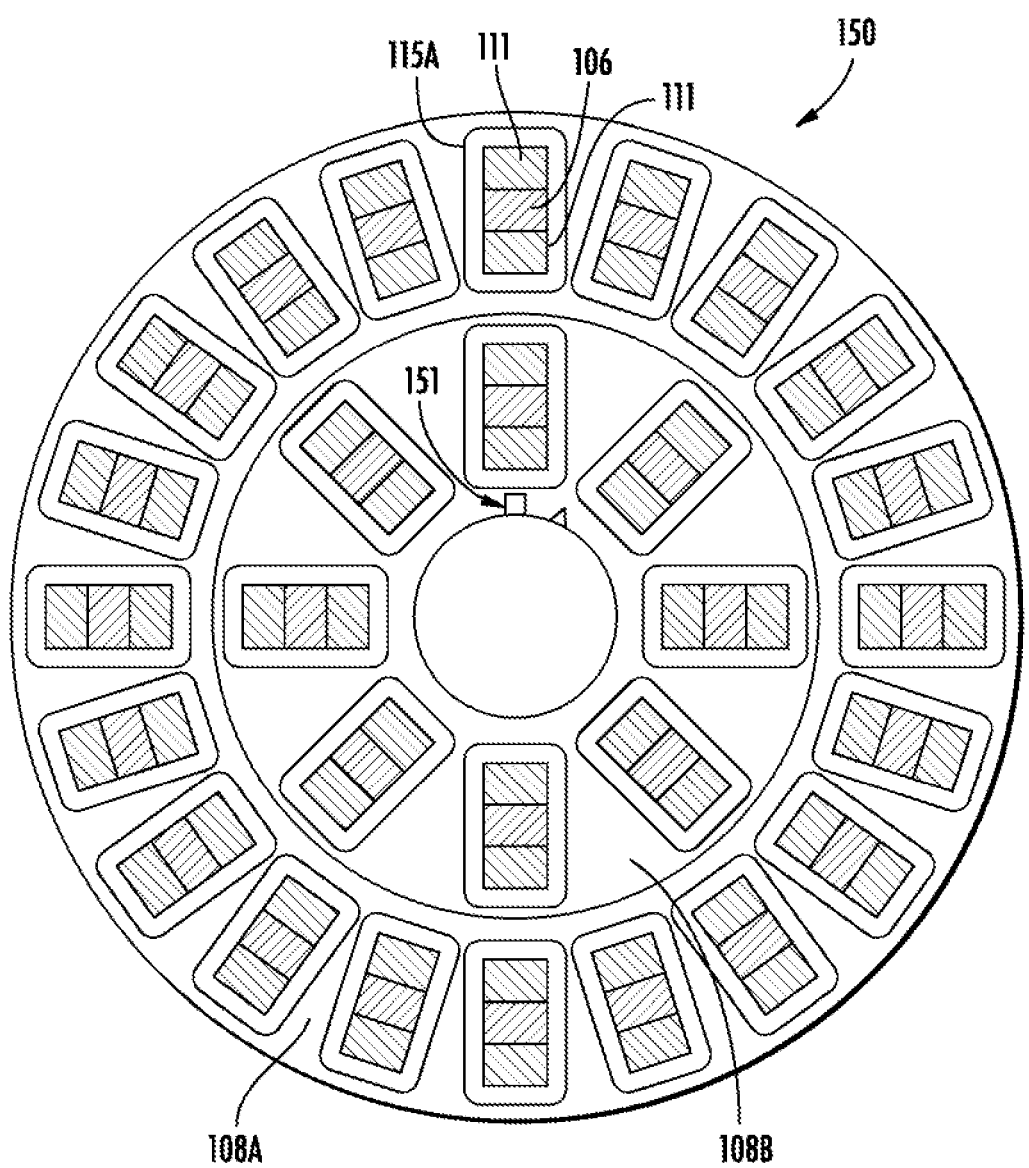
FIG. 10 illustrates a top view of a collection media assembly in accordance with an exemplary embodiment described herein.
Figure 11:
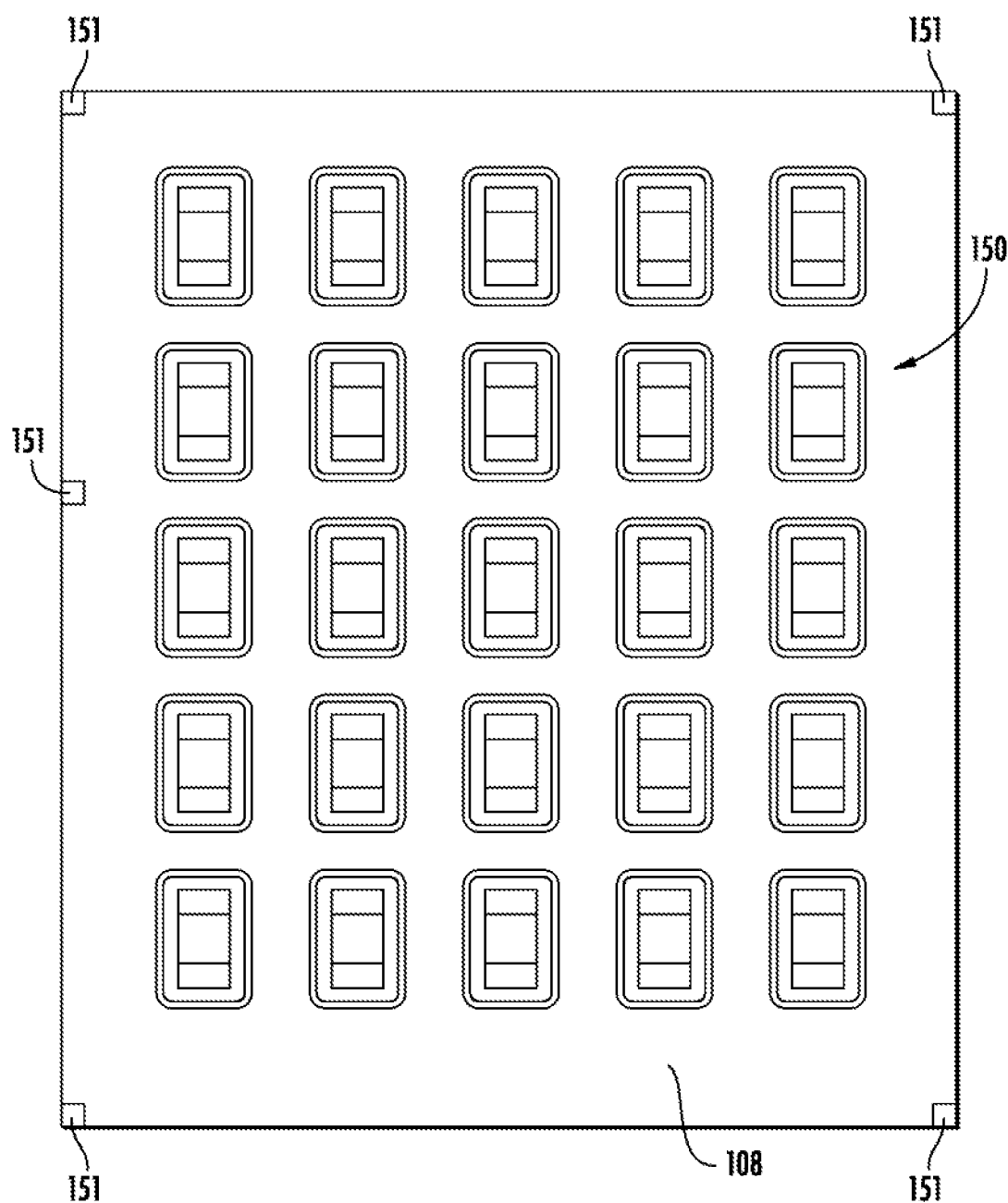
FIG. 11 illustrates a top view of a collection media assembly in accordance with an exemplary embodiment described herein.
Figure 12:
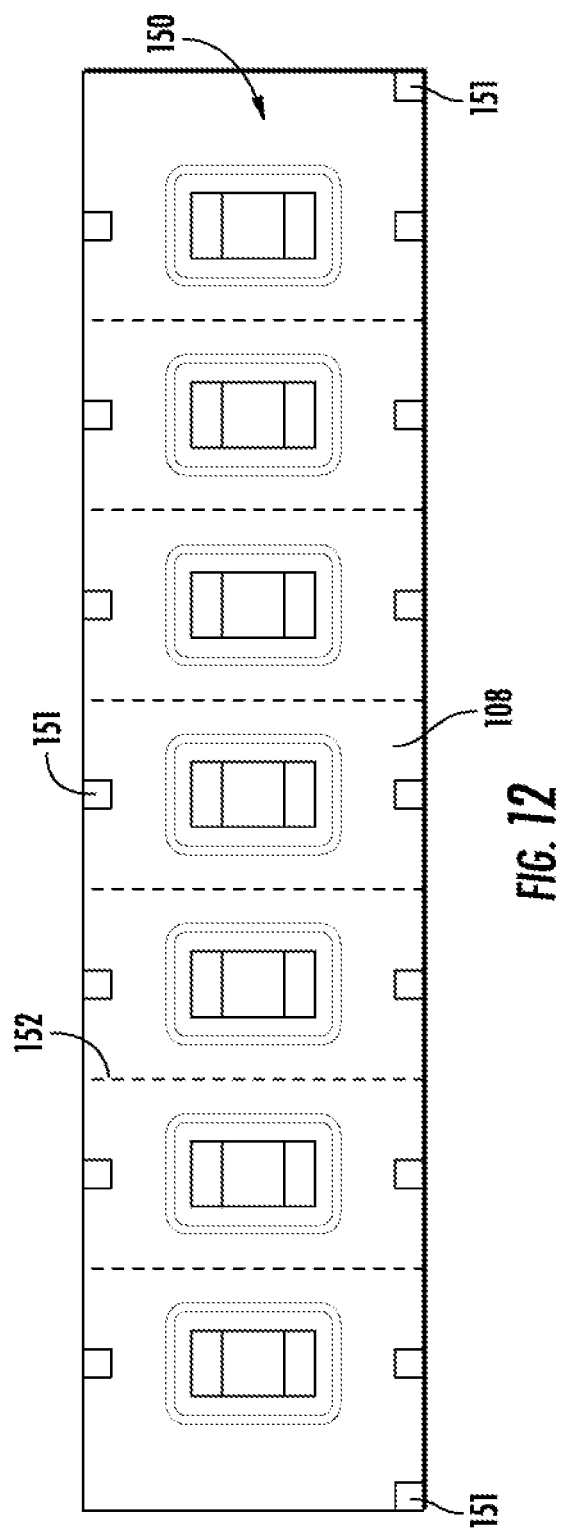
FIG. 12 illustrates a top view of a collection media assembly in accordance with an exemplary embodiment described herein.

FIGS. 10-12 illustrate various collection media assemblies in accordance with exemplary embodiments described herein. FIG. 10 illustrates a top view of a plurality of collection media assemblies disposed upon a rotatable disc in accordance with an exemplary embodiment. In various embodiments, a plurality of collection media assemblies 150 may be disposed upon a rotatable disc that may be rotatable about an axis such that the plurality of collection media assemblies 150 (e.g., comprising a plurality of collection media 106) may move relative to an internal sensor portion of a housing of a fluid composition sensor. The rotatable disc may be configured such that the plurality of collection media 106 may be moved (e.g., rotated) relative to the fluid composition sensor such that a fresh (e.g., unused) collection media 106 of the plurality of collection media assemblies 150 may be exposed to a volume of fluid flowing through an impactor nozzle, as described herein.

In various embodiments, the rotatable disc may comprise a coplanar and concentric plurality of disc portions, each of the disc portions comprising portion of the rotatable disc upon which one or more of the plurality of collection media assemblies 150 may be disposed. For example, as illustrated in FIG. 10, the rotatable disc may comprise a first disc portion 108A and a second disc portion 108B, upon each of which is a plurality of collection media assemblies 150. Each of the disc portions may be defined at least in part by a corresponding radial distance between the disc portion and the central axis of the rotatable disc, wherein the radial distance corresponding to each of the disc portions comprises a distinct value such that the plurality of disc portions may define a plurality of circumferential layers extending radially outwardly from the central axis of the rotatable disc.

The plurality of disc portions may be configured to increase the capacity of rotatable disc with respect to the number of collection media 106 disposed thereon. In various embodiments, the exemplary device described herein may be configured such that the rotatable disc may be rotated and/or moved linearly (e.g., in a radial direction relative to the disk) relative to the fluid composition sensor so as to position an unused collection media 106 of the plurality of collection media assemblies 150 at least substantially adjacent an outlet of an impactor nozzle of the fluid composition sensor, as described herein.

As described herein, each of the plurality of collection media 106 of the plurality of collection media assemblies 150 may be disposed upon a transparent substrate. In various embodiments, at least a portion of the rotatable disc upon which the plurality of collection media 106 is disposed may comprise a transparent substrate, however opaque or translucent materials may be utilized for defining portions of the disk between included collection media assemblies 150. For example, in various embodiments, the entirety of the rotatable disc may comprise a transparent substrate. Further, in various embodiments, the rotatable disc may comprise one or more alignment keys 151 configured to assist with the manual and/or mechanical installation and/or alignment of a collection media 106 disposed upon the rotatable disc in a position such that a volume of fluid flowing through the fluid composition sensor (e.g., through the impactor nozzle) may be passed across a surface of the collection media 106. The rotatable disc may comprise a plurality of orifices corresponding to the at least one orifice 111 of each of the plurality of collection media assemblies 150, configured such that a volume of fluid may flow therethrough. In various embodiments, each of the plurality of collection media assemblies 150 may comprise an air seal engagement portion 115A surrounding a corresponding one of the plurality of collection media 106 and the at least one orifice 111 positioned adjacent thereto. In such a configuration, a volume of fluid flowing through the sensor may be passed across a surface of the collection media 106 surrounded by an air seal engagement portion 115A engaged with an air seal component of the fluid composition sensor, as described herein. For example, the collection media 106 surrounded by an air seal engagement portion 115A engaged with an air seal component of the fluid composition sensor may be fluidly isolated from each of the other collection media of the plurality of collection media disposed upon the rotatable disc.

FIG. 11 illustrates a top view of a plurality of collection media assemblies disposed upon an alignment plate in accordance with an exemplary embodiment. In various embodiments, a plurality of collection media assemblies 150 may be disposed upon an alignment plate that may be moveable about a plane such that the plurality of collection media assemblies 150 (e.g., comprising a plurality of collection media 106) may move relative to an internal sensor portion of a housing of a fluid composition sensor. The alignment plate may be configured such that the plurality of collection media 106 may be moved (e.g., linearly shifted) along at least two directional axes (e.g., an x-axis and a y-axis existing within a plane) relative to the fluid composition sensor such that a fresh (e.g., unused) collection media 106 of the plurality of collection media assemblies 150 may be exposed to a volume of fluid flowing through an impactor nozzle, as described herein. As illustrated in FIG. 11, in various embodiments, the plurality of collection media assemblies 150 disposed upon the alignment plate may be arranged so as to define an array comprising plurality of rows and columns.

As described herein, each of the plurality of collection media 106 of the plurality of collection media assemblies 150 may be disposed upon a transparent substrate. In various embodiments, at least a portion of the alignment plate upon which the plurality of collection media 106 is disposed may comprise a transparent substrate. For example, in various embodiments, the entirety of the alignment plate may comprise a transparent substrate (however, portions of the alignment plate between the collection media assemblies may comprise opaque or translucent materials in certain embodiments). Further, in various embodiments, the alignment plate may comprise one or more alignment keys 151 configured to assist with the manual and/or mechanical installation and/or alignment of a collection media 106 disposed upon the alignment plate in a position such that a volume of fluid flowing through the fluid composition sensor (e.g., through the impactor nozzle) may be passed across a surface of the collection media 106. In various embodiments, the one or more alignment keys 151 may be arranged about the alignment plate so as to correspond to a particular row and a particular column of the array defined by the plurality of collection media assemblies 150.

The alignment plate may further comprise a plurality of orifices corresponding to the at least one orifice of each of the plurality of collection media assemblies 150, configured such that a volume of fluid may flow therethrough. In various embodiments, each of the plurality of collection media assemblies 150 may comprise an air seal engagement portion surrounding a corresponding one of the plurality of collection media 106 and the at least one orifice 111 positioned adjacent thereto. In such a configuration, a volume of fluid flowing through the sensor may be passed across a surface of the collection media 106 surrounded by an air seal engagement portion 115A engaged with an air seal component of the fluid composition sensor, as described herein. For example, the collection media 106 surrounded by an air seal engagement portion that is engaged with an air seal component of the fluid composition sensor may be fluidly isolated from each of the other collection media of the plurality of collection media disposed upon the alignment plate.

FIG. 12 illustrates a top view of a plurality of collection media assemblies disposed upon an alignment tape in accordance with an exemplary embodiment. In various embodiments, a plurality of collection media assemblies 150 may be disposed upon an alignment plate that may be moveable in a direction at least substantially parallel with a linear axis extending along the length of the alignment tape such that the plurality of collection media assemblies 150 (e.g., comprising a plurality of collection media 106) disposed thereon may move relative to an internal sensor portion of a housing of a fluid composition sensor. The alignment tape may be configured such that the plurality of collection media 106 may be moved (e.g., linearly shifted) relative to the fluid composition sensor such that a fresh (e.g., unused) collection media 106 of the plurality of collection media assemblies 150 may be exposed to a volume of fluid flowing through an impactor nozzle, as described herein. As illustrated in FIG. 12, in various embodiments, the plurality of collection media assemblies 150 disposed upon the alignment tape may be arranged so as to define a row of collection media assemblies 150 extending along the length of the alignment tape.

In various embodiments, at least a portion of the alignment tape upon which the plurality of collection media 106 is disposed may comprise a transparent substrate 108. For example, in various embodiments, the entirety of the alignment tape may comprise a transparent substrate 108 (although it should be understood that portions of the alignment tape between collection media assemblies 150 may comprise an opaque or translucent material). Further, in various embodiments, the alignment tape may comprise one or more alignment keys 151 configured to assist with the manual and/or mechanical installation and/or alignment of a collection media 106 disposed upon the alignment tape in a position such that a volume of fluid flowing through the fluid composition sensor (e.g., through the impactor nozzle) may be passed across a surface of the collection media 106. In various embodiments, the one or more alignment keys 151 may be arranged about the alignment tape so as to correspond to a particular collection media assembly 150 of the row defined by the plurality of collection media assemblies 150.

The alignment tape may further comprise a plurality of orifices corresponding to the at least one orifice of each of the plurality of collection media assemblies 150, configured such that a volume of fluid may flow therethrough. In various embodiments, each of the plurality of collection media assemblies 150 may comprise an air seal engagement portion surrounding a corresponding one of the plurality of collection media 106 and the at least one orifice positioned adjacent thereto. In such a configuration, a volume of fluid flowing through the sensor may be passed across a surface of the collection media 106 surrounded by an air seal engagement portion 115A engaged with an air seal component of the fluid composition sensor, as described herein. For example, the collection media 106 surrounded by an air seal engagement portion that is engaged with an air seal component of the fluid composition sensor may be fluidly isolated from each of the other collection media of the plurality of collection media disposed upon the alignment tape. As described herein, in various embodiments, the alignment tape may comprise a non-rigid (e.g., flexible, bendable, foldable, and/or the like) material. For example, each of the plurality of collection media assemblies 150 may be separated by a fold line, along which the alignment tape may be folded. In various embodiments, the non-rigid material of the alignment tape may facilitate the compact storage of the plurality of collection media assemblies 150 such that the capacity of the fluid composition sensor may be increased.

Figure 13:
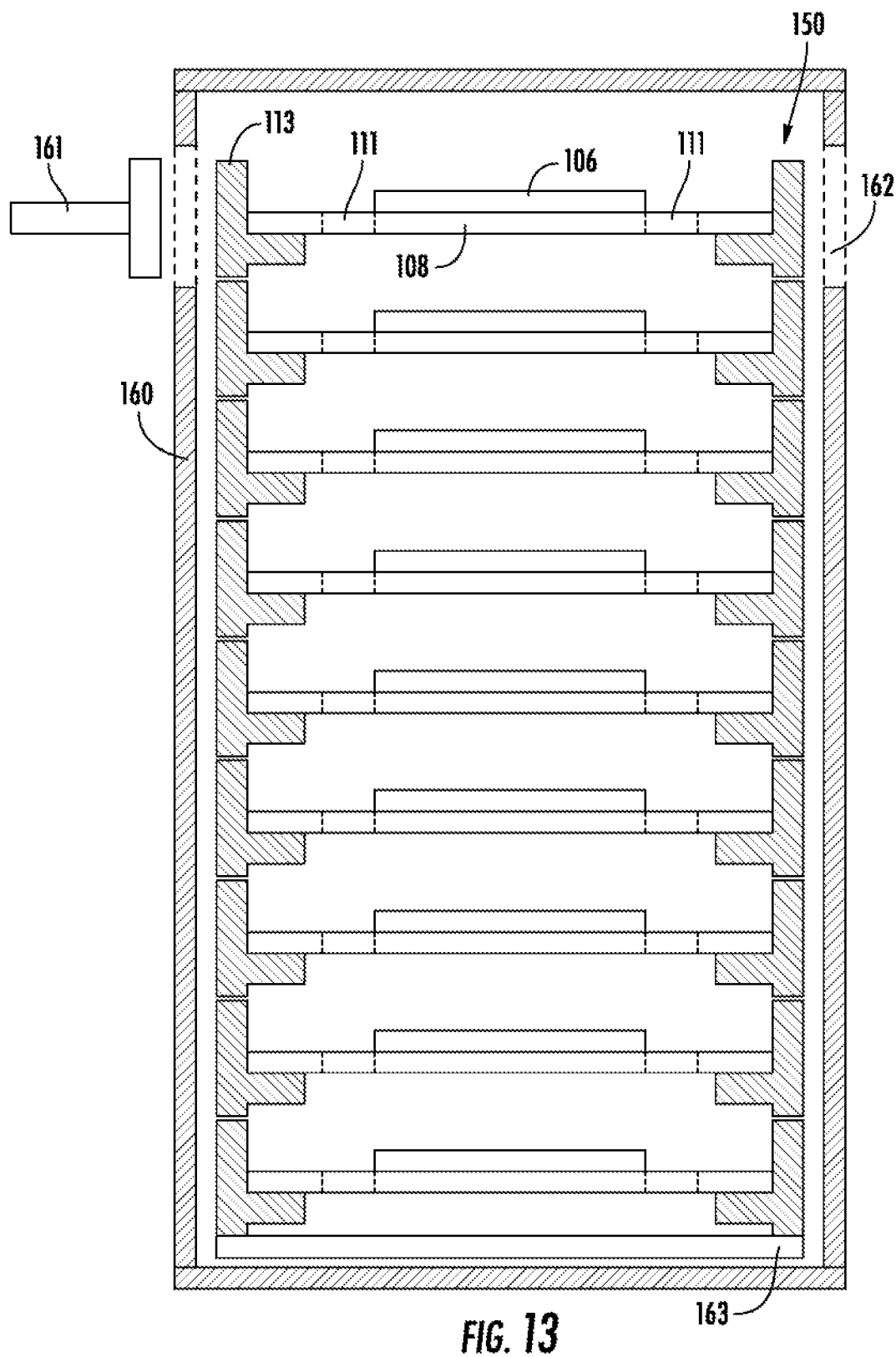
FIG. 13 illustrates a cross-sectional view of an exemplary apparatus in accordance with an exemplary embodiment described herein.

FIG. 13 illustrates a cross-sectional view of an exemplary apparatus in accordance with an embodiment described herein. In particular, FIG. 13 illustrates an exemplary collection media assembly storage chamber 160 configured to house at least a portion of a plurality of collection media. As described herein, in various embodiments, an exemplary collection media assembly 150 may be configured so as to facilitate the collective storage (e.g., stacking) and subsequent dispensing of each of a plurality of collection media assemblies 150 into an internal sensor portion of a fluid composition sensor. As illustrated in FIG. 13, a plurality of exemplary collection media assemblies 150 may be disposed within the collection media assembly storage chamber 160. In various embodiments, the collection media assembly storage chamber 160 may store a plurality of unused collection media assemblies prior to the plurality of collection media assemblies being respectively used in sequence for particle collection within a fluid composition sensor. The collection media assembly storage chamber 160 may be configured so as to at least substantially minimize the exposure of each of the collection media assemblies 150 stored therein to an ambient environment in order to avoid a contamination of the corresponding collection media 106.

As described herein, the collection media assembly storage chamber 160 may be further configured to consecutively transmit each of the plurality of collection media assemblies 150 stored therein in series to an internal sensor portion of a fluid composition sensor. In various embodiments, the collection media assembly storage chamber 160 may comprise an actuator element 161 configured to selectively apply a force to one of the plurality of collection media stored within the collection media assembly storage chamber so as to reposition a collection media assembly 150 from the collection media assembly storage chamber 160 towards an internal sensor portion of the fluid composition sensor. For example, the actuator element 161 may be configured to move from a compressed position, as illustrated in FIG. 13, to an extended position. As the actuator element 161 moves from the compressed position to the extended position, the actuator element 161 may be configured to apply a force to a collection media assembly 150. In various embodiments, the force applied to the collection media assembly 150 as the actuator element 161 moves from the compressed position to the extended position may cause the collection media assembly to be repositioned such that, when the actuator element 161 is in the extended position, the collection media assembly 150 may be in a receiving position within the internal sensor portion of the fluid composition sensor. In various embodiments, a receiving position may be defined by an arrangement of a collection media assembly 150 within the internal sensor portion of the fluid composition sensor wherein the corresponding collection media 106 is positioned such that a volume of fluid flowing through the fluid composition sensor (e.g., through an impactor nozzle) may be passed across a surface thereof. In various embodiments, upon extending from a compressed position to an extended position (e.g., so as to position a collection media assembly 150 in a receiving position), the actuator element 161 may be configured to retract from the extended position back to the compressed position. Further, in various embodiments, the actuator element 161 may comprise a gear drive mechanism and/or a lever arm mechanism that may be configured to operate according to one or more embodiments described herein.

As illustrated, the collection media assembly storage chamber 160 may comprise a dispense opening 162 within one or more walls of the chamber, the dispense opening 162 being configured to allow one or more of the collection media assemblies 150 stored within the collection media assembly storage chamber 160 to pass therethrough as the one or more of the collection media assemblies 150 are being transmitted to the internal portion of the fluid composition sensor. In various embodiments, the dispense opening 162 may comprise a dispense door that may be selectively opened and closed to facilitate the selective dispense of a collection media assembly 150. For example, in the exemplary embodiment illustrated in FIG. 13, the actuator element 161 may be configured to apply a transverse (e.g., horizontal) force on a collection media assembly 150 positioned in a loading position (e.g., at an uppermost position in a stack of collection media assemblies) so as to dispense the collection media assembly 150 from the collection media assembly storage chamber 160 through the dispense opening 162. As described herein, the collection media assembly storage chamber 160 may be positioned proximate a housing of the fluid composition sensor such that the housing is configured to receive the at least a portion of collection media assembly 150 dispensed from the collection media assembly storage chamber 160 by the extension of the actuator element 161 repositioning a collection media assembly 150 through the dispense opening. Accordingly, the dispense opening 162 may be at least substantially planar with an internal sensor portion (e.g., a position of a collection media assembly 150 when in use for collecting particles of an airflow). As described above, the collection media assembly storage chamber 160 may be configured to dispense a collection media assembly 150 through a dispense opening 162 (e.g., using an actuator element 161) so as to deliver the collection media assembly 150 to a receiving position within the internal sensor portion of the fluid composition sensor.

The collection media assembly storage chamber 160 may be configured to arrange within the chamber the plurality of collection media assemblies 150 such that they may be consecutively transmitted in series from a storage location to a receiving position within the internal sensor portion of the fluid composition sensor, as described herein. For example, the collection media assembly storage chamber 160 may define a loading position arranged proximate and/or at least substantially planar with the actuator element 161 and/or the dispense opening 162, wherein a collection media assembly 150 positioned in a loading position may be the next collection media assembly 150 of the plurality disposed within the collection media assembly storage chamber 160 to be transmitted to a fluid composition sensor (e.g., sequentially before each of the other collection media assemblies stored within the collection media assembly storage chamber 160). As illustrated in FIG. 13, the plurality of collection media assemblies 150 stored within the collection media assembly storage chamber 160 may be arranged in a stack. As shown, the loading position may comprise the position proximate the actuator element 161 and/or the dispense opening 162 (e.g., the top of the stack). In various embodiments, the collection media assembly storage chamber 160 may comprise a loading element 163 configured to arrange the plurality of collection media assemblies 150 disposed within the collection media assembly storage chamber 160 such that, upon the dispense of a first collection media assembly, a second collection media is moved within the collection media assembly storage chamber 160 into a loading position. For example, the loading element 163 may comprise a plate configured to which a bias force may be applied such that the plate transmits a corresponding loading force to one or more of the plurality of collection media assemblies 150. In such an exemplary circumstance, a bias force may be applied (e.g., via a spring) to a bottom surface of the loading element 163 so as to push a subsequently stacked collection media assembly 150 of the plurality into the loading position. In various embodiments, the bias force applied to the loading element 163 and/or the loading force applied from the loading element 163 to one or more of the plurality of collection media assemblies 150 may be either a constant force or an intermittent force selectively applied between subsequent collection media assembly 150 dispenses in order to arrange the plurality of collection media assemblies such that at least one collection media assembly 150 is in a loading position.

Figure 14A:
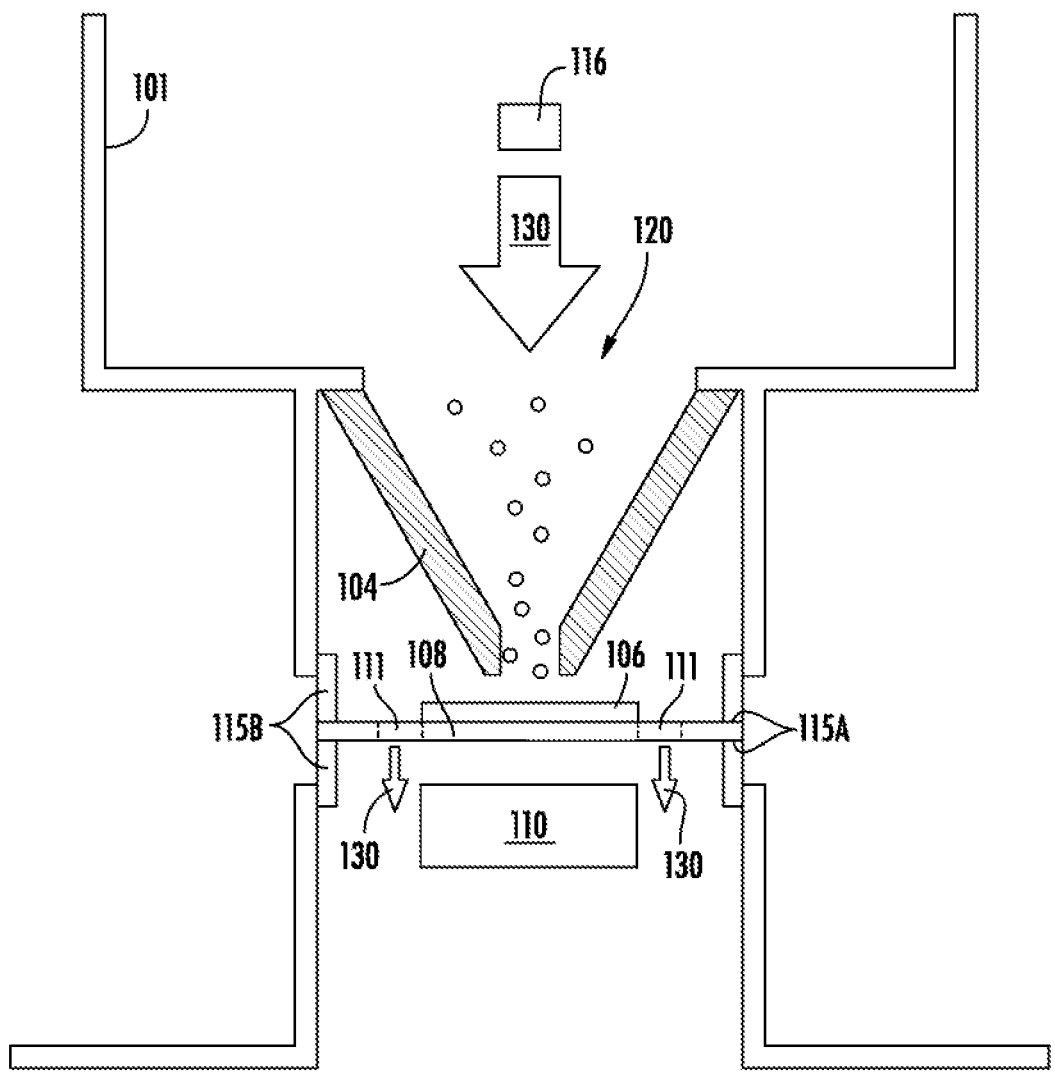
FIGS. 14A-14B illustrate an exemplary apparatus in accordance with various embodiments described herein.
Figure 14B:
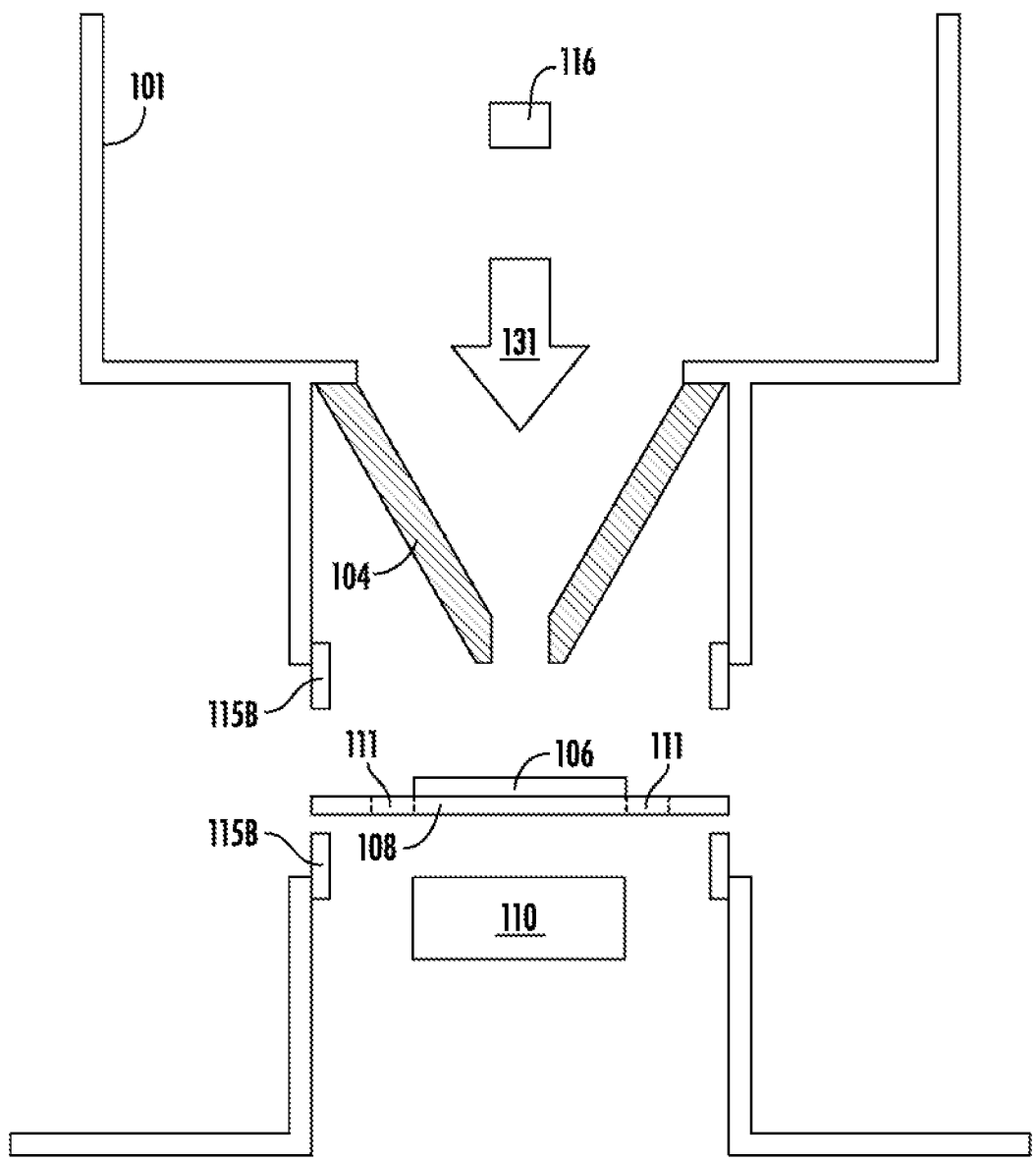

FIGS. 14A-14B illustrate an exemplary apparatus in accordance with various embodiments. As described herein, a fluid composition sensor may comprise a housing 101, an illumination source 116, an impactor nozzle 104, at least one collection media 106 disposed upon a transparent substrate 108, and an imaging device 110. In various embodiments, the fluid composition sensor may be configured to receive a volume of fluid within an internal sensor portion of the housing 101. The impactor nozzle 104 may be configured to direct the flow of at least a portion of the volume of fluid received by the fluid composition sensor 100 in a flow direction 130 at least substantially perpendicular to and directed toward a receiving surface of a collection media 106.

As described herein, the impactor nozzle 104 may be disposed within the internal sensor portion of the housing 101 and may comprise a nozzle inlet configured to receive at least a portion of the volume of fluid received by the fluid composition sensor, a nozzle outlet, and a plurality of sidewalls extending between the nozzle inlet and the nozzle outlet. Each of the plurality of sidewalls of the impactor nozzle may comprise an inner sidewall and an outer sidewall. In various embodiments, the nozzle inlet may comprise a nozzle inlet cross-sectional area defined at least in part by a perimeter formed by each of the inner sidewalls of the plurality of sidewalls at the nozzle inlet. Similarly, the nozzle outlet may comprise a nozzle outlet cross-sectional area defined at least in part by a perimeter formed by each of the inner sidewalls of the plurality of sidewalls at the nozzle outlet. In various embodiments, the impactor nozzle 104 may further comprise a central nozzle axis extending perpendicularly between the nozzle inlet and the nozzle outlet.

In various embodiments, the impactor nozzle 104 may comprise a first nozzle portion and a second nozzle portion, both of which may be defined at least in part by a portion of the plurality of sidewalls of the impactor nozzle 104. The first nozzle portion may comprise a portion of the impactor nozzle 104 defined at least in part by at least one tapered inner sidewall extending between the nozzle inlet and an intermediate nozzle location. The second nozzle portion may comprise a portion of the impactor nozzle 104 defined at least in part by at least one inner sidewall extending between the intermediate nozzle location and the nozzle outlet. As described herein, the intermediate nozzle location may comprise an intermediate nozzle cross-sectional area and may be defined by a plane arranged perpendicular to the central axis of the impactor nozzle 104 between the first nozzle portion and the second nozzle portion. In various embodiments, the first nozzle portion may be configured such that the nozzle inlet cross-sectional area is larger than the intermediate nozzle cross-sectional width. Further, as described in further detail herein, the second nozzle portion may be configured such that the nozzle outlet cross-sectional area may be either larger, smaller, or at least substantially the same size as the intermediate nozzle cross-sectional area. For example, as shown in FIG. 14, the impactor nozzle 104 is configured such that the nozzle outlet cross-sectional area and the intermediate nozzle cross-sectional area are substantially the same size.

As described, the impactor nozzle 104 may receive at least a portion of the volume of fluid received by the fluid composition sensor 100 and may be configured so as to direct the volume of fluid in a flow direction 130 at least substantially perpendicular to and directed toward a receiving surface of a collection media 106. For example, flow direction 130 may be at least substantially aligned and/or parallel with the central nozzle axis of the impactor nozzle 104. The collection media 106 may be configured to receive one or more particles of a plurality of particles 120 within the volume of fluid via interaction with the volume of fluid directed from the impactor nozzle 104. As described herein, the collection media 106 may be a component of a collection media assembly, which may further comprise a transparent substrate 108 and at least one orifice 111. As described herein, the at least one orifice 111 may be configured to enable at least a portion of the volume of fluid to pass through the transparent substrate 108 and continue through the internal sensor portion in flow direction 130.

In various embodiments, the fluid composition sensor may further comprise one or more air seal components 115B configured to engage one or more corresponding air seal engagement portions 115A of the collection media assembly disposed within the internal sensor portion of the housing. As described herein, the one or more air seal components 115B may be configured to surround at least the collection media 106 and the corresponding at least one orifices 111 so as to fluidly isolate the collection assembly 106 from an ambient environment such that at least substantially all of the volume of fluid flowing through the fluid composition sensor flows through the at least one orifice 111.

As described, the fluid composition sensor may comprise an illumination source 116 configured to emit one or more light beams. In various embodiments, the illumination source 116 may be a laser, lamp, light-emitting diode (LED), and/or the like, which may operate in connection with one or more lenses collectively configured to generate a light beam (e.g., ultraviolet, visible, infrared, or multiple color light) that may be emitted toward the collection media 106, as described herein in further detail. In some embodiments, the illumination source 116 may be configured such that a lens is not required, such as, for example, when the fluid composition sensor is configured to execute lensless holography, as described herein. For example, as illustrated in FIG. 14B, the illumination source may be configured to emit the one or more light beams in a light emission direction 131, such that the light beams may engage the collection media 106 and illuminate the one or more particles disposed within the collection media 106. Further, as described herein, the fluid composition sensor may further comprise an imaging device 110 configured to capture an image of the one or more particles of the plurality of particles 120 received by the collection media 106. In various embodiments, the imaging device 110 may be positioned at least substantially adjacent (e.g., in contact with or spaced a distance away from) the transparent substrate 108 such that the imaging device 110 may effectively capture one or more images of the one or particles captured within the collection media 106. The collection media 106 may reside at least partially within the field of view of the imaging device 110, such that the plurality of particles 120 captured by the collection media 106 are visible by the imaging device 110. In various embodiments, the imaging device 110 may be configured to capture the image of one or more particles of the plurality of particles 120 received by the collection media 106 using one or more imaging techniques such as, for example, lensless holography, optical microscopy, and/or the like.

As described herein, in various embodiments, a fluid composition sensor may be configurable between an open housing configuration and a closed configuration. In particular, FIG. 14A illustrates a cross-sectional view of an exemplary fluid composition sensor in a closed configuration. A fluid composition sensor in a closed housing configuration may be defined at least in part by the engagement of the at least one air seal components 115A with the air seal engagement portion of the collection media assembly. As described herein, such an engagement by the fluid composition sensor in the closed configuration may provide a secured seal surrounding at least the collection media 106 and the one or more corresponding orifices 111 so as to isolate the collection media 106 and the one or more corresponding orifices 111 from a volume of ambient fluid, thereby minimizing unwarranted contamination of adjacent sections of the collection media 106.

FIG. 14B illustrates a cross-sectional view of an exemplary fluid composition sensor in an open configuration. In various embodiments, a fluid composition sensor in an open housing configuration may be configured so as to allow for the reconfiguration of a collection media assembly relative to at least a portion of the internal sensor portion of the housing 101. In various embodiments wherein the fluid composition sensor is in an open configuration, a collection media assembly comprising a collection media 106 disposed within the internal sensor portion of the fluid composition sensor may be reconfigured such that the collection media 106 is removed from the internal sensor portion. For example, the collection media assembly may be removed from the internal sensor portion and transported to an exemplary secondary location. Additionally, wherein the fluid composition sensor is in an open configuration, a collection media assembly comprising a collection media 106 positioned outside of the housing 101 may be reconfigured such that the collection media 106 is deposited into the internal sensor portion of the housing 101. For example, the collection media assembly may be rotated and/or shifted relative to the internal sensor portion such that the collection media 106 is arranged at least substantially adjacent the nozzle outlet of the impactor nozzle 104. Although illustrated with respect to various exemplary embodiments described herein as comprising a physical opening such that one or more components of the fluid composition sensor disposed within the internal sensor portion of the housing may be exposed to a volume of ambient fluid, it should be understood that, in various embodiments, the internal sensor portion of the fluid composition sensor may remain at least substantially isolated from the ambient environment in an open configuration in order to avoid sensor contamination.

Figure 15:
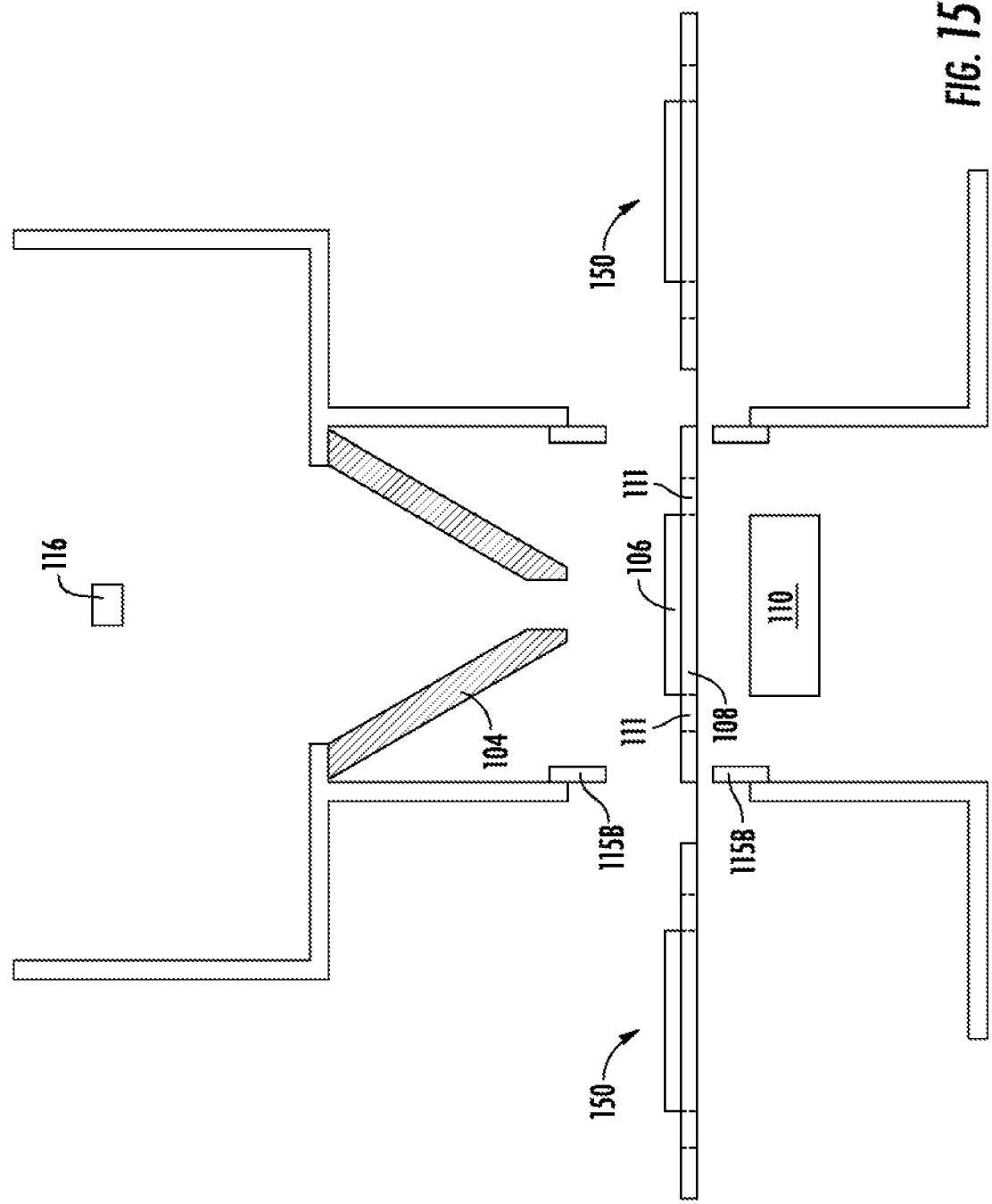
FIG. 15 illustrates a cross-sectional view of an exemplary apparatus in accordance with one embodiment described herein.

FIGS. 15-17 illustrate various cross-sectional views of exemplary apparatuses in accordance with embodiments described herein. In particular, FIG. 15 illustrates a cross-sectional view of an exemplary fluid composition sensor in an open configuration, wherein the exemplary fluid composition sensor comprises a plurality of collection media assemblies 150 disposed upon an alignment plate. For example, the plurality of collection media assemblies 150 disposed upon the alignment plate me be arranged so as to define an array comprising plurality of rows and/or columns. As described herein, the fluid composition sensor may be configured such that when the fluid composition sensor is in the open configuration, the alignment plate may be moveable about a transverse plane in a plurality of directions such that the plurality of collection media assemblies 150 (e.g., comprising a plurality of collection media 106) disposed thereon may move relative to the internal sensor portion of a housing 101. The alignment plate may be configured such that the plurality of collection media 106 may be moved (e.g., linearly shifted and/or rotated) relative to the housing 101 such that a fresh (e.g., unused) collection media 106 of the plurality of collection media assemblies 150 may be exposed to a volume of fluid flowing through an impactor nozzle 104. As described herein, upon the arrangement of an unused collection media 106 in a desired position at least substantially adjacent the nozzle outlet of the impactor nozzle 104, the fluid composition sensor may be reconfigured to a closed configuration, thereby securing the position of the collection media 106 relative to the nozzle outlet.

FIG. 16 illustrates a cross-sectional view of an exemplary fluid composition sensor in an open configuration, wherein the exemplary fluid composition sensor comprises a plurality of independent collection media assemblies 150 each being configured to be consecutively disposed within the internal sensor portion of the fluid composition sensor in series. In various embodiments, the fluid composition sensor may comprise one or more collection media assembly storage chambers configured to store at least a portion of the plurality of collection media assemblies. Further, in various embodiments, each of the at least one collection media assembly storage chambers may be configured to dispense into and/or receive from the housing 101 one or more of the plurality of collection media assemblies 150. For example, as illustrated, the fluid composition sensor may comprise a first collection media assembly storage chamber 160 and a second collection media assembly storage chamber 164.

As illustrated in FIG. 16, each of the plurality of collection media assemblies 150 comprise a collection media disposed upon a transparent substrate, a plurality of orifices arranged adjacent the corresponding collection media and extending through the transparent substrate 108, an air seal engagement portion, and a collection media housing (e.g., a frame element). As described herein, in various embodiments, each of a plurality of collection media assemblies 150 may be configured so as to facilitate the collective storage thereof in a collection media assembly storage chamber. For example, as illustrated, at least a portion of the plurality of the collection media assemblies 150 may be organized in a stacked configuration the corresponding collection media housings may be stacked relative to one another so as to minimize unwarranted contamination of a collection media through physical engagement of the collection media with one or more components of an adjacent collection media assembly (e.g., a corresponding collection media housing).

In various embodiments, the first collection media assembly storage chamber 160 may store a plurality of unused collection media assemblies prior to the plurality of collection media assemblies being respectively used for particle collection within a fluid composition sensor. For example, the first collection media assembly storage chamber 160 may be configured to arrange within the chamber the plurality of collection media assemblies 150 such that they may be consecutively transmitted in series from the first collection media assembly storage chamber 160 to the internal sensor portion of the fluid composition sensor. In various embodiments, the collection media assembly storage chamber 160 may comprise an actuator element 161 configured to selectively apply a force to one of the plurality of collection media stored within the first collection media assembly storage chamber 160 (e.g., in a loading position) so as to reposition the collection media assembly 150 from the collection media assembly storage chamber 160 towards an internal sensor portion of the housing 101 of the fluid composition sensor (e.g., into alignment with the impactor nozzle 104). For example, in the exemplary embodiment illustrated in FIG. 16, the actuator element 161 of the first collection media assembly storage chamber 160 may be configured to apply a transverse force to a collection media assembly 150 positioned in a loading position (e.g., at an uppermost position in a stack of collection media assemblies) so as to dispense the collection media assembly 150 from the first collection media assembly storage chamber 160 and into the interior sensor portion of the fluid composition sensor. As described herein, the first collection media assembly storage chamber 160 may be positioned proximate the housing of the fluid composition sensor such that the housing may configured to receive the collection media assembly 150 dispensed from the collection media assembly storage chamber 160.

In various embodiments, the fluid composition sensor may comprise a second collection media assembly storage chamber 164 configured to store a plurality of used collection media assemblies 150 (e.g., a collection media assembly 150 comprising a collection media 106 that has been disposed within the internal sensor portion and comprising a surface that has been passed over by at least one volume of fluid such that one or more particles from the volume of fluid are disposed therein) dispensed from the fluid composition sensor housing. For example, the second collection media assembly storage chamber 164 may be configured to receive the plurality of collection assemblies 150 consecutively transmitted in series from the internal sensor portion of the fluid composition sensor to the second collection media assembly storage chamber 168. The second collection media assembly storage chamber 164 may comprise a deposit opening within one or more walls of the chamber, the deposit opening being configured to allow one or more of the collection media assemblies 150 dispensed from the housing to pass therethrough such that the one or more collection media assemblies 150 may be transmitted from the internal portion of the fluid composition sensor to the second collection media assembly storage chamber 164. In various embodiments, the deposit opening may comprise a deposit door that may be selectively opened and closed to facilitate the selective receipt of a collection media assembly 150.

As described herein, upon determining that at least substantially the entirety of a sample volume of fluid has passed across a surface of a collection media 106, the fluid composition sensor may be configured to dispense the used collection media 106 and repopulate the inner sensor portion with an unused collection media 106. In various embodiments, the fluid composition sensor may be configured to receive an unused collection media assembly 150 (e.g., an unused collection media 106) from the first collection media assembly storage chamber 160 and transmit the used collection media 106 to the second collection media assembly storage chamber 164 at either a substantially similar time (e.g., simultaneously) or a different time (e.g., in sequence).

FIG. 17 illustrates a cross-sectional view of an exemplary fluid composition sensor in an open configuration, wherein the exemplary fluid composition sensor comprises a plurality of collection media assemblies 150 disposed upon an alignment tape. As illustrated in FIG. 17, the plurality of collection media assemblies 150 disposed upon the alignment tape may be arranged so as to define a row of collection media assemblies 150 extending along the length of the alignment tape. In various embodiments, the alignment tape may be moveable in a direction at least substantially parallel with a linear axis extending along the length of the alignment tape such that the plurality of collection media assemblies 150 (e.g., comprising a plurality of collection media 106) disposed thereon may move relative to an internal sensor portion of a housing of a fluid composition sensor. In various embodiments, at least a portion of the alignment tape may be wound about both the first alignment tape spool 165A and the second alignment tape spool 165B, which may be collectively arranged such that at least a portion of the alignment tape may extend therebetween. The first alignment tape spool 165A and the second alignment tape spool 165B may be further configured such that the at least a portion of the alignment tape extending therebetween may have at least one collection media assembly 150 disposed thereon. For example, the fluid composition sensor may be configured such that the collection media assembly 150 disposed upon the at least a portion of the alignment tape extending between the first alignment tape spool 165A and the second alignment tape spool 165B may be disposed within the internal sensor portion at least substantially adjacent the nozzle outlet of the impactor nozzle 104.

In various embodiments, wherein the fluid composition sensor is in an open configuration, as illustrated, the alignment tape may be configured such that the plurality of collection media 106 may be moved (e.g., linearly shifted) relative to the fluid composition sensor housing such that a fresh (e.g., unused) collection media 106 of the plurality of collection media assemblies 150 may be exposed to a volume of fluid flowing through an impactor nozzle 104, as described herein. For example, the alignment tape may be configured to move relative to the housing of the fluid composition sensor based at least in part on the rotation of the first alignment tape spool 165A and the second alignment tape spool 165B. The first alignment tape spool 165A and the second alignment tape spool 165B may be configured to rotate in unison (e.g., in the same rotational direction at the same rate) such that the portion of the alignment tape extending therebetween may maintain a configuration wherein the one or more collection media 106 disposed thereon are at least substantially perpendicular to a central axis of the impactor nozzle 104.

FIGS. 18A-18D schematically illustrate exemplary apparatuses in accordance with various embodiments described herein. In particular, FIGS. 18A-18D schematically illustrate exemplary apparatuses comprising various impactor nozzle configurations in accordance with various embodiments described herein. As described herein, a fluid composition sensor may comprise an illumination source 116, an impactor nozzle 104, a collection media 106 disposed upon a transparent substrate 108, and an imaging device 110. In various embodiments, a fluid composition sensor may be configured to receive a volume of fluid comprising a plurality of particles. The fluid composition sensor may be further configured to utilize the impactor nozzle 104 to direct the volume of fluid toward a receiving surface of a collection media 106 in a flow direction at least substantially perpendicular to the collection media 106, so as to facilitate the engagement of the collection media 106 by the volume of fluid such the at least a portion of the plurality of particles within the volume of fluid may be disposed into the collection media 106.

As described herein, the impactor nozzle 104 may comprise a nozzle inlet configured to receive at least a portion of the volume of fluid received by the fluid composition sensor, a nozzle outlet, and a plurality of sidewalls extending between the nozzle inlet and the nozzle outlet. Each of the plurality of sidewalls of the impactor nozzle may comprise an inner sidewall 104A and an outer sidewall 104B. In various embodiments, the nozzle inlet may comprise a nozzle inlet cross-sectional area defined at least in part by a perimeter formed by each of the inner sidewalls 104A of the plurality of sidewalls at the nozzle inlet. Similarly, the nozzle outlet may comprise a nozzle outlet cross-sectional area defined at least in part by a perimeter formed by each of the inner sidewalls 104A of the plurality of sidewalls at the nozzle outlet. In various embodiments, the impactor nozzle 104 may further define a central nozzle axis extending perpendicularly between the nozzle inlet and the nozzle outlet.

Figure 18A:
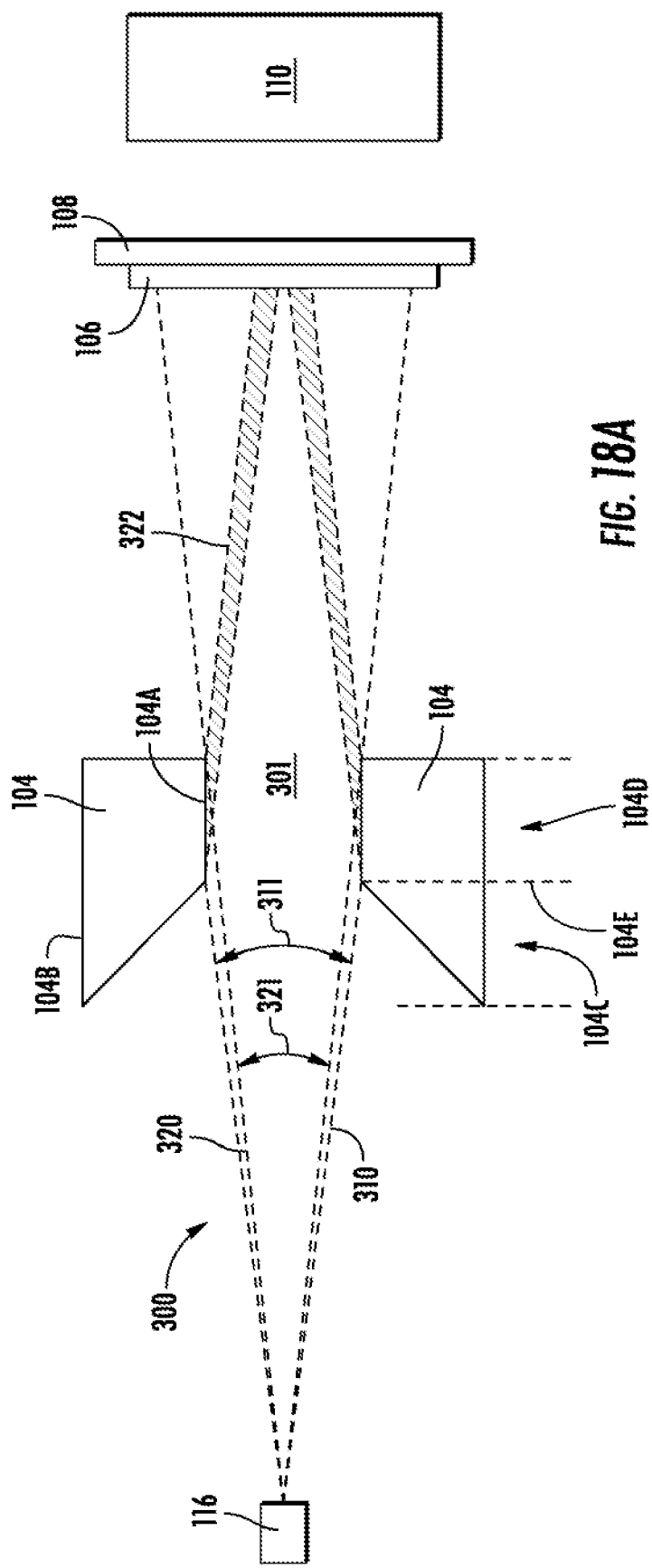

As illustrated in FIG. 18A, the impactor nozzle 104 may comprise a first nozzle portion 104C and a second nozzle portion 104D, both of which may be defined at least in part by a portion of the plurality of sidewalls of the impactor nozzle 104. The first nozzle portion 104C may comprise a portion of the impactor nozzle 104 defined at least in part by at least one tapered inner sidewall extending between the nozzle inlet and an intermediate nozzle location 104E. The second nozzle 104D portion may comprise a portion of the impactor nozzle 104 defined at least in part by at least a portion of one or more inner sidewalls 104A extending between the intermediate nozzle location 104E and the nozzle outlet. As described herein, the intermediate nozzle location 104E may comprise an intermediate nozzle cross-sectional area and may be defined by a plane arranged at least substantially perpendicular the central axis of the impactor nozzle 104 between the first nozzle portion 104C and the second nozzle portion 104D. In various embodiments, the first nozzle portion 104C may comprise a tapered configuration wherein the nozzle inlet cross-sectional area is larger than the intermediate nozzle cross-sectional area. Further, in various embodiments, the second nozzle portion may be configured such that the nozzle outlet cross-sectional area may be either larger, smaller, or at least substantially the same size as the intermediate nozzle cross-sectional area. For example, as shown in FIG. 18A, the impactor nozzle 104 is configured such that the nozzle outlet cross-sectional area and the intermediate nozzle cross-sectional area are substantially the same size. As described, the variable cross-sectional areas of the various sections of the impactor nozzle 104 may be configured to increase the velocity of the volume of fluid flowing through the nozzle (e.g., the plurality of particles therein) and induce laminar flow such that at least a portion of the particles of the plurality of particles within the volume of fluid comprise a momentum sufficient to impact the collection media 106 and become disposed therein.

In various embodiments, the illumination source 116 may be a laser, lamp, light-emitting diode (LED), and/or the like, which may generate one or more light beams 300 (e.g., ultraviolet, visible, infrared, or multiple color light) that may be emitted toward the collection media 106. For example, the illumination source 116 may be configured to emit the one or more light beams 300 in a light emission direction, such that the light beams may engage the collection media 106 and illuminate the one or more particles disposed within the collection media 106. Further, as described herein, the imaging device 110 of the fluid composition sensor may be configured to utilize the one or more light beams 300 in order to capture an image of the one or more particles of the plurality of particles 120 received by the collection media 106 using one or more imaging techniques such as, for example in situ imaging (e.g., lensless holography) and/or the like.

In various embodiments, the fluid composition sensor may be configured such that one or more illumination sources 116 may be arranged relative to the central nozzle axis of the impactor nozzle 104. For example, as illustrated in FIGS. 18A-18D, the fluid composition sensor may be configured such that the illumination source 116 is at least substantially aligned with the central nozzle axis of the impactor nozzle 104. In such a configuration, the illumination source 116 may emit the one or more light beams 300 in a light emission direction extending that is at least substantially similar to that of the central nozzle axis, such that at least a portion of the one or more light beams 300 extend through both the nozzle inlet and the nozzle outlet of the impactor nozzle 104 to illuminate the one or more particles disposed in the collection media 106. In various embodiments, as the one or more light beams 300 extend away from the illumination source 116 toward the collection media 106 in a light emission direction, the one or more light beams 300 may naturally diverge from the light emission direction such that the one or more light beams 300 may define a light beam emission angle. In such a circumstance, the one or more light beams may collectively embody a cone-shaped light beam defined at least in part by an outer edge thereof, wherein the cross-sectional area of the cone-shaped light beam increases as it extends toward the collection media 106 (e.g., along the central axis of the nozzle 104). In various embodiments, a light beam angle may correspond to an angle measured between an original light emission direction of a light beam (e.g., the central axis of the impactor nozzle 104) and an outer edge of the one or more light beams (e.g., the divergent light beam).

As illustrated in FIG. 18A, a divergent light beam 300 (comprising one or more light beams) may comprise an outer edge and an interior light beam portion 301, defined by the portion of the divergent light beam within the outer edge. For example, the divergent light beam 300 emitted from the illumination source 116 may be defined at least in part by outer edge 310. Further, the divergent light beam 300 may be further defined at least in part by an outer light beam angle 311 corresponding to an angle of divergence measured at the outer edge 310 (e.g., the angle measured between the outer edge 310 and the central axis of the impactor nozzle 104). For example, in various embodiments, at least a portion of the divergent light beam 300 may be constrained by intermediate nozzle location 104E.

In various embodiments, at least a portion of the interior portion 301 of the divergent light beam 300 may comprise a light beam angle that is sufficiently small so as to be emitted from the illumination source 116 and travel along a light emission travel path to the collection media 106 without substantially engaging a sidewall of the impactor nozzle 104. For example, the impactor nozzle 104 may be configured such that a portion of the interior portion 301 of the divergent light beam 300 defined by an intermediate edge 320 and an intermediate light beam angle 321 may extend between the illumination source 116 and the collection media 106 through both the nozzle inlet and the nozzle outlet without substantially engaging an interior sidewall 104A of the impactor nozzle 104.

Further, in various embodiments, the impactor nozzle 104 may be configured such that at least a portion of the divergent light beam 300 traveling therethrough may be incident on one or more of the interior sidewalls 104A. In such a circumstance, the portion of the divergent light beam incident on the interior sidewalls 104A may reflect and/or scatter off of the interior sidewalls 104A. For example, as illustrated, a portion of the interior portion 301 of the divergent light beam 300 defined by a light beam angle larger than the intermediate light beam angle 321 (e.g., outer light beam angle 321) and extending radially between the intermediate edge 320 and the outer edge 310 may be incident on the inner sidewalls 104A of the impactor nozzle 104. As such, a reflected portion 322 of the divergent light beam 300 may be generated. As shown, the reflected portion 322 may correspond to the portion of the interior portion 301 of the divergent light beam 300 incident on the interior sidewall of the second nozzle portion 104D. For example, the reflected portion 322, upon engaging the inner sidewall 104A may be diverted so as to travel through the nozzle outlet in a reflection direction that is substantially different than the light emission direction defined by the one or more light beams corresponding to the reflected portion 322 at the illumination source 116. In various embodiments, at least a portion of the reflected portion 322 of the divergent light beam 300 may proceed to illuminate collection media 106 and/or the imaging device 110. In such a circumstance, the reflected portion 322 of the divergent light beam 300 may affect the performance of the imaging device 110, causing, for example, optical interference that may be manifested by spatial variation of the apparent illumination intensity captured by the imaging device 110. In various embodiments, the reflected portion 322 may produce image noise that may at least partially obscure one or more features of the one or more particles disposed within the collection media 106, as described herein.

FIGS. 18B-18C schematically illustrate exemplary apparatuses comprising various impactor nozzle configurations in accordance with various embodiments described herein. In particular, FIGS. 18B-18C schematically illustrate an exemplary apparatus comprising an impactor nozzle 104 configured to avoid the generation of a reflected light beam portion, as described herein, caused by a portion of the divergent light beam 300 being incident on a sidewall of the impactor nozzle 104. As illustrated, the impactor nozzle 104 may be configured such that the second nozzle portion 104D may comprise at least one tapered inner sidewall extending between the intermediate nozzle location 104E and nozzle outlet. For example, as illustrated in FIG. 18B, the inner sidewall 104A at the second portion of the impactor nozzle 104 may comprise a tapered configuration defined at least in part by a taper angle 143A, such that the nozzle outlet cross-sectional area of the impactor nozzle 104 is larger than the intermediate nozzle cross-sectional area. In various embodiments, the taper angle 143 of the second nozzle portion may correspond to at least one light beam emission angle of the divergent light beam 300 emitted from the illumination source 116 (e.g., the outer light beam emission angle 311). For example, the taper angle 143 of the second nozzle portion may be at least as large as the outer light beam emission angle 311 corresponding to the outer light beam 310, as described herein, and therefore, may be at least as large as each of the light beam emission angles corresponding to the one or more light beams defined by the divergent light beam 300. In such an exemplary impactor nozzle 104 configuration, the interior wall 104A of the second nozzle portion of the impactor nozzle 104 may avoid interfering with the outer edge 310 of the divergent light beam 300, thereby avoiding the generation of a reflected light beam portion, as described herein.

As illustrated in FIG. 18C, in various embodiments, the taper angle 143A may reflect a difference of the configuration of the interior sidewall 104A as illustrated and an exemplary interior sidewall comprising a straight configuration (e.g., wherein the nozzle outlet cross-sectional area and the intermediate nozzle cross-sectional width are at least substantially similar, as illustrated in FIG. 18A). In various embodiments, the taper angle 143A may be sufficiently small so as to minimally impact the velocity and/or laminar flow of an exemplary volume of fluid flowing therethrough, as described herein. For example, based at least in part on the configuration of the illumination source 116, the taper angle 143A may be at least substantially between 1 and 10 degrees (e.g., between 2 and 5 degrees). In various embodiments, the taper angle 143A may be defined at least in part by the intermediate nozzle cross-sectional width and the distance between the illumination source 116 and the intermediate nozzle location. For example, in various embodiments, the taper angle Θ 143A may be defined by the equation below:

$$(\Theta) \geq \tan^{-1}\left(\frac{0.5 * \text{Intermediate Nozzle Cross} - SectionalWidth}{\text{Distance between Illumination Source 116 and Intermediate Nozzle Location}}\right)$$

Further, although illustrated with respect to various exemplary embodiments described herein as comprising linear (e.g., straight) sidewalls, it should be understood that, in various embodiments, one or more of the plurality of sidewalls of the impactor nozzle 104 may comprise an at least partially curved configuration. For example, as illustrated in FIGS. 18B-18C, the transition between the first nozzle portion and the second nozzle portion (e.g., about an intermediate nozzle location) may define a radius of curvature. As another example, the interior walls 104A of the impactor nozzle 104 may be at least partially curved such that no part of the divergent light beam 200 is incident on the sidewalls 104A.

FIG. 18D schematically illustrates an exemplary apparatus comprising an impactor nozzle configuration in accordance with various embodiments described herein. In particular, FIG. 18D schematically illustrates an exemplary apparatus comprising an impactor nozzle 104 configured to avoid the generation of a reflected light beam portion, as described herein, caused by a portion of the divergent light beam 300 being incident on a sidewall of the impactor nozzle 104. As illustrated, the impactor nozzle 104 may be configured such that the second nozzle portion, extending between the intermediate nozzle location and nozzle outlet, may comprise a straight configuration, wherein the nozzle outlet cross-sectional area and the intermediate nozzle cross-sectional width are at least substantially similar. For example, each of the interior sidewalls 104A on opposing sides of the central nozzle axis of the impactor nozzle may define an at least substantially parallel configuration, such that the taper angle 143 of the second nozzle portion may be at least substantially zero.

In various embodiments, in order to avoid interfering with the divergent light beam 300 (e.g., with the outer edge 310), at least a portion of one or more of the plurality of sidewalls of the impactor nozzle may be laterally moved in an outward direction (e.g., away from the central nozzle axis) so as to increase the nozzle outlet cross-sectional area and/or the intermediate cross-sectional area. The displacement of the at least a portion one or more of the plurality of sidewalls may effectively widen the second nozzle portion so as to enable the passage of the divergent light beam 300 through the impactor nozzle 104 without the interference of one or more of the interior sidewalls 104A. As described herein, in such an embodiment, the nozzle sidewalls may be moved in an outward direction (e.g., away from the central nozzle axis) for purposes of particle analysis (e.g., image acquisition) and may be moved in an inward direction (e.g., toward the central nozzle axis) for purposes of particle collection (e.g., controlling the flow of fluid toward the collection media 106).

As illustrated in FIG. 18D, the portion of one or more of the plurality of sidewalls defining the nozzle outlet may be displaced away from the central axis of the nozzle at a first sidewall displacement distance 144A. In various embodiments, one or more of the plurality of sidewalls may be displaced away from the central axis at different distances, such as, for example, a second sidewall displacement distance 144B. Alternatively, or additionally, in various embodiments, one or more of the plurality of sidewalls may be displaced away from the central axis of the nozzle at substantially the same distance, such as, for example, wherein the first sidewall displacement distance 144A and the second sidewall displacement distance 144B are at least substantially similar. In various embodiments, one or more of the sidewall displacement distances 144A, 144B may correspond, at least in part, to the outer light beam emission angle 311 of the divergent light beam 300 emitted from the illumination source 116. For example, in various embodiments, one or more of the sidewall displacement distances 144A, 144B may be defined at least in part by the outlet nozzle dimensions, the distance between the illumination source 116 and the nozzle outlet, and the divergence angle of the illumination beam(s).

In various embodiments, as described herein, the fluid composition sensor may comprise an exemplary impactor nozzle 104 that may be selectively configurable between a first nozzle configuration and a second nozzle configuration. For example, in various embodiments the first nozzle configuration correspond may to a particle collection functionality of the fluid composition sensor, and the second nozzle configuration may correspond to a particle analysis functionality of the fluid composition sensor. As described herein, the particle collection functionality of the fluid composition sensor may correspond to the fluid composition sensor receiving a volume of fluid comprising a plurality of particles and utilizing an impactor nozzle 104 to direct the volume of fluid toward a receiving surface of a collection media 106 in a flow direction at least substantially perpendicular to the collection media 106, so as to facilitate the engagement of the collection media 106 by the volume of fluid such that at least a portion of the plurality of particles within the volume of fluid may be disposed into the collection media 106. For example, in order to enable the particle collection functionality, the impactor nozzle 104 may be configured such that the nozzle outlet thereof is positioned at least substantially adjacent the collection media 106. Further, as described herein, the particle analysis functionality of the fluid composition sensor, may correspond to the fluid composition sensor capturing an image of the one or more particles received by the collection media 106 and determining, based at least in part on the image, at least one particle characteristic of volume of fluid received by the fluid composition sensor. For example, in order to enable the particle analysis functionality of the fluid composition sensor, the illumination source 116 may be configured to emit one or more light beams so as to engage the collection media 106 and illuminate the one or more particles received by collection media 106, as described herein. As described herein, in various embodiments, the fluid composition sensor may be configured to determine and/or identify one or more particle loading conditions at a collection media 106 based at least in part on one or more detected characteristics of the one or more emitted light beams emitted from an exemplary illumination source 116. As a non-limiting example, the fluid composition sensor (e.g., a controller 200) may be configured to determine the one or more particle loading conditions at a collection media 106 based at least in part on a total light intensity of at least a portion of the a collection media 106 within a field of view of the imaging device, the at least a portion of the collection media 106 being illuminated by the one or more light beams emitted from the illumination source 116.

As described herein, in various embodiments, the particle collection functionality and the particle analysis functionality of the fluid composition sensor may occur in sequence, such that upon determining that an entirety of a sample volume of fluid has passed across a surface of a collection media 106, and thus that the need for the particle collection functionality of the fluid composition sensor has been at least temporarily exhausted, the fluid composition sensor may be configured to initiate the particle analysis functionality. In various embodiments, the device 10 may comprise a controller 200, described in further detail herein, configured to generate and/or transmit one or more signals configured to cause the fluid composition sensor 110 to terminate a particle collection operation, such as by stopping operation of a pump 112 of the sensor 110 (e.g., by causing the pump 112 to adjust from an "ON" operational configuration to an "OFF" configuration) based at least in part on a detection by the controller 200 of one or more particle load conditions at the collection media 106. For example, the controller 200 may be configured to generate and/or transmit one or more signals configured to cause the fluid composition sensor 110 to terminate a particle collection operation by, for example, by stopping operation of a pump 112 of the sensor 110 (e.g., by causing the pump 112 to adjust from an "ON" operational configuration to an "OFF" configuration) based on a determination that a detected total light intensity of the collection media is below a predetermined light intensity threshold value. In various embodiments, a particle load condition may be defined at least in part by a spatial arrangement of a plurality of particles disposed at a collection media (e.g., particle clustering, spiking, particle touching, particles on top of each other, and/or the like), a particle coverage percentage, an average gray scale of all pixels in a captured image, a particle matter mass, a total light intensity, an amount of collected particles, calculated particle density, and/or the like.

Accordingly, in various embodiments, the fluid composition sensor may be configured to selectively alternate between the first nozzle configuration, corresponding with the particle collection functionality, and the second nozzle configuration, corresponding with the particle analysis functionality. For example, in one exemplary embodiment, the first nozzle configuration may be embodied by the exemplary nozzle configuration illustrated in FIG. 18A, described in further detail herein. The variable cross-sectional areas of the various sections and the minimized nozzle outlet cross-sectional area of the impactor nozzle 104 may be configured to increase the velocity of the volume of fluid flowing through the nozzle and induce laminar flow such that at least a portion of the plurality of particles within the volume of fluid may become disposed within the collection media 106 upon impact therewith. Further, in one exemplary embodiment, the second nozzle configuration may be embodied by the exemplary nozzle configuration illustrated in FIG. 18D, described in further detail herein. Wherein the particle analysis functionality of the fluid composition sensor may be enabled by the emission of one or more light beams (e.g., the divergent light beam 300) from the illumination source 116, an impactor nozzle 104 in the second nozzle configuration may avoid the generation of a reflected/scattered light beam portion, as described herein, caused by a portion of the divergent light beam 300 being incident on a sidewall of the impactor nozzle 104. In order to avoid interfering with the divergent light beam 300 (e.g., with the outer edge 310), at least a portion of one or more of the plurality of sidewalls of the impactor nozzle 104 may be laterally moved in a direction away from the central nozzle axis so as to increase the nozzle outlet cross-sectional area and/or the intermediate cross-sectional area. The displacement of the at least a portion one or more of the plurality of sidewalls may widen at least a portion of the impactor nozzle 104 so as to enable the passage of the divergent light beam 300 therethrough without the interference of one or more of the interior sidewalls 104A.

In various embodiments, the impactor nozzle 104 may be selectively configured between the first nozzle configuration or the second nozzle configuration based at least in part on either the application and/or removal of an applied force. For example, in various embodiments, the fluid composition sensor may be configured to alternate an impactor nozzle 104 from the first nozzle configuration to the second nozzle configuration by applying a force in an outward direction (e.g., away from the central nozzle axis) at one or more of the plurality of sidewalls of the impactor nozzle 104 in order to cause at least a portion of the sidewall to be displaced a first sidewall displacement distance 144A in the corresponding outward direction. In such a circumstance, the fluid composition sensor may be configured to selectively alternate the impactor nozzle 104 from the second nozzle configuration back to the first nozzle configuration by either removing the force being applied in the outward direction or applying an equal force in an inward direction (e.g., a direction opposite the outward direction) at the one or more of the plurality of sidewalls of the impactor nozzle 104.

Alternatively, in various embodiments, the fluid composition sensor may be configured to alternate an impactor nozzle 104 from the first nozzle configuration to the second nozzle configuration by removing a force being applied in an inward direction (e.g., toward the central nozzle axis) at one or more of the plurality of sidewalls of the impactor nozzle 104 in order to cause at least a portion of the sidewall to be displaced by a first sidewall displacement distance 144A in an outward direction that is at least substantially opposite the inward direction. In such a circumstance, the fluid composition sensor may be configured to selectively alternate the impactor nozzle 104 from the second nozzle configuration back to the first nozzle configuration by reapplying the inward force at the one or more of the plurality of sidewalls of the impactor nozzle 104 in order to cause the at least a portion of the sidewall to be retracted a first sidewall displacement distance 144A in the corresponding inward direction.

Further, in various embodiments, an impactor nozzle 104 in a second nozzle may be defined at least in part by a central nozzle axis that is reconfigured about the fluid composition sensor housing relative to the location of a central nozzle axis defined of an exemplary impactor nozzle in the first nozzle configuration. For example, the entirety of the impactor nozzle 104 may be rotated, shifted, and/or the like to a second nozzle location about the housing of the fluid composition sensor such that an impactor nozzle 104 in the second nozzle configuration may avoid the generation of a reflected light beam portion caused by a portion of the divergent light beam 300 being incident on the impactor nozzle 104.

Figure 19A:
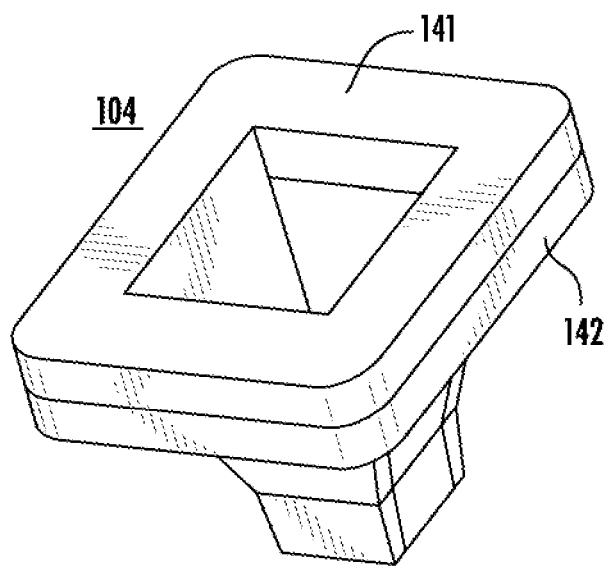
FIGS. 19A-19C illustrate perspective views of an exemplary apparatus in accordance with various embodiments.
Figure 19B:
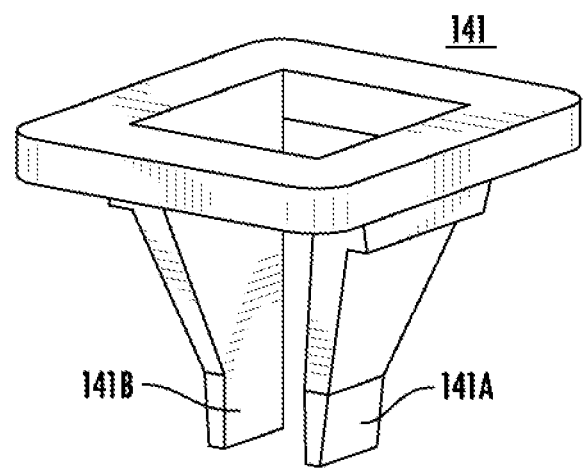
Figure 19C:
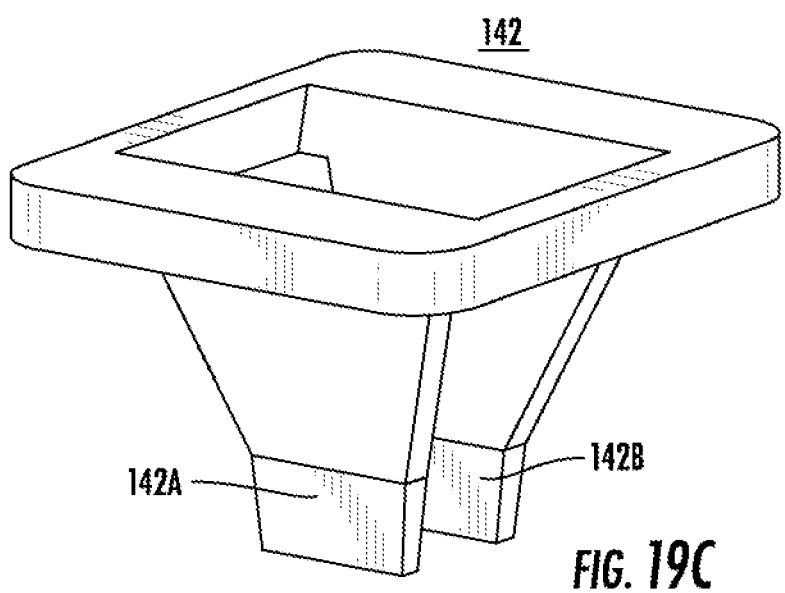

FIGS. 19A-19C illustrate perspective views of an exemplary apparatus in accordance with various embodiments. In particular, FIGS. 19A-19C illustrate an exemplary impactor nozzle configuration in accordance with various embodiments described herein. In various embodiments, an impactor nozzle 104 may comprise a plurality of nozzle components (e.g., two components, three components, five components, and/or the like) may be at least partially pieced together to collectively define the impactor nozzle 104. As illustrated in FIG. 19A, an impactor nozzle 104 may comprise two nozzle components, a first nozzle component 141 and a second nozzle component 142. In various embodiments, the first nozzle component 141 and the second nozzle component 142 may embody two distinct components of an impactor nozzle 104 respectively defined at least in part by corresponding elements such that the two distinct components may be pieced together to collectively define the impactor nozzle 104. As illustrated, and as described herein, the exemplary impactor nozzle 104 defined by the first nozzle component 141 and the second nozzle component 142 may comprise a nozzle inlet, a nozzle outlet, and a plurality of sidewalls extending between the nozzle inlet and the nozzle outlet. Each of the plurality of sidewalls of the impactor nozzle may comprise an inner sidewall and an outer sidewall. In various embodiments, the nozzle inlet may comprise a nozzle inlet cross-sectional area defined at least in part by a perimeter formed by each of the inner sidewalls of the plurality of sidewalls at the nozzle inlet. Similarly, the nozzle outlet may comprise a nozzle outlet cross-sectional area defined at least in part by a perimeter formed by each of the inner sidewalls of the plurality of sidewalls at the nozzle outlet. In various embodiments, the impactor nozzle 104 may further comprise a central nozzle axis extending perpendicularly between the nozzle inlet and the nozzle outlet. Further, as illustrated in FIG. 19A, the first nozzle component 141 and the second nozzle component 142 may be configured such that the impactor nozzle 104 may comprise a first nozzle portion, a second nozzle portion, and an intermediate nozzle location positioned therebetween. The first nozzle component 141 and the second nozzle component 142 may be configured such that the first nozzle portion and the second nozzle portion of the impactor nozzle 104 are configured according to various exemplary embodiments described in further detail herein. In various embodiments, the first nozzle component 141 and the second nozzle component 142 may comprise different characteristics such as, for example, material composition.

FIG. 19B illustrates a perspective view of an exemplary first nozzle portion 141 in accordance with various embodiments. In various embodiments, the first nozzle portion 141 may comprise an upper portion defining a first nozzle portion inlet and one or more first nozzle portion sidewalls. In various embodiments, one or more first nozzle portion sidewalls may define at least a portion of the plurality of plurality of sidewalls of the impactor nozzle 104. As shown, the first nozzle portion 141 comprises two first nozzle portion sidewalls 141A, 141B.

FIG. 19C illustrates a perspective view of an exemplary second nozzle portion 141 in accordance with various embodiments. In various embodiments, the second nozzle portion 142 may comprise an upper portion defining a second nozzle portion inlet and one or more second nozzle portion sidewalls. In various embodiments, one or more second nozzle portion sidewalls may define at least a portion of the plurality of sidewalls of the impactor nozzle 104. As shown, the second nozzle portion 142 comprises two second nozzle portion sidewalls 142A, 142B.

In various embodiments, as described herein, the first nozzle component 141 and the second nozzle component 142 may comprise corresponding elements that may be pieced together to collectively define the impactor nozzle 104. For example, the upper portions of the first nozzle component 141 and the second nozzle component 142 may be configured so as to engage one another in a stacked configuration. The respective upper portions may be at least substantially aligned so as to collectively define, at least in part, the nozzle inlet of the impactor nozzle 104. Further, in various embodiments, the one or more sidewalls of both the first nozzle component 141 and the second nozzle component 142 may be configured so as to engage one another in order to define the plurality of sidewalls of the impactor nozzle 104. For example, as illustrated, the first nozzle component 141 is engaged with the second nozzle component 142 such that the two first nozzle component sidewalls 141A, 141B and the two second nozzle component sidewalls 142A, 142B collectively define the plurality of sidewalls of the impactor nozzle 104. The two first nozzle component sidewalls 141A, 141B and the two second nozzle component sidewalls 142A, 142B may be arranged so as to collectively define a first nozzle portion, a second nozzle portion, and the nozzle outlet.

Figure 20A:
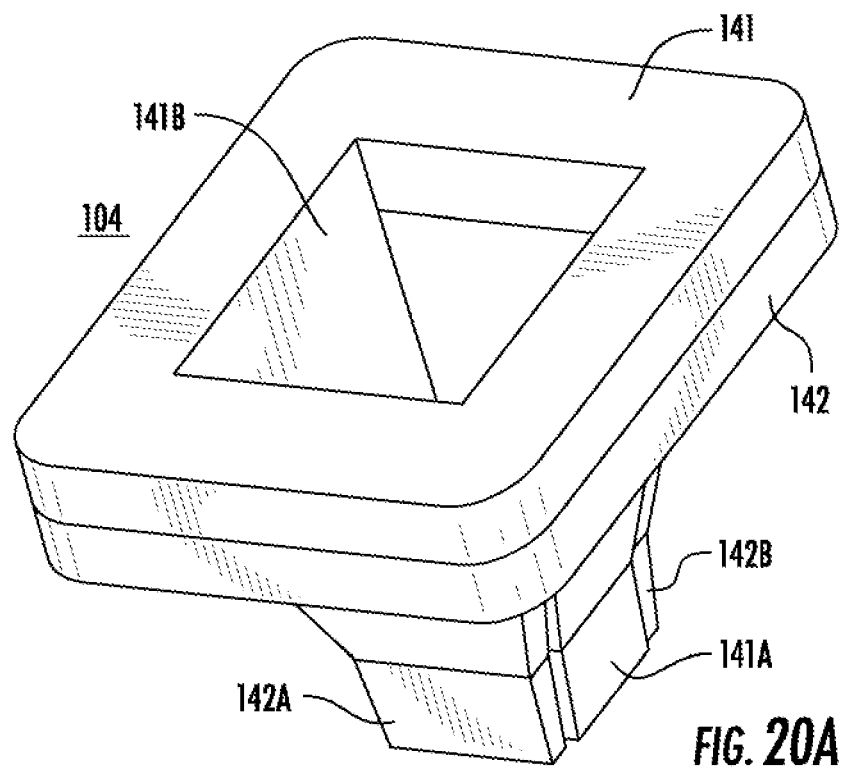
FIGS. 20A-20B illustrate various views of an exemplary apparatus in accordance with various embodiments.
Figure 20B:
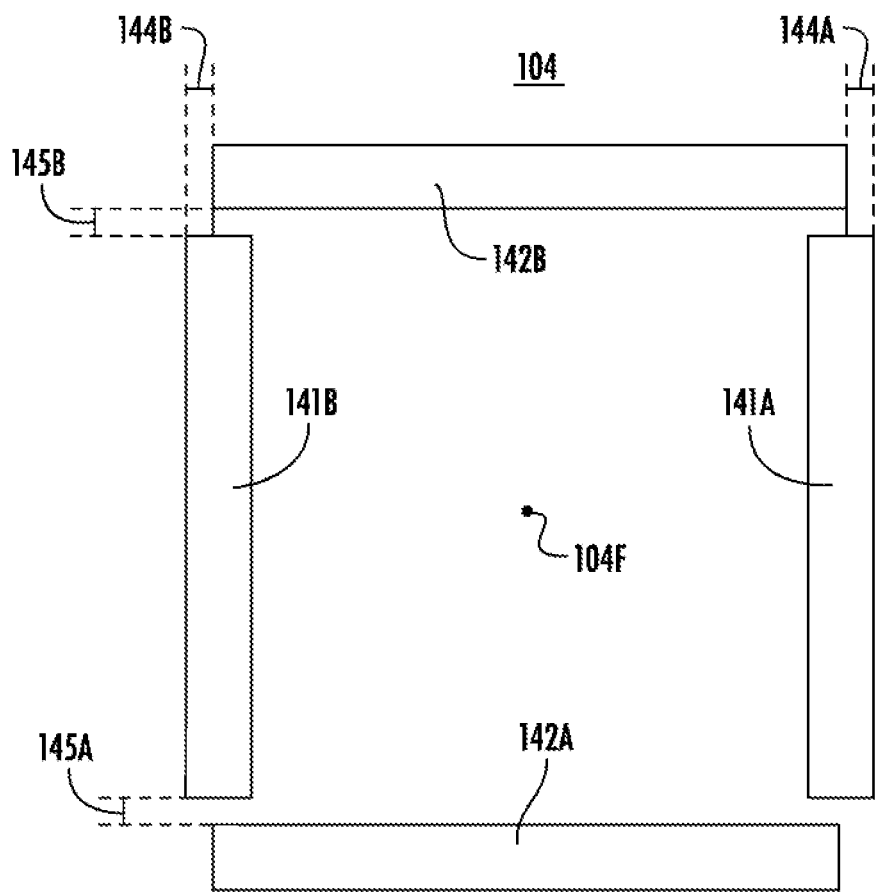

FIGS. 20A-20B illustrate an exemplary impactor nozzle configuration in accordance with various embodiments described herein. In particular, FIGS. 20A-20B illustrate an exemplary impactor nozzle configuration wherein one or more of the plurality of sidewalls may be selectively reconfigured. In various embodiments, as described herein, an exemplary impactor nozzle may be selectively reconfigured (e.g., from a first nozzle configuration to a second nozzle configuration) based at least in part on one or more environmental circumstances. For example, in an exemplary embodiment described herein in reference to FIG. 18D, an impactor nozzle 104 may be selectively reconfigured from a first nozzle configuration to a second nozzle configuration at least in part by laterally moving at least a portion of one or more of the plurality of sidewalls of the impactor nozzle in an outward direction (e.g., away from a central nozzle axis) to increase the nozzle outlet cross-sectional area and/or the intermediate cross-sectional area so as to effectively widen at least a portion of the impactor nozzle 104.

As illustrated in FIG. 20A, an impactor nozzle 104 may be configured such that at least a portion of each of the two first nozzle component sidewalls 141A, 141B and the two second nozzle component sidewalls 142A, 142B, collectively defining the plurality of sidewalls of the impactor nozzle 104, may be independently moveable relative to a central nozzle axis of the impactor nozzle 104. As shown, each of the plurality of sidewalls (e.g., the two first nozzle component sidewalls 141A, 141B and the two second nozzle component sidewalls 142A, 142B) of the exemplary impactor nozzle 104 of has been laterally displaced in an outward direction.

FIG. 20B illustrates a top cross-sectional view of the exemplary impactor nozzle 104 defined at least in part by a nozzle configuration wherein each of the plurality of sidewalls has been laterally displaced in an outward direction away from the central nozzle axis 104F. Each of plurality of sidewalls of the impactor nozzle 104 may move at least substantially independently from each of the other sidewalls of the plurality of sidewalls. For example, as shown, the configuration of first nozzle component sidewall 141A may define a first sidewall displacement distance 144A, the first sidewall displacement distance 144A extending in an outward direction from the central nozzle axis 104F. Further, as shown, the configuration of first nozzle component sidewall 141B may define a second sidewall displacement distance 144B, the second sidewall displacement distance 144B extending in an outward direction from the central nozzle axis 104F. As shown, the configuration of second nozzle component sidewall 142A may define a third sidewall displacement distance 145A, the third sidewall displacement distance 145A extending in an outward direction from the central nozzle axis 104F. Additionally, as shown, the configuration of second nozzle component sidewall 142B may define a fourth sidewall displacement distance 145B, the fourth sidewall displacement distance 145B extending in an outward direction from the central nozzle axis 104F. In various embodiments, the sidewall displacement distances 144A, 144B, 145A, 145B may comprise either the same or different distances.

Particle Impaction Depth

As discussed herein, each of the one or more particles of the plurality of particles 120 may comprise one or more particles characteristics, such as, for example, particle size, particle mass, particle density, particle velocity (e.g., particle linear velocity), particle cross-sectional area, and particle shape. In various embodiments, a particle size of a particle may be approximated based on a particle diameter. In various embodiments, the particle velocity of a particle may be approximated based at least in part on a known flow rate of fluid moving through the device 10. In various embodiments, a particle travelling at a particle velocity in an air flow direction 130 towards the collection media 106 may further comprise a particle momentum, which may be affected at least in part by the one or more particle characteristics. When a particle is at a receiving surface 105 of the collection media 106, the particle may define an initial momentum. The depth at which the particle is subsequently embedded into the collection media (i.e. a particle impaction depth 121) is directly related at least in part to the initial momentum of the particle. In various embodiments, the particle impaction depth 121 may be related to the particle size, the particle mass, and the particle velocity.

As illustrated in FIG. 2, each particle of the plurality of particles 120 within the collection media 106 may further define both an impaction depth 121 and a depth of focus 122. In various embodiments, an impaction depth 121 of a particle may comprise the distance between a receiving surface 105 of the collection media 106 and the location at which the particle is stopped within the collection media 106. As described herein, the particle may travel in an air flow direction 130 through the receiving surface 105 at a velocity and become lodged within the collection media 106 before reaching the backside 107. The depth at which the particle is embedded into the collection media 106 may define the impaction depth 121 of the particle. The impaction depth 121 of a particle may be correlated to at least an initial momentum of the particle at the receiving surface 105 of the collection media that must be dissipated by the collection media 106. In various embodiments, the impaction depth 121 of a particle may be affected by a collection media type, a particle shape (e.g., a particle cross-sectional area, a particle orientation), an ambient temperature, and/or an ambient humidity. In various embodiments, for example, a compensation factor may be applied to the estimated mass of a particle to account for the particle cross-sectional area because a larger particle cross-sectional area will disperse kinetic energy more quickly within the collection media, thereby decreasing the particle impaction depth. In various embodiments, a compensation factor may be applied to the estimated mass of a particle to account for the ambient temperature and/or ambient humidity because both the ambient temperature and ambient humidity affect the viscosity of the collection media, and therefore, may either increase or decrease the resistance force experienced by a particle from a collection media, thereby affecting the particle impaction depth. In various embodiments, the ambient temperature and humidity may be measured by either the device or one or more remote sensors configured to transmit temperature and humidity data to the device.

In various embodiments, the impaction depth 121 of one or more particles of the plurality of particles 120 may be determined by the controller 200 based at least in part on a depth of focus 122. In various embodiments, the impaction depth 121 of a particle within the collection media 106 may be calculated by subtracting the measured depth of focus 122 of a particle from the sum of the collection media thickness, the transparent substrate thickness, and the distance between the transparent substrate 108 and the imaging device 110. In various embodiments, the depth of focus 122 of a particle may comprise the distance between an imaging device 110 and the location at which the particle is stopped within the collection media 106. In various embodiments, as shown in FIG. 2, the depth of focus 122 of a particle within the collection media 106 may comprise the sum of the distance between the location at which the particle is stopped within the collection media 106 and a backside 107 of the collection media 106, the thickness of the transparent substrate 108, and the distance between the transparent substrate 108 and the imaging device 110. In various embodiments, the depth of focus 122 of one or more particles of the plurality of particles 120 may be determined by the controller 200 using one or more image focusing techniques, such as, a computational technique (e.g., Angular Spectrum Propagation (ASP)) or a mechanical technique (e.g., opto-mechanical adjustment). In various embodiments, opto-mechanical adjustment may comprise the mechanical adjustment of one or more components of a lens-based imaging device 110 so as to optimize a particle image. In various embodiments, may further comprise collecting data corresponding to the adjustment of the one or more components of the imaging device in order to determine a depth of focus.

Controller

Figure 3:
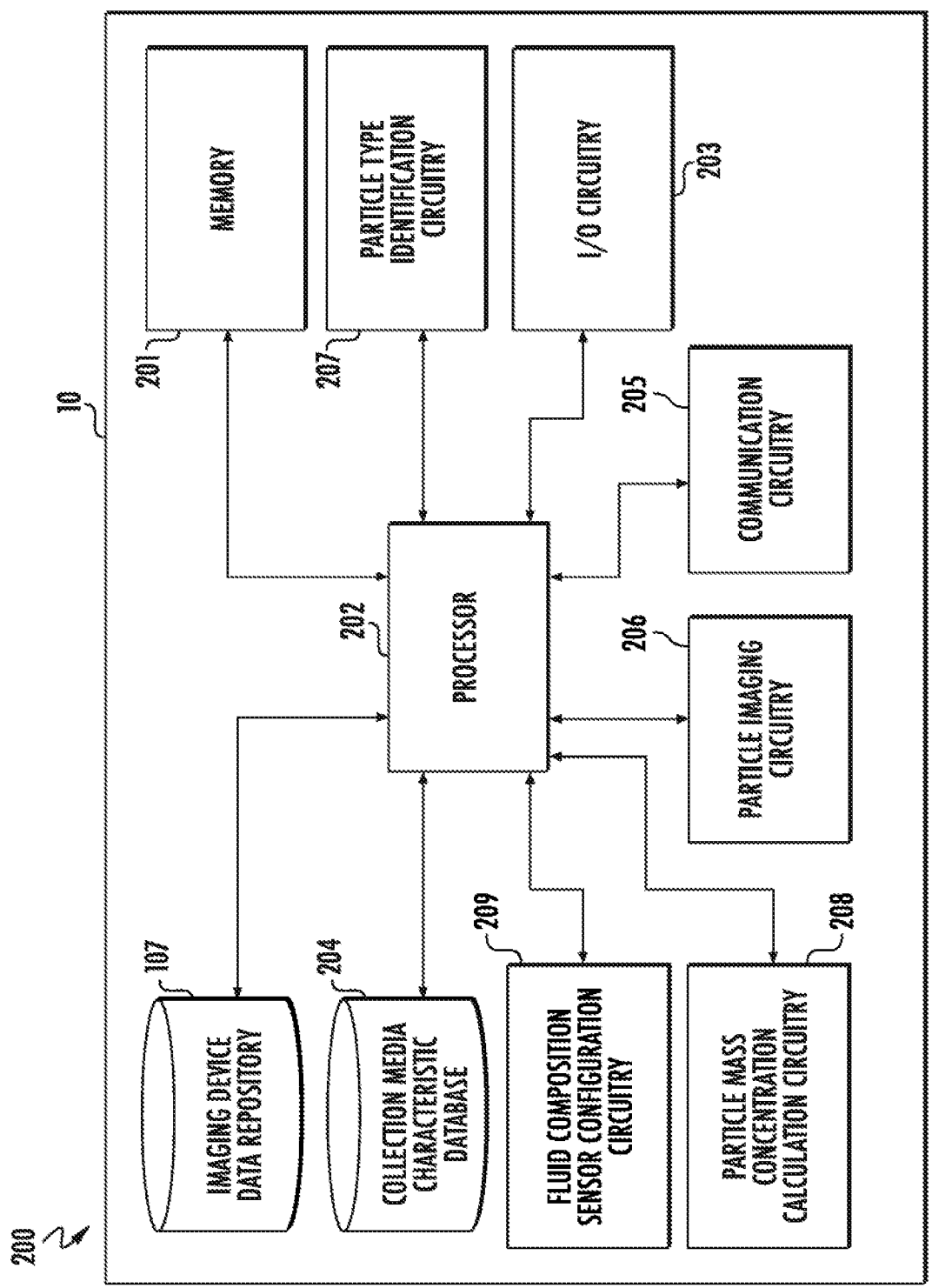
FIG. 3 schematically illustrates an exemplary apparatus for implementing various embodiments of the present disclosure.

As shown in FIGS. 1-3, the device 10 may comprise a controller 200 configured to determine a particle impaction depth 121 of each of the one or more particles of the plurality of particles 120 within the collection media 106, and based at least in part on the particle impaction depth 121 of each of the one or more particles of the plurality of particles 120, determine an approximate collective mass of the plurality of particles present within the volume of fluid. As illustrated in FIG. 3, the controller 200 may comprise a memory 201, a processor 202, input/output circuitry 203, communication circuitry 205, an imaging device data repository 107, a collection media characteristic database 204, particle imaging circuitry 206, particle type identification circuitry 207, particle mass concentration calculation circuitry 208, and fluid composition sensor configuration circuitry 209. The controller 200 may be configured to execute the operations described herein. Although the components are described with respect to functional limitations, it should be understood that the particular implementations necessarily include the use of particular hardware. It should also be understood that certain of the components described herein may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the controller 200 should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the controller 200 may provide or supplement the functionality of particular circuitry. For example, the processor 202 may provide processing functionality, the memory 201 may provide storage functionality, the communications circuitry 205 may provide network interface functionality, and the like.

In some embodiments, the processor 202 (and/or co-processor or any other processing circuitry assisting or otherwise associated with the processor) may be in communication with the memory 201 via a bus for passing information among components of the apparatus. The memory 201 may be non-transitory and may include, for example, one or more volatile and/or non-volatile memories. For example, the memory 201 may be an electronic storage device (e.g., a computer readable storage medium). In various embodiments, the memory 201 may be configured to store information, data, content, applications, instructions, or the like, for enabling the apparatus to carry out various functions in accordance with example embodiments of the present disclosure. It will be understood that the memory 201 may be configured to store partially or wholly any electronic information, data, data structures, embodiments, examples, figures, processes, operations, techniques, algorithms, instructions, systems, apparatuses, methods, look-up tables, or computer program products described herein, or any combination thereof. As a non-limiting example, the memory 201 may be configured to store particle size data, particle type data, particle impaction depth data, particle image data, particle shape data, particle cross-sectional area data, particle mass data, particle density data, and particulate matter mass concentration data associated with a volume of fluid. In various embodiments, the memory may be further configured to store one or more particle impaction depth-momentum look-up tables.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 202 may be configured to execute instructions stored in the memory 201 or otherwise accessible to the processor. Alternatively, or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present disclosure while configured accordingly. Alternatively, as another example, when the processor is embodied as an executor of software instructions, the instructions may specifically configure the processor to perform the algorithms and/or operations described herein when the instructions are executed.

In some embodiments, the controller 200 may include input-output circuitry 203 that may, in turn, be in communication with the processor 202 to provide output to the user and, in some embodiments, to receive input such as a command provided by the user. The input-output circuitry 203 may comprise a user interface, such as a graphical user interface (GUI), and may include a display that may include a web user interface, a GUI application, a mobile application, a client device, or any other suitable hardware or software. In some embodiments, the input-output circuitry 203 may also include a display device, a display screen, user input elements, such as a touch screen, touch areas, soft keys, a keyboard, a mouse, a microphone, a speaker (e.g., a buzzer), a light emitting device (e.g., a red light emitting diode (LED), a green LED, a blue LED, a white LED, an infrared (IR) LED, an ultraviolet (UV) LED, or a combination thereof), or other input-output mechanisms. The processor 202, input-output circuitry 203 (which may utilize the processing circuitry), or both may be configured to control one or more functions of one or more user interface elements through computer-executable program code instructions (e.g., software, firmware) stored in a non-transitory computer-readable storage medium (e.g., memory 201). Input-output circuitry 203 is optional and, in some embodiments, the controller 200 may not include input-output circuitry. For example, where the controller 200 does not interact directly with the user, the controller 200 may generate user interface data for display by one or more other devices with which one or more users directly interact and transmit the generated user interface data to one or more of those devices. For example, the controller 200, using user interface circuitry may generate user interface data for display by one or more display devices and transmit the generated user interface data to those display devices.

The communications circuitry 205 may be a device or circuitry embodied in either hardware or a combination of hardware and software that is configured to receive and/or transmit data from/to a network and/or any other device, circuitry, or module in communication with the apparatus 200. For example, the communications circuitry 205 may be configured to communicate with one or more computing devices via wired (e.g., USB) or wireless (e.g., Bluetooth, Wi-Fi, cellular, and/or the like) communication protocols.

In various embodiments, the processor 202 may be configured to communicate with the particle imaging circuitry 206. The particle imaging circuitry 206 may be a device or circuitry embodied in either hardware or a combination of hardware and software that is configured to receive, process, generate, and/or transmit data, such as an image captured by the imaging device 110. In various embodiments, the particle imaging circuitry 206 may be configured to analyze one or more images captured by the imaging device 110 of the fluid composition sensor 100 to determine which particles of the plurality of particles 120 present within the collection media 106 were newly received by the collection media 106 during a recent particle analysis. The particle imaging circuitry 206 may receive from the imaging device a first captured particle image and a second captured particle image, captured at a first time and a second time, respectively, wherein the first time represents the start of an analysis of the one or more particles of the plurality of particles 120 captured by the collection media 106 by the device 10 and the second time is subsequent the first time (occurs after the first time). In such a configuration, the device may be configured to distinguish between particles present within the collection media 106 at the start of the particle analysis and particles that were newly received by the collection media 106 by comparing the respective particle images captured at the first and second times and identifying any particles from the second captured particle image that were not captured in the first captured particle image. In various embodiments, the particle imaging circuitry 206 may be further configured to analyze one or more images captured by the imaging device 110 of the fluid composition sensor 100 to determine the size of each of the one or more particles of the plurality of particles 120 within the collection media 106. In various embodiments, the size of a particle may be defined by the cross-sectional area of the particle. In various embodiments, the particle imaging circuitry 206 may be configured to determine the particle size of particles with any of a variety of particle sizes. As an example, the particle imaging circuitry 206 may be configured to determine particle sizes of particles having a diameter of between about 0.3 and about 100 microns (e.g., 2.5 microns), and thus, a size category with which the particle may be associated, such as, for example, PM10, PM4, PM2.5, or PM1. In various embodiments, the controller and/or the particle imaging circuitry 206 may be further configured to analyze one or more images captured by the imaging device 110 of the fluid composition sensor 100 to determine the shape of each of the one or more particles of the plurality of particles 120 within the collection media 106. In various embodiments, a particle shape may be defined at least in part by a particle cross-sectional area. The particle imaging circuitry 206 may be further configured to determine the particle impaction depth 121 of each of the one or more particles of the plurality of particles 120 within the collection media 106 using one or more image focusing techniques. The particle imaging circuitry 206 may be configured to execute instructions stored, for example, in the memory 201 for carrying out the one or more image focusing techniques. In various embodiments, the one or more image focusing techniques may comprise one or computational techniques, such as, for example, Angular Spectrum Propagation (ASP). In other embodiments, opto-mechanical adjustment may be used as an image focusing technique. In various embodiments, the particle imaging circuitry 206 may use the one or more image focusing techniques to determine a depth of focus 122 for each of the one or more particles of the plurality of particles 120 within the collection media. Upon determining a depth of focus for each of the one or more particles, the particle imaging circuitry 206 may be configured to calculate, using known dimensions of the fluid composition sensor 100 such as, for example, the collection media thickness and the distance between the transparent substrate 108 and the imaging device 110, the impaction depth 121 of each of the one or more particles of the plurality of particles 120 within the collection media 106. In various embodiments, for example, the impaction depth 121 of a particle within the collection media 106 may be calculated by subtracting the measured depth of focus 122 of a particle from the sum of the collection media thickness, the transparent substrate thickness, and the distance between the transparent substrate 108 and the imaging device 110. The particle imaging circuitry 206 may send and/or receive data from the imaging device data repository 107. In various embodiments, the particle imaging circuitry 206 may be configured to determine an impaction depth of a particle using one or more machine learning techniques. In various embodiments, the one or more machine learning techniques used by the particle imaging circuitry 206 to determine the impaction depth of a particle may comprise using deep supervised learning with one or more labeled datasets of one or more known particle characteristics, such as, for example, particle type, particle velocity, particle size, particle shape, and/or any other data generated, transmitted, and/or received by the controller 200 to estimate the impaction depth of the particle.

In various embodiments, the processor 202 may be configured to communicate with the particle type identification circuitry 207. The particle type identification circuitry 207 may be a device or circuitry embodied in either hardware or a combination of hardware and software that is configured to identify a particle type and/or particle species of one or more particles of the plurality of particles 120 received by the collection media 106. In various embodiments, a plurality of particles 120 within a volume of fluid may comprise one or more particles of various particle types, such as, for example, one or more of bacteria, pollen, spores, molds, biological particles, soot, inorganic particles, and organic particles. In various embodiments, the particle type identification circuitry 207 may determine the particle type and/or particle species of each of the one or more particles of the plurality of particles 120 received by the collection media 106 using one or more machine learning techniques. In various embodiments, the one or more machine learning techniques used by the particle type identification circuitry 207 to determine the particle type and/or species of each of the one or more particles of the plurality of particles 120 may comprise analyzing an image captured by the imaging device 110, particle size data, particle shape data, and/or any other data generated, transmitted, and/or received by the controller 200. In various embodiments, the particle type identification circuitry 207 may send and/or receive data from the imaging device data repository 107. Further, in various embodiments, the particle type identification circuitry 207 may be configured to receive the determined particle initial velocity data corresponding to one or more of the particles of the plurality of particles 120 received by the collection media 106 from the particle matter mass concentration calculation circuitry 208. In various embodiments, the particle type identification circuitry 207 may be configured to compare the determined particle initial velocity for a particle to the particle velocity approximated based at least in part on a known flow rate of fluid moving through the fluid composition sensor 100 and generate velocity comparison data associated with the particle. In various embodiments, the particle type identification circuitry 207 may be configured execute a feedback loop, wherein one or more velocity comparison data associated with one or more particles of the plurality of particles 120 received by the collection media 106 may define one or more inputs into a machine learning model in order to increase a rate of machine learning associated with the one or more machine learning techniques, as described herein.

In various embodiments, the device 10 may be configured with, or in communication with, a collection media characteristic database 204. The collection media characteristic database 204 may be stored, at least partially on the memory 201 of the system. In some embodiments, the collection media characteristic database 204 may be remote from, but in connection with, the device 10. The collection media characteristic database 204 may contain information, such as one or more particle impaction depth-momentum relationship look-up tables. In various embodiments, a particle impaction depth-momentum relationship look-up table may comprise a data matrix used to define a relationship between a particle impaction depth and a particle initial momentum (i.e. the momentum of a particle at a receiving surface 105 of the collection media 106, wherein the particle is received by the collection media 106 at the receiving surface 105, as described herein) for a particular collection media type. Various particle impaction depth-momentum relationship look-up tables may comprise data matrices used to define a relationship between a particle impaction depth and a particle initial momentum for various collection media types.

The particle matter mass concentration calculation circuitry 208 may be a device or circuitry embodied in either hardware or a combination of hardware and software that is configured to determine a particulate matter mass concentration within a volume of fluid. In various embodiments, the particle matter mass concentration calculation circuitry 208 may be configured to determine the particulate matter mass concentration within a volume of fluid based on an approximated collective mass of a plurality of particles present within the volume of fluid. In various embodiments, the particle matter mass concentration calculation circuitry 208 may be configured to determine the approximated collective mass of a plurality of particles present within the volume of fluid based on a collective mass of the plurality of particles 120 received by the collection media 106. In various embodiments, the particle matter mass concentration calculation circuitry 208 may be configured to determine a collective mass of the plurality of particles 120 received by the collection media 106 based on the respective estimated masses of each of the particles of the plurality of particles 120. In various embodiments, the particle matter mass concentration calculation circuitry 208 may be configured to estimate the respective masses of each of the particles of the plurality of particles 120 based at least in part on the respective determined impaction depths of each particle.

In various embodiments, the particle matter mass concentration calculation circuitry 208 may be configured to estimate the mass of a particle of the plurality of particles 120 by retrieving data corresponding to a particle such as, for example, particle size data, particle shape data (e.g., particle cross-sectional area data, particle orientation data), and particle impaction depth, and, based on data in a particle impaction depth-momentum look-up table that correlates particle impaction depth to particle initial momentum for a given collection media 106 type, determine the initial momentum of the particle prior to the particle being received by the collection media 106. Using a known relationship between momentum, velocity, and mass—the momentum of a particle is equal to the mass of the particle multiplied by the velocity of the particle—and the known velocity of the particle—a controlled value based on an air flow velocity within the device 10—the particle matter mass concentration calculation circuitry 208 may be configured to determine the estimated mass of the particle.

In various embodiments, the particle matter mass concentration calculation circuitry 208 may be configured to determine the estimated mass of the particle using one or more machine learning techniques. In various embodiments, the one or more machine learning techniques used by the particle matter mass concentration calculation circuitry 208 to determine the particle mass of a particle may comprise using deep supervised learning with one or more labeled datasets of one or more known particle characteristics, such as, for example, particle type, particle velocity, particle impaction depth, various particle gravimetric measurements, and/or any other data generated, transmitted, and/or received by the controller 200 to estimate the mass of the particle. In various embodiments, the particle matter mass concentration calculation circuitry 208 may be configured to apply one or more compensation factors to a determined particle mass using one or more machine learning techniques.

Further, in various embodiments, the particle matter mass concentration calculation circuitry 208 may be configured to determine the estimated density of the particle based at least in part on one or more of the particle impaction depth, the estimated particle mass, the particle shape, the particle type, and the particle size data. In various embodiments, the particle matter mass concentration calculation circuitry 208 may be configured to determine the estimated mass and/or density of each of the particles of the plurality of particles 120 received by the collection media 106. In various embodiments, the particle matter mass concentration calculation circuitry 208 may be configured to apply one or more compensation factors to the estimated mass of the particle to account for one or both of a particle condition associated with the particle and ambient conditions associated with the ambient environment. In various embodiments, for example, the particle matter mass concentration calculation circuitry 208 may be configured to apply an appropriate compensation factor based at least in part on the particle cross-sectional area, the ambient temperature, and/or the ambient humidity. In various embodiments, the particle matter mass concentration calculation circuitry 208 may be configured to determine the estimated collective mass of the plurality of particles 120 received by the collection media based on the estimated mass of each of the particles of the plurality of particles 120 received by the collection media 106. In various embodiments, the particle matter mass concentration calculation circuitry 208 may be configured to determine the approximate collective mass of a plurality of particles present within the volume of fluid based on a determined collective mass of the plurality of particles 120 received by the collection media 106. In various embodiments, the particle matter mass concentration calculation circuitry 208 may be configured to determine the particulate matter mass concentration within the volume of fluid based on the approximate collective mass of the plurality of particles present within the volume of fluid. In various embodiments, the particle matter mass concentration calculation circuitry 208 may be configured to apply one or more scale factors to the determined particulate matter mass concentration within the volume of fluid to account for experimental inefficiencies such as, for example, particle collection efficiencies and detection probability factors. In various embodiments, an appropriate scale factor may be determined based on empirical data.

Moreover, the particle matter mass concentration calculation circuitry 208 may be configured to determine that the collection media 106 needs to be replaced. For example, in various embodiments, the particle matter mass concentration calculation circuitry 208 may be configured to determine that a threshold amount of time has passed since the collection media 106 was last replaced, that the number of particles present within the collection media 106 has surpassed a predetermined threshold number of particles, and/or that a percentage of particle coverage within a field of view has surpassed threshold particle coverage percentage.

In various embodiments, the device 10 may be configured to determine an amount of time for which a device 10 (e.g., a pump 112) should remain in operation by drawing fluid through the device 10 so as to cause at least a predetermined volume of fluid to be directed toward (e.g., pass across a surface of) a collection media 106. The predetermined volume of fluid may be defined by a threshold volume of fluid (e.g., a minimum volume of fluid, a maximum volume of fluid) or an acceptable range of fluid volume (e.g., between a minimum and a maximum volume of fluid). In certain embodiments, the volume of fluid passing through the device 10 may be measured (e.g., by a fluid flow sensor), however in other embodiments the volume of fluid passing through the device 10 may be estimated (e.g., based on a known fluid flow rate) while the pump is in an operating configuration and an amount of time the pump is in the operational configuration. For example, in various embodiments, the particle matter mass concentration calculation circuitry 208 may be configured to generate and/or transmit one or more signals so as to cause the fluid composition sensor 110 to initiate a particle collection operation, as described herein, wherein the sensor 110 may receive a volume of fluid comprising a plurality of particles and facilitate the engagement of a collection media 106 by the received volume of fluid such that at least a portion of the plurality of particles within the volume of fluid may be disposed at and/or into the collection media 106. For example, in various embodiments, particle matter mass concentration calculation circuitry 208 may be configured to emit one or more signals so as to cause a pump 112 to transition from an "OFF" configuration to an "ON" operational configuration. Conversely, in various embodiments, the particle matter mass concentration calculation circuitry 208 may be configured to emit one or more signals so as to cause a pump 112 to transition from an "ON" operational configuration to an "OFF" configuration. As non-limiting examples, the particle matter mass concentration calculation circuitry 208 may be configured to emit one or more signals so as to cause a pump 112 to transition from an "ON" operational configuration to an "OFF" configuration based at least in part on a determination that a threshold amount of time has elapsed and/or a threshold volume of fluid has been received by the fluid composition sensor 110 during an operation state. In various embodiments, such a determination may be made by the particle matter mass concentration calculation circuitry 208 based at least in part on data collected by a fluid flow sensor of the fluid composition sensor 110 that is configured to detect the flow rate of a volume of fluid passing through at least a portion of the sensor 110. In various embodiments, the fan or pump 112 is calibrated, such that the flow rate of fluid moving through the device is known/determined based at least in part on the operating characteristics (e.g., operating power) of the fan or pump 112.

In some embodiments, the device 10 includes a fluid composition sensor 110 configured to receive a volume of fluid having: a collection media 106 housing configured to receive and secure at least a portion of a collection media 106 for receiving one or more particles of a plurality of particles within the volume of fluid; a pump 112 to move a volume of fluid over the collection media 106 housing; an imaging device 110 configured to capture an image of at least a portion of one or more particles of the plurality of particles received by the at least one collection media 106; and a particle matter mass concentration calculation circuitry 208 connected with the imaging device 110 and the pump 112. The particle matter mass concentration calculation circuitry 208 is configured to calculate a total particle matter mass of one or more particles of the plurality of particles received by the at least one collection media 106 based on the image thereof. The particle matter mass concentration calculation circuitry 208 is configured to adjust the volume of fluid over the collection media 106 housing.

In various embodiments, as described herein, the particle mass concentration calculation circuitry 208 may be configured to adjust the operation of a fluid composition sensor 110, for example, by causing one or more operational characteristics of the fluid composition sensor 110 (e.g., pump on/off configuration, pump volumetric flow rate, and/or the like) to be adjusted. For example, the particle mass concentration calculation circuitry 208 may be configured to adjust the operation of a pump 112 of the fluid composition sensor 110, for example, by causing one or more operational characteristics of the pump 112 to be adjusted (e.g., stopped) before the collection media 106 has captured a quantity of particles that deteriorates the accuracy of the measurements of future captured particles (e.g., because the collection media is sufficiently filled with particles that newly captured particles cannot be identified and/or edges of those particles cannot be accurately located). For example, as described herein, a fluid composition sensor 110 configured to receive a volume of fluid comprising a plurality of particles such that at least a portion of the particles become disposed on and/or in a collection media 106, and further to determine a at least one of a particle matter mass, particle coverage percentage, and/or any other particle load condition defined by the plurality of particles disposed at the collection media 106, may experience increased inaccuracies caused by measurement errors arising from the physical saturation and/or deterioration of the collection media over time due to prolonged collection of a plurality of particles. In various embodiments, a particle load condition as described herein may be defined at least in part by a spatial arrangement of a plurality of particles disposed at a collection media (e.g., particle clustering, spiking, particle touching, particles on top of each other, and/or the like), a particle coverage percentage, an average gray scale of all pixels in a captured image, a particle matter mass, a total light intensity, an amount of collected particles, calculated particle density, and/or the like.

For example, the increased frequency and/or degree of the aforementioned sensor inaccuracies may correspond to an increased quantity of particles collected at the collection media 106 (and the resulting physical properties of the collection media 106 changes as a result of the increase number of particles disposed therein). Accordingly, in various embodiments, one or more components of the collection media assembly (e.g., the collection media 106) as described herein may be replaceable such that a first collection media may be utilized in receiving a first plurality of particles from a first volume of fluid and may be removed from the sensor 110 and replaced with a second collection media that may be subsequently utilized in receiving a second plurality of particles from a second volume of fluid that is received by the sensor 110 after the first collection media is removed therefrom. In such an exemplary circumstance, the reduction of sensor accuracy caused by measurement errors arising from the physical saturation and/or deterioration of the collection media over time may be combatted by replacing an at least partially exhausted collection media with an at least substantially new media having fewer (e.g., zero) particles from a volume of fluid received by the sensor 110 engaged therewith.

In some embodiments, as described herein, the particle mass concentration calculation circuitry 208 may be configured to determine when the plurality of particles received by the collection media 106 is arranged such that at least two of the particles are unevenly spaced, touching, clustered, and/or on top of one another. For example, two or particles of a plurality of particles may be aligned with one another relative to the imaging device in an exemplary circumstance wherein a first particle engages the collection media at a first time and at a first location about the receiving face, and a second particle subsequently engages the collection media at a second time—the second time be chronologically after the first time—and at the first location about the receiving face such that at least a portion of the second particle overlaps at least a portion of the first particle from the perspective of the imaging device. In such an exemplary circumstance, the positioning of the second particle on top of the first particle, as described, may prevent the entirety of the first particle from being captured in an image taken by an exemplary imaging device, and thus, may prevent the controller 200 from accurately analyzing the first particle according to one or more operations described herein. In such an exemplary circumstance, the controller may be configured to determine that a first portion of the plurality of particles at a first portion of the collection media exhibits a first collective particle density that is at least substantially different than a second collective particle density of a second portion of the plurality of particles at a second portion of the collection media, wherein the collective particle density may be defined by the number of particles of the plurality within a given surface area defining a portion of the collection media. In some embodiments, the device 10 (e.g., controller 200 in association with the imaging device) may be configured to actively monitor the spacing of the particles so as to maximize the operational efficiency of the device 10 and/or identify particle placement on the collection media 106.

In various embodiments, the controller 200 (e.g., particle matter mass concentration calculation circuitry 208) may be configured to calculate particle matter mass by at least using an image to calculate the total particle matter mass or to determine the amount of light that extends through the collection media 106. In some embodiments, the particle mass concentration calculation circuitry 208 works with the particle imaging circuitry 206 to determine and/or characterize the spatial arrangement of one or more particles within a field of view of an imaging device, and/or the like, such as, for example, a spacing between particles. For example, in various embodiments, as described herein, an image captured by an exemplary imaging device may comprise a two-dimensional image (e.g., a photograph of at least a portion of the collection media) and/or a three-dimensional image (e.g., a three-dimensional digital reconstruction of at least a portion of the particles captured at the collection media based at least in part on two-dimensional locations of detected particles and focal depths associated with each of the plurality of particles, that may be indicative of a distance away from the imaging device and therefore may be indicative of a third dimensional position of each of the plurality of particles). Accordingly, in various embodiments, the particle mass concentration calculation circuitry 208 may be configured to characterize the spacing between two particles of the plurality of captured particles by an image as a distance between the two particles, wherein distance between the two particles is defined by one or more of an x-component (e.g., a difference in respective x-coordinates), a y-component (e.g., a difference in respective y-coordinates), and a z-component (e.g., a difference in respective z-coordinates, which may be determined by a focal depth relative to an imaging device).

As described herein, the particle mass concentration calculation circuitry 208 may be configured to calculate a percentage of particle coverage of a collection media within a field of view and, further, may determine that the calculated percentage of particle coverage is greater than a threshold particle coverage percentage. In some embodiments, the particle mass concentration calculation circuitry 208 may be configured to calculate the percentage of particle coverage of the collection media 106 based at least in part on a determined percentage of an image (e.g., a percentage of the field of view of an imaging device) that is covered in particles. For example, in various embodiments, a portion of a collection media may be covered by a particle in an exemplary circumstance wherein the particle is disposed at the collection media and wherein a cross-sectional area of the particle is positioned between an imaging device and at least a portion of a thickness of the collection media such that the particle at least partially interrupts the line of sight between the imaging device and the at least a portion of the thickness of the collection media. As a non-limiting example, a plurality of particles received by a collection media may collectively cover at least a portion of the collection media. As described herein, the particle mass concentration calculation circuitry 208 may be configured to calculate a percentage of particle coverage of a collection media based at least in part on a comparison of the total surface area of the collection media (e.g., a receiving face) and the surface area of the collection media that is covered by the plurality of particle. In various embodiments, the particle mass concentration calculation circuitry 208 may be configured to determine that the percentage of particle coverage of a collection media is greater than a predetermined threshold. As a non-limiting example, in various embodiments, a predetermined threshold of percentage of particle coverage may be at least approximately between 0.01% and 99.9%. In such an exemplary circumstance, the particle mass concentration calculation circuitry 208 may be configured to identify the collection media as "covered," and accordingly generate one or more signals configured to cause the adjustment of the operation of the fluid composition sensor, so as to facilitate the replacement of the covered collection media. As a non-limiting illustrative example, the predetermined threshold of percentage of particle coverage may be less than 1% in an exemplary circumstance wherein detecting the controller 200 is configured to detect the presence of a single particle, such as, for example, in a circumstance related to a "clean room" application.

In some embodiments, the particle mass concentration calculation circuitry 208 may be configured to determine if at least a portion of the plurality of the particles received by the fluid composition sensor 110 are clustering at the collection media 106 based at least in part on one or more images of the collection media 106. In various embodiments, the particle mass concentration calculation circuitry 208 may be configured to determine that a plurality of particles received by a fluid composition sensor 110 are clustered such that boundaries of the plurality of particles are at least substantially overlapping or are spaced less than a clustering threshold distance to define individual clusters, and a plurality of clusters (each comprising a plurality of particles having overlapping boundaries) are spaced a distance apart (such that individual clusters are separated and discrete from one another) where a first portion of the collection media exhibits a first particle coverage percentage, as described above, that is disproportionate relative to a second particle coverage percentage detected at a second portion of the collection media. For example, in some embodiments, the particle mass concentration calculation circuitry 208 may be configured to determine if the particles are clustering by calculating the average distance between at least a portion of the particles. In some embodiments, the particle mass concentration calculation circuitry 208 is configured to determine that at least a portion of the plurality of the particles received by the fluid composition sensor 110 are clustering based at least in part on a determination that the calculated average distance between the particles at the collection media 106—as represented in an image—is below a predetermined distance. For example, in some embodiments, the particle mass concentration calculation circuitry 208 is configured to determine when a percentage of the distances between particles is below a predetermined distance. In some embodiments, the particle mass concentration calculation circuitry 208 is configured to cause (e.g., by transmitting one or more signals) the fluid composition sensor 110 to adjust the volume of fluid flowing over the collection media 106, such as, for example, by stopping the pump 112. In some embodiments, the particle mass concentration calculation circuitry 208 is configured to provide a signal when it is determined that the particles are clustering.

In some embodiments, the signal is connected to a display device. In some embodiments, the signal provided by the particle mass concentration calculation circuitry 208 may provide a warning that may diagnose that an uneven airflow is present within the device 10.

In various embodiments, the particle matter mass concentration calculation circuitry 208 may be configured to cause the adjustment of the operation of the pump 112 of the fluid composition sensor 110 (e.g., between an on/off configuration, the volumetric flow rate, and/or the like based at least in part on a determination that a predetermined total particle matter mass threshold is reached. For example, the particle matter mass concentration calculation circuitry 208 may be configured to transmit one or more signals that, either directly or indirectly, cause the pump 112 to stop operating upon determining that a predetermined total particle matter mass threshold has been reached.

As a non-limiting example, in various embodiments, particle matter mass concentration calculation circuitry 208 may receive from an imaging device of the device 10 a first captured particle image and a second captured particle image, captured at a first time and a second time, respectively, wherein the first time represents the start of an analysis of the one or more particles of the plurality of particles 120 captured by the collection media 106 by the device 10 and the second time is subsequent the first time (occurs after the first time). In various embodiments, the particle matter mass concentration calculation circuitry 208 is configured to determine a first particle loading condition corresponding to the first image and determine a second particle loading condition corresponding to the second image. In various embodiments, the particle matter mass concentration calculation circuitry 208 is configured to compare the first total particle matter mass to the second total particle matter mass. In various embodiments, the particle matter mass concentration calculation circuitry 208 is configured to calculate a difference in first total particle matter mass and second total particle matter mass. For example, the particle matter mass concentration calculation circuitry 208 may be configured to calculate a difference in first total particle matter mass and second total particle matter mass by identifying any particles from the second captured particle image that were not captured in the first captured particle image. In various embodiments, the particle matter mass concentration calculation circuitry 208 may be configured to cause one or more operational characteristics of the pump 112 of the fluid composition sensor 110 (e.g., on/off configuration, volumetric flow rate, and/or the like) to be adjusted based at least in part on a determination that a calculated difference in first total particle matter mass and second total particle matter mass is more than a predetermined difference. For example, in various embodiments, the particle matter mass concentration calculation circuitry 208 may be configured to stop the pump 112 when a predetermined difference in first total particle matter mass and second total particle matter mass is calculated. In some embodiments, the particle mass concentration calculation circuitry 208 is configured to determine the density of a particle concentration at a collection media 106 based at least in part on a captured particle image. For example, the particle mass concentration calculation circuitry 208 may be configured to compare a calculated particle density to one or more stored particle density thresholds and accordingly cause one or more operational characteristics of the pump 112 to be adjusted based on a determination that the calculated particle density is greater than the particle density threshold. Additionally, or alternatively, the particle mass concentration calculation circuitry 208 may be configured to cause one or more operational characteristics of the pump 112 to be adjusted based on a determination that the calculated particle density is less than a particle density threshold.

In various embodiments, as described herein, the particle matter mass concentration calculation circuitry 208 is configured to determine if the total particle matter mass is clustered. In various embodiments, the imaging device 110 is configured to capture images at a set interval. In various embodiments, the imaging device 110 is configured to capture an image at the start of the flow of the volume of fluid over the collection media 106 housing. In various embodiments, the particle matter mass concentration calculation circuitry 208 is configured to determine if the start of the flow of the volume of fluid causes a spike in one or more particle loading conditions, such as, for example, the particle matter mass. In various embodiments, a spike in a particle loading condition may be defined as a rapid increase in the particle loading condition, such as, for example, a rapid increase in the particle matter mass, with time. As a non-limiting, illustrative example, a spike could be defined as a rate of increase in one or more particle loading conditions that exceeds a defined threshold, such as, for example, a rate of increase of a particle matter mass that is determined to exceed a predetermined rate of particle matter mass increase threshold. In some embodiments, the particle matter mass concentration calculation circuitry 208 is configured to calculate a percent increase in particle matter mass over time, such as, for example, a rate of increase in calculated particle matter mass in successive measurements. In some embodiments, the particle matter mass concentration calculation circuitry 208 is configured to provide a signal indicating that the percent increase in the one or more particle loading conditions over time is above or below a predetermined threshold. As a non-limiting illustrative example, a detection of a spike, as defined herein, by the controller may correspond to a determination that, for example, the imaging device, the collection media, the illumination source, and/or any other component of the fluid composition sensor 110 may have been dirty upon the initiation of the particle collection operation and/or that the device 10 needs to be recalibrated.

In various embodiments, the particle matter mass concentration calculation circuitry 208 may be configured to calculate a total particle matter mass of one or more particles of the plurality of particles received by the at least one collection media 106 based at least in part by determining a total intensity of light across an image captured by an imaging device, as described herein. In various embodiments, the total light intensity may correspond to a measurement based at least in part on an imaging device, such as, for example, a charge coupled device (CCD) image sensor. As a non-limiting illustrative circumstance, the total light intensity may be measured based at least in part on an average bit count of each pixel associated with the imaging device and/or an image produced by the imaging device. For example, an exemplary calculation of total light intensity may be executed as a function of time during an operation whereby the device 10 (e.g., controller 200) measures one or more raw signals from each pixel in a CCD array corresponding to the imaging device. In various embodiments, the total intensity of light—as depicted in an image of the collection media 106 and the plurality of particles received thereby—may be based at least in part on a particle type, an average refractive index, an opacity of a particle at an optimal source wavelength (e.g., 850 nm), and/or the like associated with at least a portion of the plurality of particles captured at the collection media. As a non-limiting, illustrative example, the total intensity of light may be at least substantially inversely proportional to the particle concentration and/or the particle mass matter of the plurality of particles captured in the image (e.g., at the collection media 106 and within the field of view of the imaging device). In various embodiments, the particle matter mass concentration calculation circuitry 208 may be configured to cause the adjustment of the operation of the pump 112 of the fluid composition sensor 110 (e.g., on/off configuration, volumetric flow rate, and/or the like) based at least in part on a determination that a calculated total light intensity is less than a predetermined threshold. For example, in various embodiments, the particle matter mass concentration calculation circuitry 208 may be configured to generate one or more signals configured to cause the pump 112 to stop operating (e.g., to transition from an "ON" operational configuration to an "OFF" configuration) upon determining that the total intensity of light across the image is less than a predetermined intensity threshold.

In various embodiments, the particle matter mass concentration calculation circuitry 208 is configured to determine a total intensity of light across an image captured by an imaging device, wherein the image depicts at least a portion of a collection media using gray scale. In such an exemplary circumstance, an image depicting the collection media using gray scale may include one or more of a plurality of particles disposed at the collection media represented by an indicator, such as, for example, one or more areas of a relatively dark color (e.g., relative to the collection media) so as to distinguish the collection media from the one or more particles disposed thereon. In various embodiments, the size, shape, color, and/or the like of the one or more indicators corresponding to particles of the plurality disposed at the collection media may proportionately vary based at least in part on the collective mass, density, size, and/or the like of the one or more particles corresponding thereto. As a non-limiting example, in some embodiments, the particle matter mass concentration calculation circuitry 208 may be configured to determine a particle coverage percentage based at least in part on the number and/or coverage percentage (e.g., relative to the portion of the collection media depicted in a gray scale image) of the one or more dark spots present in an exemplary gray scale image of a collection media. A calculated total light intensity is less than a predetermined threshold. In some embodiments, the particle matter mass concentration calculation circuitry 208 may be configured to cause one or more operational characteristics of the pump 112 of the fluid composition sensor 110 (e.g., on/off configuration, volumetric flow rate, and/or the like) to be adjusted based at least in part on a determination that the number and/or coverage percentage (e.g., relative to the portion of the collection media depicted in a gray scale image) of the one or more dark spots present an exemplary gray scale image of a collection media. a calculated total light intensity is less than a predetermined threshold.

Various embodiments are directed to a method for detecting fluid particle characteristics comprising: directing the volume of fluid toward a collection media 106, receiving on the collection media 106 one or more particles of a plurality of particles within the volume of fluid; capturing an image of the one or more particles of the plurality of particles received by the collection media 106; determining a total particle matter mass of one or more particles of the plurality of particles received by the at least one collection media 106 based on the image thereof; and adjusting the volume of fluid.

In various embodiments, the total particle matter mass is determined by a particle matter mass concentration calculation circuitry 208 configured to operate together with a controller to adjust the volume of fluid passing over the collection media 106 and/or through the device 10 housing. In various embodiments, the particle matter mass concentration calculation circuitry 208 is configured to adjust the volume of fluid passing over the collection media 106 housing when a predetermined difference in a first total particle matter mass and a second total particle matter mass is calculated. In various embodiments, the particle matter mass concentration calculation circuitry 208 is configured to adjust the volume of fluid over the collection media 106 housing when the total intensity of light across the image is diminished to a predetermined threshold. In various embodiments, the pump 112 continues to operate to draw air through the device 10 as long as the intensity picture or light scale is above a predetermined threshold.

In various embodiments, one or more predetermined threshold values such as, for example, a particle coverage threshold, a particle separation threshold, a light intensity threshold, and/or the like, may be received by the fluid composition sensor 110 (e.g., the controller 200) as user input provided via a user interface. For example, in some embodiments, user input received by a controller 200 may be transmitted to the particle matter mass concentration calculation circuitry 208 and may comprise a fluid and/or material being sampled. In such an exemplary circumstance, the particle matter mass concentration calculation circuitry 208 may be configured to identify a corresponding predetermined threshold based at least in part on one or more look-up tables stored in memory 202 and associated with the user-selected fluid and/or material. As a non-limiting example provided by way of illustration, the particle matter mass concentration calculation circuitry 208 may be configured to receive a signal corresponding to a user selection of a material such as silica dust, which may be at least partially transparent to a wavelength of an exemplary light beam emitted from an illumination source within an exemplary fluid composition sensor, as described herein. In such an exemplary circumstance, the particle matter mass concentration calculation circuitry 208 may identify a corresponding light intensity threshold value using data stored in the memory (e.g., a look-up table). In various embodiments, the light intensity threshold identified as corresponding to the at least partially transparent silica dust material may vary from (e.g., may be less than) a light intensity threshold corresponding to a non-transparent material based at least in part on a contrast between covered and non-covered portions of the collection media, as described herein. As a further non-limiting example, a light intensity threshold identified as corresponding to a non-transparent material, such as, for example, volcanic ash or fire soot, may vary from (e.g., may be greater than) a light intensity threshold corresponding to an at least partially transparent material based at least in part on a contrast between covered and non-covered portions of the collection media.

In various embodiments, a fluid composition sensor comprising a controller (e.g., particle matter mass concentration calculation circuitry 208) configured to calculate total particle matter mass of a plurality of particles received from within a volume of fluid by a collection media and characterize the spatial arrangement of the plurality of particles so as to identify one or more particle configurations known to negatively affect sensor accuracy and/or sensor effectiveness over time (e.g., lifespan), such as, for example, particle clustering, spiking, particle touching, particles on top of each other, and/or a collection media "covered" by particles, may facilitate the prevention of sensor inaccuracies caused by overloading an exhausted and/or compromised collection media with a particle loading condition that cannot accurately be determined and/or identified by the sensor. Such an exemplary configuration substantially minimizes the amount of retesting required to obtain accurate data and prevents over-use of the fluid composition sensor by defining operational parameters configured to substantially autonomously limit the operation of the sensor upon identifying the presence of one or more of the aforementioned error-inducing particle load conditions. By dynamically monitoring the load condition of the plurality of particles received by the collection media and optimizing the operational parameters so as to selectively limit the run time of the device, the longevity of the device may be increased. Further, the device as described herein may further simplify the calculation of the requisite operational run time of the fluid composition sensor needed to a sample of particles sufficient to provide one or more statistically significant measurements.

Further, in various embodiments, the particle matter mass concentration calculation circuitry 208 may be configured to determine a particle initial velocity for one or more particles of the plurality of particles 120 received by the collection media 106 based at least in part the determined particle mass of the particle, wherein the particle initial velocity is a velocity of the particle at the receiving surface 105 of the collection media 106. In various embodiments, the particle matter mass concentration calculation circuitry 208 may be configured to transmit the determined particle initial velocity data corresponding to one or more of the particles of the plurality of particles 120 received by the collection media 106 to the particle type identification circuitry 207.

The fluid composition sensor configuration circuitry 209 may be a device or circuitry embodied in either hardware or a combination of hardware and software that is configured to control the selective configuration of one or more selectively configurable components of a fluid composition sensor. In various embodiments, the fluid composition sensor configuration circuitry 209 may configure the fluid composition sensor between an open configuration and a closed configuration, as described herein. Further, in various embodiments, the fluid composition sensor configuration circuitry 209 may facilitate the automated reconfiguration of one or more collection media assemblies, as described herein. In various embodiments, the fluid composition sensor configuration circuitry 209 may selectively configure between an open configuration and a closed configuration a dispense door and/or a deposit door of one or more collection media assembly storage chambers of a fluid composition sensor. Further, in various embodiments, the fluid composition sensor configuration circuitry 209 may be configured to selectively configure an impactor nozzle of the fluid composition sensor between a first nozzle configuration and a second nozzle configuration. For example, the fluid composition sensor configuration circuitry 209 may transition an impactor nozzle between a first nozzle configuration, corresponding with a particle collection functionality of the fluid composition sensor, and a second nozzle configuration, corresponding to a particle analysis functionality of the fluid composition sensor, as described herein.

In various embodiments, the device 10 may be configured with, or in communication with, an imaging device data repository 107. The imaging device data repository 107 may be stored, at least partially on the memory 201 of the system. In some embodiments, the imaging device data repository 107 may be remote from, but in connection with, the device 10. The imaging device data repository 107 may contain information, such as images relating to one or more potential components of fluids. In some embodiments, the imaging device data repository 107, and/or other similar reference databases in communication with the device 10, may comprise non-image information used to identify particles (e.g., for florescent particles, a spectrometer may be used by the fluid composition sensor 100 as discussed herein and the device 10 may receive spectrum information to identify and/or classify the particles). In some embodiments, the device 10 may also use machine learning for identifying and/or classifying particles, such that the device 10 may use a reference database, such as the imaging device data repository 107, to initially train the device 10 and then may be configured to identify and/or classify particles without referencing the imaging device data repository 107 or other reference databases (e.g., a system may not be in active communication with the imaging device data repository 107 during regular operations).

Method

Figure 4:
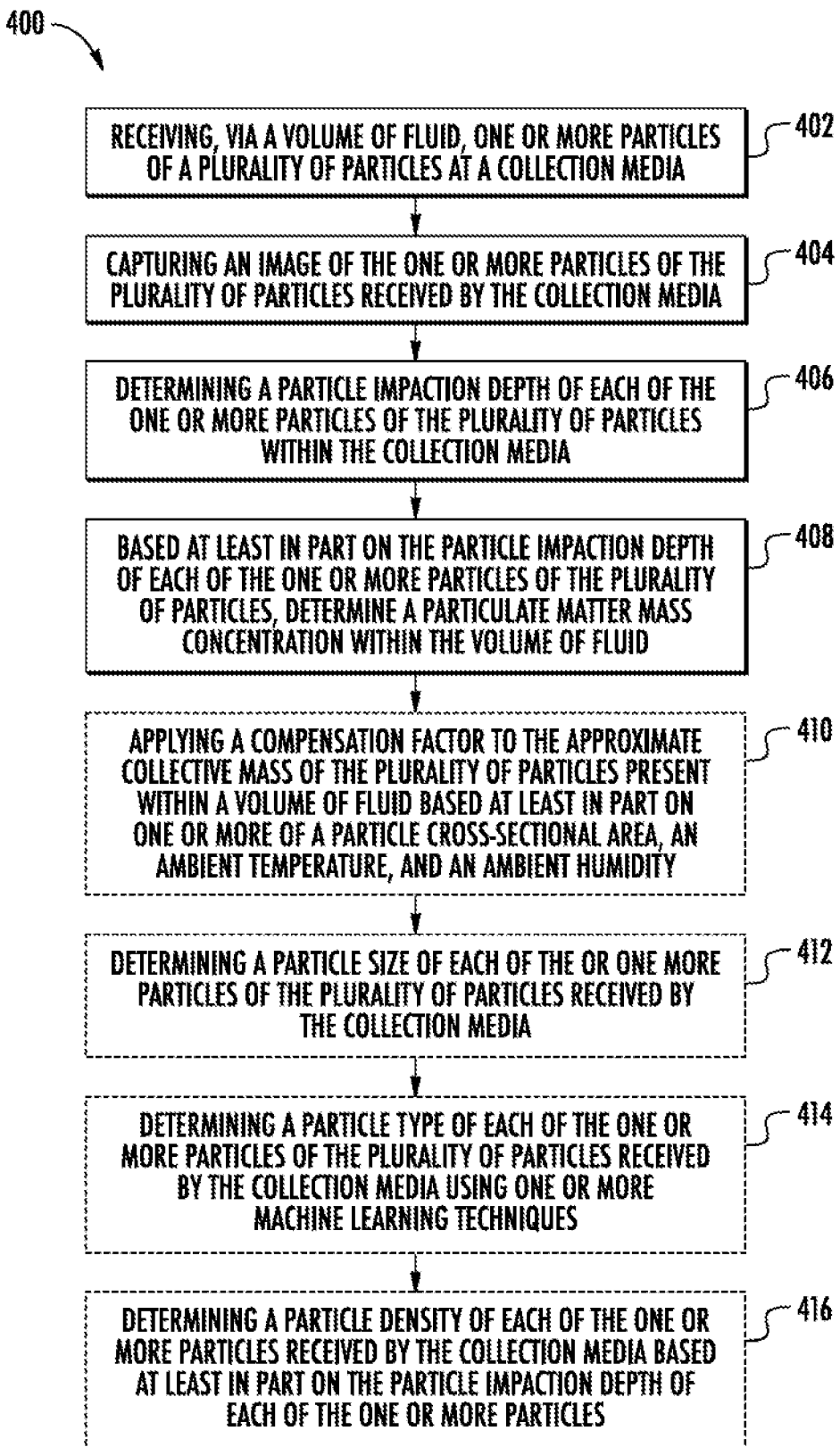
FIG. 4 illustrates a flow diagram of an exemplary method for detecting fluid particle characteristics of a fluid according to embodiments of the present disclosure.

FIG. 4 illustrates a block diagram of an exemplary method 400 for detecting fluid particle characteristics in accordance with some embodiments discussed herein.

At block 402, one or more particles of a plurality of particles may be received by a collection media via a volume of fluid. The plurality of particles may be received by the collection media from a volume of fluid comprising a plurality of particles. In various embodiments, the plurality of particles received by the collection media may be representative of a plurality of particles present within a volume of fluid. In various embodiments, a fluid composition sensor may comprise the collection media and may be configured so as to direct at least a portion of the volume of fluid in a direction perpendicular to a receiving surface of the collection media such that the volume of fluid may interact with the collection media.

Further, at block 404, an image is captured of the one or more particles of the plurality of particles received by the collection media. In various embodiments, the image of the one or more particles of the plurality of particles received by the collection media may be captured by an imaging device. In various embodiments, the imaging device may be configured to capture both an image of the one or more particles of the plurality of particles present within the collection media at the beginning of a particle analysis and an image of the one or more particles of the plurality of particles present within the collection media at the end of a particle analysis. The images may be compared to determine which of the one or more particles of the plurality of particles present within the collection media were received by the collection media during the particle analysis. In various embodiments, the imaging device may be disposed within a fluid composition sensor proximate the collection media such that the one or more particles of the plurality of particles received by the collection media are within a designated field of view of the imaging device. In various embodiments, the image of one or more particles of the plurality of particles received by the collection media may be captured using one or more imaging techniques, such as, for example lensless holography or optical microscopy. In various embodiments, the particle image may comprise a holographic image reconstruction.

At block 406, a particle impaction depth of each of the one or more particles of the plurality of particles within the collection media is determined. The particle impaction depth of a particle received by a collection media may be defined by the depth at which the particle is embedded into the collection media. In various embodiments, the particle impaction depth of each of the one or more particles of the plurality of particles within the collection media may be determined using an image captured by an imaging device. In various embodiments, the particle impaction depth of each of the one or more particles of the plurality of particles within the collection media may be determined based on a measured depth of focus, a distance between the imaging device and the transparent substrate, a thickness of the transparent substrate, and a collection media thickness, wherein the depth of focus is the distance between the imaging device and the particle. The depth of focus of a particle may be defined as the distance between an imaging device and the particle. In various embodiments, the depth of focus of each of the one or more particles of the plurality of particles received by the collection media may be determined using one or more image focusing techniques, such as a computational technique (e.g., Angular Spectrum Propagation) and/or a mechanical technique (e.g., opto-mechanical adjustment). In various embodiments, the impaction depth of each of the one or more particles of the plurality of particles within the collection media may be calculated by subtracting the measured depth of focus of each particle from the sum of the collection media thickness, a transparent substrate thickness, and a distance between the transparent substrate and the imaging device.

At block 408, an approximate collective mass of the plurality of particles present within a volume of fluid is determined based at least in part on the particle impaction depth of each of the one or more particles of the plurality of particles. In various embodiments, the respective determined particle impaction depths of each particle may be used to estimate the respective masses of each of the particles of the plurality of particles. In various embodiments, based on data in a particle impaction depth-momentum look-up table that correlates particle impaction depth to particle initial momentum for a given collection media type, the particle impaction depth and the measured particle size data may be used to determine the initial momentum of each particle prior to the particle being received by the collection media. Using a known relationship between momentum, velocity, and mass—the momentum of a particle is equal to the mass of the particle multiplied by the velocity of the particle—and a known velocity of each particle—a controlled value based on an air flow velocity of the volume of fluid—the estimated mass of each of the particles may be determined. In various embodiments, one or more compensation factors may be applied to the estimated mass of each of the particles to account for one or both of a particle condition associated with the particle and ambient conditions associated with an ambient environment. In various embodiments, for example, an appropriate compensation factor may be applied based at least in part on a particle cross-sectional area, an ambient temperature, and/or an ambient humidity. In various embodiments, the respective estimated masses of each of the particles of the plurality of particles may be used to determine the collective mass of the plurality of particles received by the collection media. In various embodiments, the determined collective mass of the plurality of particles received by the collection media may be used to approximate a collective mass of a plurality of particles present within the volume of fluid. In various embodiments, the approximated collective mass of a plurality of particles present within the volume of fluid may be used to estimate a particulate matter mass concentration within the volume of fluid. In various embodiments, one or more scale factors may be applied to the determined particulate matter mass concentration within the volume of fluid to account for experimental inefficiencies such as, for example, particle collection efficiencies and detection probability factors. In various embodiments, an appropriate scale factor may be determined based on empirical data.

At block 410, a compensation factor may be applied to the approximate collective mass of the plurality of particles present within a volume of fluid based at least in part on one or more of a particle cross-sectional area, an ambient temperature, and an ambient humidity. In various embodiments, a compensation factor may be applied to the estimated mass of each of the particles to account for one or both of a particle condition associated with the particle and ambient conditions associated with an ambient environment. In various embodiments, for example, a compensation factor may be applied to the estimated mass of a particle to account for the particle cross-sectional area because a larger particle cross-sectional area will disperse kinetic energy more quickly within the collection media, thereby decreasing the particle impaction depth. In various embodiments, a compensation factor may be applied to the estimated mass of a particle to account for the ambient temperature and/or ambient humidity because both the ambient temperature and ambient humidity affect the viscosity of the collection media, and therefore, the particle impaction depth. In various embodiments, the ambient temperature and humidity may be measured by either the device or one or more remote sensors configured to transmit temperature and humidity data to the device.

At block 412, the particle size of each of the one or more particles of the plurality of particles received by the collection media may be determined. In various embodiments, the particle size of each of the one or more particles may be determined based on the captured particle image. In various embodiments, the particle size of particles with a diameter of between about 0.3 and about 100 microns (e.g., 2.5 microns) may be determined, and a size category such as, for example, PM10, PM4, PM2.5, or PM1. In various embodiments, particle size data may comprise particle cross-sectional area data.

At block 414, a particle type of each of the one or more particles of the plurality of particles received by the collection media may be determined using one or more machine leaning techniques. In various embodiments, the one or more machine learning techniques used to determine the particle type of each of the one or more particles of the plurality of particles may comprise analyzing a captured particle image of the one or more particles, particle size data, and/or any other data associated with the one or more particles. In some embodiments, machine learning techniques may be used for identifying and/or classifying particles. In various embodiments, a reference imaging database comprising various particle data may be used to initially train a machine learning apparatus, which may then be then may be utilized to identify and/or classify particles without referencing the imaging database or other reference databases.

At block 416, a particle density of each of the one or more particles of the plurality of particles received by the collection media may be determined based at least in part on the particle impaction depth of each of the one or more particles. In various embodiments, the particle density of a particle may be determined based at least in part on one or more of the particle impaction depth, the estimated particle mass, the particle type, and the particle size data.

In various embodiments, the method described herein may further comprise replacing the collection media as described herein. In various embodiments, the collection media may be replaced based on one or more parameters such as, for example, time elapsed, number of particles received, and/or percentage of particle coverage within a field of view.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device for detecting fluid particle characteristics comprising:
   a fluid composition sensor comprising:
      a housing configured to support a collection media for capturing one or more particles of a plurality of particles within a volume of fluid passing through at least a portion of the housing;
      a pump to move the volume of fluid through the at least a portion of the housing and across at least a portion of the collection media;
      an imaging device configured to capture an image of at least a portion of one or more particles captured by the collection media; and
      a controller comprising a particle matter mass concentration calculation circuitry configured to determine one or more particle loading conditions of at least a portion of the one or more particles captured by the collection media based at least in part on the image captured by the imaging device, wherein the controller is configured to adjust an operation of the pump based at least in part on at least one of the one or more particle loading conditions of the at least a portion of the one or more particles captured by the collection media;
   wherein the particle matter mass concentration calculation circuitry is configured to stop the pump when a predetermined difference in a first particle loading condition and a second particle loading condition is calculated.

2. The device of claim 1, wherein the controller is configured to stop operation of the pump upon the particle matter mass concentration calculation circuitry determines that a predetermined total particle matter mass threshold is reached.

3. The device of claim 1, wherein determining the one or more particle loading conditions comprises determining the first particle loading condition of a first image and determining the second particle loading condition of a second image.

4. The device of claim 3, wherein determining the one or more particle loading conditions further comprises comparing the first particle loading condition to the second particle loading condition.

5. The device of claim 4, wherein determining the one or more particle loading conditions further comprises calculating a difference between the first particle loading condition and the second particle loading condition.

6. The device of claim 5, wherein the controller is configured to modify operation of the pump upon the particle matter mass concentration calculation circuitry determining that the predetermined difference in the first particle loading condition and the second particle loading condition is calculated.

7. The device of claim 1, wherein determining the one or more particle loading conditions further comprises identifying one or more particle clusters within the image captured by the imaging device.

8. The device of claim 1, wherein the imaging device is configured to capture images in set time intervals.

9. The device of claim 1, wherein the imaging device is configured to capture the image at a start of a fluid flow of the volume of fluid passing through the at least a portion of the housing.

10. The device of claim 9, wherein determining the one or more particle loading conditions comprises determining if the start of the fluid flow of the volume of fluid causes a spike in the one or more particle loading conditions.

11. The device of claim 1, wherein determining the one or more particle loading conditions further comprises calculating a particle matter mass of at least a portion of the one or more particles captured by the collection media based at least in part on a total intensity of light across the image thereof.

12. The device of claim 11, wherein the controller is configured to stop operation of the pump upon the particle matter mass concentration calculation circuitry determines that the total intensity of light detected within the image is below a threshold.

13. The device of claim 11, wherein the controller is configured to adjust the operation of the pump upon the particle matter mass concentration calculation circuitry determining that the total intensity of light detected within the image is below a threshold.

14. The device of claim 1, wherein determining the one or more particle loading conditions comprises determining a volume of the volume of fluid that flowed through the at least a portion of the housing over a defined time period.

15. The device of claim 14, wherein the volume of fluid that flowed through the housing over the defined time period is determined based at least in part on a pump run time and a pump flow rate.

16. A method for detecting fluid particle characteristics comprising:
    directing a flow of a volume of fluid toward a collection media,
    receiving, by the collection media, one or more particles of a plurality of particles within the volume of fluid,
    capturing an image of the one or more particles of the plurality of particles received by the collection media;
    determining one or more particle loading conditions of at least a portion of the one or more particles of the plurality of particles received by the collection media based at least in part on the image thereof, and
    adjusting the volume of fluid flowing toward the collection media;
    wherein adjusting the volume of fluid flowing toward the collection media comprises adjusting the volume of fluid upon detecting at least a threshold difference between a first particle loading condition and a second particle loading condition, wherein the first particle loading condition is determined for a first image and the second particle loading condition is determined for a second image captured after the first image.

17. The method of claim 16, wherein determining the one or more particle loading conditions comprises determining a total particle matter mass by a particle matter mass concentration calculation circuitry of a controller configured to adjust the volume of fluid flowing toward the collection media.

* * * * *